(12) United States Patent
Abbott et al.

(10) Patent No.: US 7,585,306 B2
(45) Date of Patent: Sep. 8, 2009

(54) ANASTOMOSIS DEVICE, TOOLS AND METHODS OF USING

(75) Inventors: Ryan Abbott, San Jose, CA (US); Greg C. Liu, Sunnyvale, CA (US)

(73) Assignee: MAQUET Cardiovascular LLC, San Jose, CA (US)

( * ) Notice: Subject to any disclaimer, the term of this patent is extended or adjusted under 35 U.S.C. 154(b) by 960 days.

(21) Appl. No.: 10/867,430

(22) Filed: Jun. 14, 2004

(65) Prior Publication Data

US 2005/0143758 A1    Jun. 30, 2005

Related U.S. Application Data

(63) Continuation-in-part of application No. 10/746,966, filed on Dec. 24, 2003.

(51) Int. Cl.
*A61B 17/11* (2006.01)
(52) U.S. Cl. ....................................................... 606/153
(58) Field of Classification Search ......... 606/151–157, 606/107, 191–198; 623/1.11–1.28; 128/898
See application file for complete search history.

(56) References Cited

U.S. PATENT DOCUMENTS

| | | | |
|---|---|---|---|
| 3,254,650 A | 6/1966 | Collito | |
| 3,254,651 A | 6/1966 | Collito | |
| 3,519,187 A | 7/1970 | Kapitanov et al. | |
| 3,774,615 A | 11/1973 | Lim et al. | |
| 4,118,806 A | 10/1978 | Porier et al. | |
| 4,214,587 A | 7/1980 | Sakura, Jr. | |
| 4,217,664 A | 8/1980 | Faso | |
| 4,350,160 A | 9/1982 | Kolesov et al. | |
| 4,352,358 A | 10/1982 | Angelchik | |
| 4,366,819 A | 1/1983 | Kaster | |
| 4,368,736 A | 1/1983 | Kaster | |
| 4,503,568 A | 3/1985 | Madras | |
| 4,523,592 A | 6/1985 | Daniel | |
| 4,553,542 A | 11/1985 | Schenck et al. | |
| 4,589,416 A | 5/1986 | Green | |
| 4,593,693 A | 6/1986 | Schenck | |
| 4,607,637 A | 8/1986 | Berggren et al. | |
| 4,624,255 A | 11/1986 | Schenck et al. | |
| 4,624,257 A | 11/1986 | Berggren et al. | |
| 4,657,019 A | 4/1987 | Walsh et al. | |
| 4,665,906 A | 5/1987 | Jervis | |
| 4,721,109 A | 1/1988 | Healey | |
| 4,747,407 A | 5/1988 | Liu et al. | |
| 4,752,024 A | 6/1988 | Green et al. | |
| 4,861,330 A | 8/1989 | Voss | |

(Continued)

FOREIGN PATENT DOCUMENTS

DE    29713335 U1    11/1997

(Continued)

*Primary Examiner*—Kevin T Truong
(74) *Attorney, Agent, or Firm*—Law Office of Alan W. Cannon

(57) ABSTRACT

Anastomosis devices, tools and methods of performing sutureless anastomosis. Anastomosis devices are provided for fixing a first conduit to a second conduit in an anastomosis, where the conduits are joined by interfacing their inner walls together. The conduit which is loaded on the anastomosis device may be mounted in such a way that the internal wall of the conduit does not make contact with the anastomosis device.

19 Claims, 28 Drawing Sheets

U.S. PATENT DOCUMENTS

| | | |
|---|---|---|
| 4,883,453 A | 11/1989 | Berry et al. |
| 4,892,098 A | 1/1990 | Sauer |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 4,997,439 A | 3/1991 | Chen |
| 5,005,749 A | 4/1991 | Aranyi |
| 5,015,238 A | 5/1991 | Solomon et al. |
| 5,062,842 A | 11/1991 | Tiffany |
| 5,089,006 A | 2/1992 | Stiles |
| 5,104,025 A | 4/1992 | Main et al. |
| 5,119,983 A | 6/1992 | Green et al. |
| 5,129,913 A | 7/1992 | Ruppert |
| 5,156,613 A | 10/1992 | Sawyer |
| 5,156,619 A | 10/1992 | Ehrenfeld |
| 5,171,262 A | 12/1992 | MacGregor |
| 5,178,634 A | 1/1993 | Martinez |
| 5,192,289 A | 3/1993 | Jessen |
| 5,193,731 A | 3/1993 | Aranyi |
| 5,205,459 A | 4/1993 | Brinkerhoff et al. |
| 5,211,683 A | 5/1993 | Maginot |
| 5,217,474 A | 6/1993 | Zacca |
| 5,221,281 A | 6/1993 | Klicek |
| 5,222,963 A | 6/1993 | Brinkerhoff et al. |
| 5,234,447 A | 8/1993 | Kaster et al. |
| 5,250,058 A | 10/1993 | Miller et al. |
| 5,250,060 A | 10/1993 | Carbo et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,290,298 A | 3/1994 | Rebuffat et al. |
| 5,292,053 A | 3/1994 | Bilotti et al. |
| 5,304,220 A | 4/1994 | Maginot |
| 5,314,435 A | 5/1994 | Green et al. |
| 5,314,468 A | 5/1994 | Martinez |
| 5,333,773 A | 8/1994 | Main et al. |
| 5,336,233 A | 8/1994 | Chen |
| 5,350,104 A | 9/1994 | Main et al. |
| 5,354,302 A | 10/1994 | Ko |
| 5,364,389 A | 11/1994 | Anderson |
| 5,366,462 A | 11/1994 | Kaster et al. |
| 5,392,979 A | 2/1995 | Green et al. |
| 5,395,030 A | 3/1995 | Kuramoto et al. |
| 5,395,311 A | 3/1995 | Andrews |
| 5,443,497 A | 8/1995 | Venbrux |
| 5,447,514 A | 9/1995 | Gerry et al. |
| 5,454,825 A | 10/1995 | Leeuwen et al. |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel et al. |
| 5,478,354 A | 12/1995 | Tovey et al. |
| 5,503,635 A | 4/1996 | Sauer et al. |
| 5,515,478 A | 5/1996 | Wang |
| 5,522,834 A | 6/1996 | Fonger et al. |
| 5,524,180 A | 6/1996 | Wang et al. |
| 5,533,661 A | 7/1996 | Main et al. |
| 5,534,761 A | 7/1996 | Crippa |
| 5,540,677 A | 7/1996 | Sinofsky |
| 5,553,198 A | 9/1996 | Wang et al. |
| 5,556,405 A | 9/1996 | Lary |
| 5,558,667 A | 9/1996 | Yarborough |
| 5,571,167 A | 11/1996 | Maginot |
| 5,643,340 A | 7/1997 | Nunokawa |
| 5,645,520 A | 7/1997 | Nakamura |
| 5,657,429 A | 8/1997 | Wang et al. |
| 5,669,918 A | 9/1997 | Balazs et al. |
| 5,669,934 A | 9/1997 | Sawyer |
| 5,676,670 A | 10/1997 | Kim |
| 5,693,088 A | 12/1997 | Lazarus |
| 5,695,504 A | 12/1997 | Gifford et al. |
| 5,702,412 A | 12/1997 | Popov et al. |
| 5,707,362 A | 1/1998 | Yoon |
| 5,707,380 A | 1/1998 | Hinchliffe et al. |
| 5,709,335 A | 1/1998 | Heck |
| 5,709,693 A | 1/1998 | Taylor |
| 5,725,533 A | 3/1998 | Carlsson |
| 5,725,544 A | 3/1998 | Rygaard |
| 5,725,553 A | 3/1998 | Moenning |
| 5,732,872 A | 3/1998 | Bolduc et al. |
| 5,754,741 A | 5/1998 | Wang et al. |
| 5,762,458 A | 6/1998 | Wang et al. |
| 5,779,718 A | 7/1998 | Green et al. |
| 5,789,371 A | 8/1998 | Tracy et al. |
| 5,792,135 A | 8/1998 | Madhani et al. |
| 5,797,900 A | 8/1998 | Madhani et al. |
| 5,797,920 A | 8/1998 | Kim |
| 5,799,661 A | 9/1998 | Boyd et al. |
| 5,799,857 A | 9/1998 | Robertson et al. |
| 5,807,377 A | 9/1998 | Madhani et al. |
| 5,814,073 A | 9/1998 | Bonutti |
| 5,815,640 A | 9/1998 | Wang et al. |
| 5,817,113 A | 10/1998 | Gifford et al. |
| 5,827,316 A | 10/1998 | Young et al. |
| 5,833,698 A | 11/1998 | Hinchliffe et al. |
| 5,841,950 A | 11/1998 | Wang et al. |
| 5,855,583 A | 1/1999 | Wang et al. |
| 5,868,763 A | 2/1999 | Spence et al. |
| 5,875,782 A | 3/1999 | Ferrari et al. |
| 5,878,193 A | 3/1999 | Wang et al. |
| 5,879,371 A | 3/1999 | Gardiner et al. |
| 5,881,943 A | 3/1999 | Heck et al. |
| 5,893,369 A | 4/1999 | LeMole |
| 5,904,697 A | 5/1999 | Gifford et al. |
| 5,907,664 A | 5/1999 | Wang et al. |
| 5,911,036 A | 6/1999 | Wright et al. |
| 5,915,616 A | 6/1999 | Viola et al. |
| 5,921,995 A | 7/1999 | Kleshinski |
| 5,944,730 A | 8/1999 | Nobles et al. |
| 5,947,363 A | 9/1999 | Bolduc et al. |
| 5,957,363 A | 9/1999 | Heck |
| 5,968,089 A | 10/1999 | Krajicek |
| 5,976,159 A | 11/1999 | Bolduc et al. |
| 5,989,276 A | 11/1999 | Houser et al. |
| 6,001,124 A | 12/1999 | Bachinski |
| 6,007,544 A | 12/1999 | Kim |
| 6,013,190 A | 1/2000 | Berg et al. |
| 6,015,416 A | 1/2000 | Stefanchik et al. |
| 6,022,367 A | 2/2000 | Sherts |
| 6,024,748 A | 2/2000 | Manzo et al. |
| 6,030,370 A | 2/2000 | Kupka et al. |
| 6,030,392 A | 2/2000 | Dakov |
| 6,030,395 A | 2/2000 | Nash et al. |
| 6,036,699 A | 3/2000 | Andreas et al. |
| 6,036,700 A | 3/2000 | Stefanchik et al. |
| 6,036,702 A | 3/2000 | Bachinski et al. |
| 6,036,703 A | 3/2000 | Evans et al. |
| 6,036,704 A | 3/2000 | Yoon |
| 6,050,472 A | 4/2000 | Shibata |
| 6,053,390 A | 4/2000 | Green et al. |
| 6,066,144 A | 5/2000 | Wolf et al. |
| 6,066,148 A | 5/2000 | Rygaard |
| 6,068,637 A | 5/2000 | Popov et al. |
| 6,074,401 A | 6/2000 | Gardiner et al. |
| 6,074,416 A | 6/2000 | Berg et al. |
| 6,080,173 A | 6/2000 | Williamson et al. |
| 6,110,187 A | 8/2000 | Donlon |
| 6,110,188 A | 8/2000 | Narciso, Jr. |
| 6,113,612 A | 9/2000 | Swanson et al. |
| 6,117,148 A | 9/2000 | Ravo et al. |
| 6,146,393 A | 11/2000 | Wakabayashi |
| 6,149,658 A | 11/2000 | Gardiner et al. |

| | | |
|---|---|---|
| 6,149,681 A | 11/2000 | Houser et al. |
| 6,152,937 A | 11/2000 | Peterson et al. |
| 6,152,945 A | 11/2000 | Bachinski et al. |
| 6,165,185 A | 12/2000 | Shennib et al. |
| 6,167,889 B1 | 1/2001 | Benetti |
| 6,168,623 B1 | 1/2001 | Fogarty et al. |
| 6,171,321 B1 | 1/2001 | Gifford et al. |
| 6,176,413 B1 | 1/2001 | Heck et al. |
| 6,176,864 B1 | 1/2001 | Chapman |
| 6,179,849 B1 | 1/2001 | Yencho et al. |
| 6,186,942 B1 | 2/2001 | Sullivan et al. |
| 6,187,019 B1 | 2/2001 | Stefanchik et al. |
| 6,187,020 B1 | 2/2001 | Zegdi et al. |
| 6,190,396 B1 | 2/2001 | Whitin et al. |
| 6,190,590 B1 | 2/2001 | Randall et al. |
| 6,193,129 B1 | 2/2001 | Bittner et al. |
| 6,193,734 B1 | 2/2001 | Bolduc et al. |
| 6,206,912 B1 | 3/2001 | Goldsteen et al. |
| 6,217,585 B1 | 4/2001 | Houser et al. |
| 6,235,054 B1 | 5/2001 | Berg et al. |
| 6,241,741 B1 | 6/2001 | Duhaylongsod et al. |
| 6,254,617 B1 | 7/2001 | Spence et al. |
| 6,293,955 B1 | 9/2001 | Houser et al. |
| 6,302,905 B1 | 10/2001 | Goldsteen et al. |
| 6,309,416 B1 | 10/2001 | Swanson et al. |
| 6,361,559 B1 | 3/2002 | Houser et al. |
| 6,371,965 B2 | 4/2002 | Gifford et al. |
| 6,387,105 B1 | 5/2002 | Gifford et al. |
| 6,391,038 B2 | 5/2002 | Vargas et al. |
| 6,398,797 B2 | 6/2002 | Bombard et al. |
| 6,401,721 B1 | 6/2002 | Maginot |
| 6,402,764 B1 | 6/2002 | Hendricksen et al. |
| 6,419,681 B1 | 7/2002 | Vargas et al. |
| 6,428,550 B1 | 8/2002 | Vargas et al. |
| 6,440,163 B1 | 8/2002 | Swanson et al. |
| 6,443,965 B1 | 9/2002 | Gifford et al. |
| 6,451,034 B1 | 9/2002 | Gifford et al. |
| 6,458,140 B2 | 10/2002 | Akin et al. |
| 6,461,320 B1 | 10/2002 | Yencho et al. |
| 6,461,365 B2 | 10/2002 | Bolduc et al. |
| 6,471,713 B1 | 10/2002 | Vargas et al. |
| 6,478,804 B2 | 11/2002 | Vargas et al. |
| 6,491,704 B2 | 12/2002 | Gifford et al. |
| 6,491,705 B2 | 12/2002 | Gifford et al. |
| 6,494,889 B1 | 12/2002 | Fleischman et al. |
| 6,497,710 B2 | 12/2002 | Yencho et al. |
| 6,508,252 B1 | 1/2003 | Berg et al. |
| 6,508,822 B1 | 1/2003 | Peterson et al. |
| 6,511,491 B2 | 1/2003 | Grudem et al. |
| 6,514,196 B1 | 2/2003 | Sullivan et al. |
| 6,514,265 B2 | 2/2003 | Ho et al. |
| 6,517,558 B2 | 2/2003 | Gittings et al. |
| 6,530,932 B1 | 3/2003 | Swayze et al. |
| 6,533,812 B2 | 3/2003 | Swanson et al. |
| 6,537,287 B1 | 3/2003 | Yencho et al. |
| 6,537,288 B2 | 3/2003 | Vargas et al. |
| 6,551,332 B1 | 4/2003 | Nguyen et al. |
| 6,554,764 B1 | 4/2003 | Vargas et al. |
| 6,565,581 B1 | 5/2003 | Spence et al. |
| 6,565,582 B2 | 5/2003 | Gifford et al. |
| 6,573,286 B1 | 6/2003 | Hegde et al. |
| 6,582,463 B1 | 6/2003 | Mowry et al. |
| 6,596,003 B1 | 7/2003 | Realyvasquez et al. |
| 6,599,303 B1 | 7/2003 | Peterson et al. |
| 6,599,313 B1 | 7/2003 | Maginot |
| 6,602,263 B1 | 8/2003 | Swanson et al. |
| 6,605,053 B1 | 8/2003 | Kamm et al. |
| 6,605,098 B2 | 8/2003 | Nobis et al. |
| 6,605,113 B2 | 8/2003 | Wilk |
| 6,607,541 B1 | 8/2003 | Gardiner et al. |
| 6,613,058 B1 | 9/2003 | Goldin |
| 6,613,059 B2 | 9/2003 | Schaller et al. |
| 6,616,675 B1 | 9/2003 | Evard et al. |
| 6,620,176 B1 | 9/2003 | Peterson et al. |
| 6,652,541 B1 | 11/2003 | Vargas et al. |
| 6,666,832 B1 | 12/2003 | Carranza et al. |
| 6,719,769 B2 | 4/2004 | Donohoe et al. |
| 2001/0051809 A1 | 12/2001 | Houser et al. |
| 2002/0013591 A1 | 1/2002 | Fleischman et al. |
| 2002/0032462 A1 | 3/2002 | Houser et al. |
| 2002/0052637 A1 | 5/2002 | Houser et al. |
| 2002/0099393 A1 | 7/2002 | Fleischman et al. |
| 2002/0099394 A1 | 7/2002 | Houser et al. |
| 2002/0173808 A1 | 11/2002 | Houser et al. |
| 2002/0173809 A1 | 11/2002 | Fleischman et al. |
| 2003/0023253 A1 | 1/2003 | Vargas et al. |
| 2003/0028205 A1 | 2/2003 | Vargas et al. |
| 2003/0074012 A1 | 4/2003 | Nguyen et al. |
| 2003/0078603 A1 | 4/2003 | Schaller et al. |
| 2003/0093118 A1 | 5/2003 | Ho et al. |
| 2003/0120293 A1 | 6/2003 | Yencho et al. |

FOREIGN PATENT DOCUMENTS

| | | |
|---|---|---|
| EP | 0 539 237 A1 | 4/1993 |
| EP | 0 517 252 B1 | 8/1995 |
| EP | 0 701 800 A1 | 3/1996 |
| EP | 0 913 125 A2 | 5/1999 |
| EP | 0 913 125 A3 | 5/1999 |
| EP | 0 938 870 A1 | 9/1999 |
| EP | 0 820 724 B1 | 3/2000 |
| EP | 0 820 725 B1 | 3/2000 |
| EP | 0 990 420 A2 | 4/2000 |
| EP | 0 885 595 B1 | 8/2001 |
| WO | WO 92/08513 | 5/1992 |
| WO | WO 95/17128 | 6/1995 |
| WO | WO 95/35065 | 12/1995 |
| WO | WO 96/25886 | 8/1996 |
| WO | WO 97/25002 | 7/1997 |
| WO | WO 97/27898 | 8/1997 |
| WO | WO 97/31575 | 9/1997 |
| WO | WO 97/47261 | 12/1997 |
| WO | WO 98/02099 | 1/1998 |
| WO | WO 98/07399 | 2/1998 |
| WO | WO 98/19608 | 5/1998 |
| WO | WO 98/19618 | 5/1998 |
| WO | WO 98/19625 | 5/1998 |
| WO | WO 98/19629 | 5/1998 |
| WO | WO 98/19630 | 5/1998 |
| WO | WO 98/19631 | 5/1998 |
| WO | WO 98/19632 | 5/1998 |
| WO | WO 98/19634 | 5/1998 |
| WO | WO 98/19636 | 5/1998 |
| WO | WO 98/30153 | 7/1998 |
| WO | WO 98/37814 | 9/1998 |
| WO | WO 98/40036 | 9/1998 |
| WO | WO 98/42262 | 10/1998 |
| WO | WO 98/47430 | 10/1998 |
| WO | WO 98/55027 | 12/1998 |
| WO | WO 99/08603 | 2/1999 |
| WO | WO 99/17665 | 4/1999 |
| WO | WO 99/18887 | 4/1999 |
| WO | WO 99/21491 | 5/1999 |
| WO | WO 99/37218 | 7/1999 |
| WO | WO 99/38441 | 8/1999 |
| WO | WO 99/38454 | 8/1999 |
| WO | WO 99/40851 | 8/1999 |
| WO | WO 99/40868 | 8/1999 |
| WO | WO 99/45848 | 9/1999 |
| WO | WO 99/52481 | 10/1999 |
| WO | WO 99/62406 | 12/1999 |
| WO | WO 99/62409 | 12/1999 |
| WO | WO 99/62415 | 12/1999 |
| WO | WO 99/63910 | 12/1999 |
| WO | WO 99/65409 | 12/1999 |
| WO | WO 00/09040 | 2/2000 |

| | | | | | | |
|---|---|---|---|---|---|---|
| WO | WO 00/10486 | 3/2000 | | WO | WO 00/66007 | 11/2000 |
| WO | WO 00/12013 | 3/2000 | | WO | WO 00/66009 | 11/2000 |
| WO | WO 00/15144 | 3/2000 | | WO | WO 00/69343 | 11/2000 |
| WO | WO 00/15146 | 3/2000 | | WO | WO 00/69346 | 11/2000 |
| WO | WO 00/15147 | 3/2000 | | WO | WO 00/69349 | 11/2000 |
| WO | WO 00/15148 | 3/2000 | | WO | WO 00/69364 | 11/2000 |
| WO | WO 00/15149 | 3/2000 | | WO | WO 00/72764 | 12/2000 |
| WO | WO 00/27310 | 5/2000 | | WO | WO 00/74579 | 12/2000 |
| WO | WO 00/27311 | 5/2000 | | WO | WO 00/76405 | 12/2000 |
| WO | WO 00/27312 | 5/2000 | | WO | WO 01/08601 | 2/2001 |
| WO | WO 00/27313 | 5/2000 | | WO | WO 01/12074 | 2/2001 |
| WO | WO 00/33745 | 6/2000 | | WO | WO 01/15607 | 3/2001 |
| WO | WO 00/41633 | 7/2000 | | WO | WO 01/17440 | 3/2001 |
| WO | WO 00/53104 | 9/2000 | | WO | WO 01/19257 | 3/2001 |
| WO | WO 00/56223 | 9/2000 | | WO | WO 01/19259 | 3/2001 |
| WO | WO 00/56226 | 9/2000 | | WO | WO 01/19284 | 3/2001 |
| WO | WO 00/56227 | 9/2000 | | WO | WO 01/34037 | 5/2001 |
| WO | WO 00/56228 | 9/2000 | | WO | WO 01/41653 | 6/2001 |
| WO | WO 00/59380 | 10/2000 | | | | |

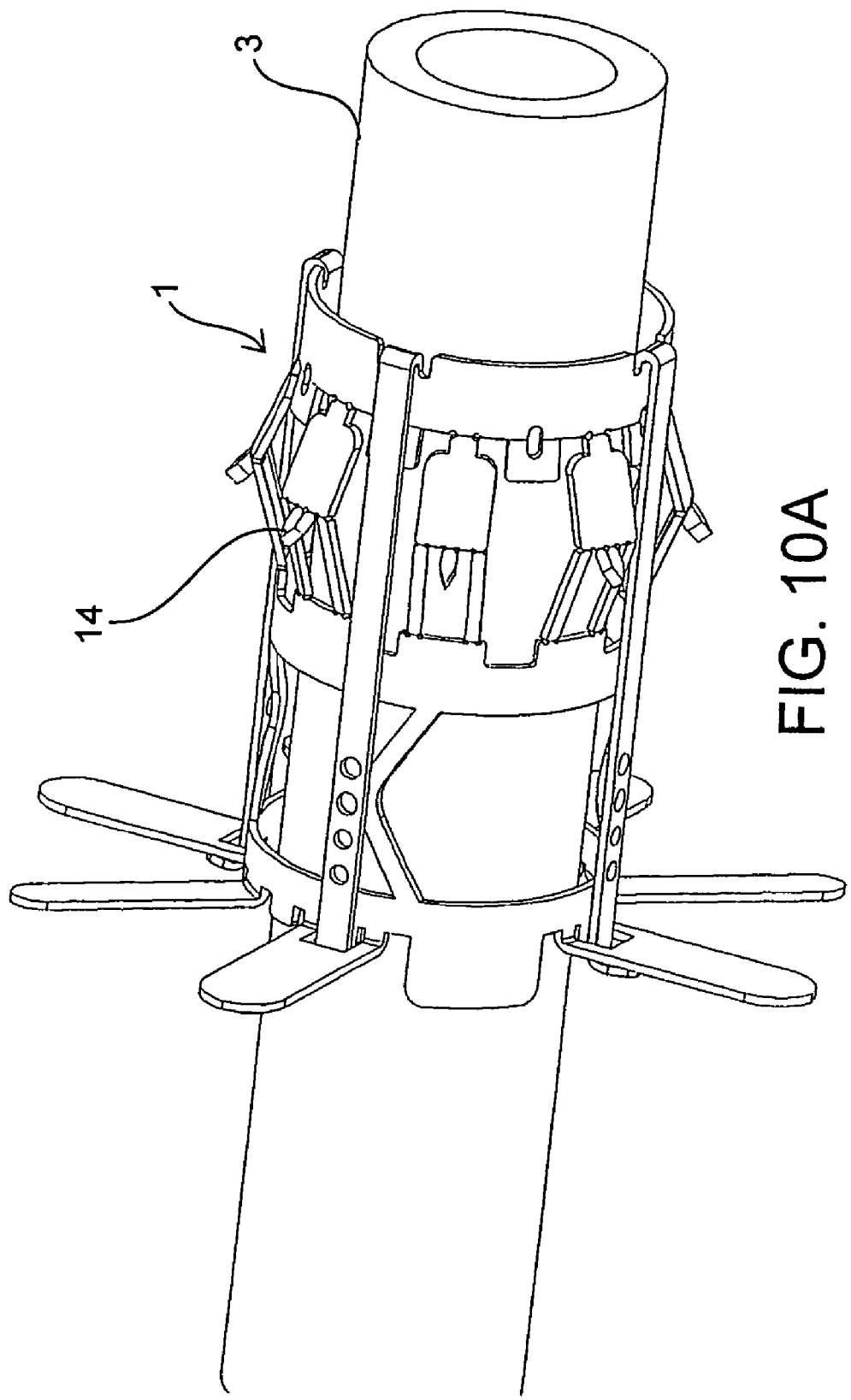

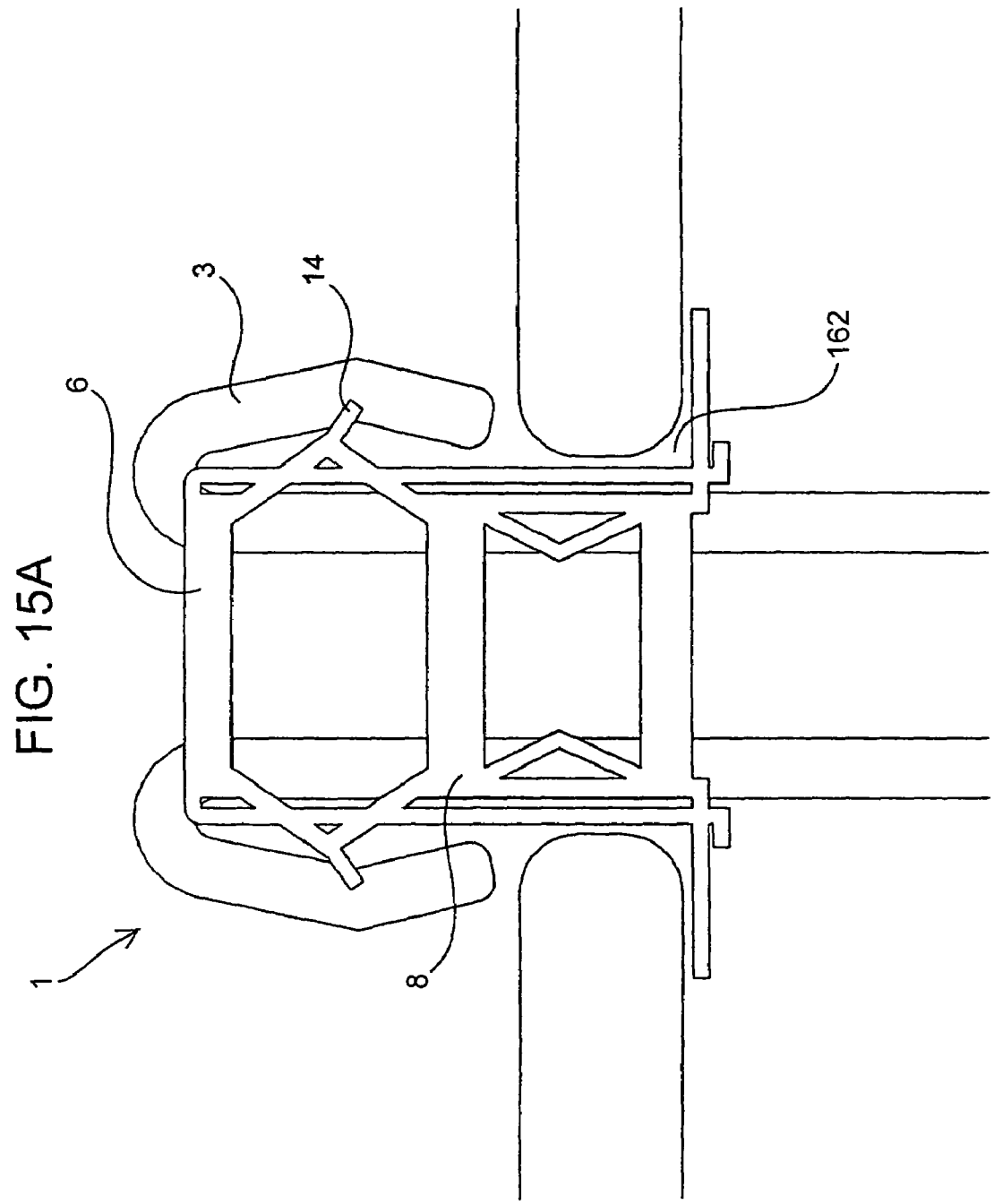

ANASTOMOSIS DEVICE, TOOLS AND METHODS OF USING

CROSS-REFERENCE

This application is a continuation-in-part application of co-pending application Ser. No. 10/746,966 filed Dec. 24, 2003, and titled "Anastomosis Device, Tools and Method of Using", which is incorporated herein by reference in its entirety and to which application we claim priority under 35 USC §120.

FIELD OF THE INVENTION

The present invention relates to the field of surgery. More particularly, the present invention relates to devices, tools and methods for performing sutureless anastomoses.

BACKGROUND OF THE INVENTION

There are many medical procedures which require the performance of one or more anastomoses in which a conduit such as a vessel, duct, graft or other tubular structure must be joined to another vessel, duct, or other hollow structure such as an organ to establish continuity between these structures. One of the more prevalent needs for improving anastomosis techniques lies with the treatment of coronary artery disease, where a stenosis of one or more coronary arteries prevents or seriously interferes with a normal blood supply to the heart tissue. In such situations, a total or partial blockage of a coronary artery is often treated by bypassing the obstruction in a heart bypass procedure, such as a coronary artery bypass graft (CABG) procedure, in which a graft is fluidly connected to the blood supply on opposite sides of the site of the stenosis to provide an alternate route for the blood to take on route to the heart.

The graft may be natural conduit, artificial conduit, or a combination of natural and artificial conduits. Typically, a natural conduit in the form of an autograft is used, wherein a saphenous vein is harvested from the leg of the patient or the internal mammary artery is rerouted to be anastomosed downstream of the site of the stenosis.

Conventional CABG procedures are currently performed while the beating of the heart has been stopped, with the circulation and oxygenation of the patient's blood being performed by a heart and lung bypass machine. During this procedure, the aorta of the patient is cross-clamped. Recently, it has been found that the clamping of the aorta introduces a risk of dislodging plaque that may have accumulated on the internal wall of the aorta in the vicinity of the clamping. Dislodgment of plaque can cause emboli in various locations in the patient's body, cutting off the blood supply downstream of the locus of the embolus, which can cause a stroke or other serious medical complications. Further, the heart-lung bypass machine can cause mechanical damage to the blood cells which furthers the risk of medical complications, due to potential clot formation.

Recently there has been an increase in the performance of beating heart CABG procedures, in which the bypass of one or more stenoses is performed while the patient's heart continues to beat, with the circulation and oxygenation of the patient's blood being performed naturally by the heart and lungs of the patient, and during which the aorta is not clamped. While beating heart procedures reduce the associated risks of stroke and other post-operative complications associated with the clamping of the aorta and the use of the heart-lung bypass machine, they also increase the difficulty in performing what were already difficult and delicate anastomosis procedures that must be performed to connect the bypass graft or grafts during the CABG procedure.

The most conventional techniques for making anastomoses involves manually suturing the two tubular conduits together (e.g., manually suturing the graft to the target vessel) around an opening between them. Manual suturing is difficult, time-consuming and requires a great deal of skill and manual dexterity on the part of the surgeon performing the anastomosis. Because of the high level of skill, dexterity and patience required, the results of manual suturing vary considerably from one anastomosis to the next, and from one surgeon to the next. The difficulties presented in performing anastomoses by manual suturing are only magnified when they are done during a beating heart CABG procedure as the beating of the heart introduces perturbations that make it even more difficult to throw the sutures in a reliable and consistent manner.

Thus, there is a need for sutureless anastomosis devices, tools and techniques that offer a reliable alternative to suturing techniques, and which are relatively easier to implement while giving consistent results. It would further be desirable to provide such devices, tools and techniques that would facilitate the performance of higher quality anastomoses than those currently made and with less time required to make the anastomoses.

With continued interest and development toward CABG procedures which are even less invasive than the current techniques for beating heart CABG procedures, it will further be desirable to provide anastomosis techniques which can be performed endoscopically, with the surgeon working outside of the patient.

SUMMARY OF THE INVENTION

The present invention provides devices, tools and methods for performing an anastomosis to join a first conduit to a second conduit. For application to cardiac surgery, the anastomosis may be performed either with the heart stopped or while the heart continues to beat.

A method of performing an anastomosis to join a first conduit to a second conduit is described, to include inserting a free end of the first conduit through an annular space defined by an anastomosis device so that the free end extends beyond a second end of the device, and wherein at least one first end member of the device extends further radially outward than a radial extent of the main body of the device defining the annular space; everting the extending free end of the graft over the second end of the device, wherein the inner wall of the graft remains free from contact with the device; forming an opening through a wall of the second conduit, wherein the opening is dimensioned to allow the everted end and main body, but not the at least one first end member to pass therethrough; inserting the device and graft into the opening until the at least one first end member abuts the external wall of the second conduit; and compressing the device to buckle the second end portion, wherein the second end portion, upon buckling is no longer capable of passing back through the opening.

The compression of the device may be performed only up until a pre-defined compression force has been reached. Further, the amount of compression of the device may be variable to account for varying wall thicknesses of the conduits to be joined.

After compression of the device is complete, the device may be further locked into position by locking the relative positions of first and second end portions of the device.

The compression of the device may also act to further evert the conduit held thereby, and draw the everted inner wall of the held conduit against an inner wall of the second conduit.

By the described method, the first and second conduits may be joined by contact between inner wall surfaces of the first and second conduits, free of any contact with the device.

One procedure described for performing an anastomosis of a graft vessel to a target vessel includes measuring an outside diameter and wall thickness of the graft vessel; selecting an appropriately sized anastomosis device, based on the outside diameter and wall thickness measurements; loading the graft vessel on the anastomosis device so that the graft vessel passes through a longitudinally extending annular space defined by a main body of the anastomosis device, extends beyond a distal end of the anastomosis device and is everted back over an external surface of the distal end of the anastomosis device; selecting a punch appropriately size matched to the outside diameter and wall thickness measurements and punching an opening through a wall of the target vessel; inserting the loaded graft into the opening, wherein the anastomosis device has an enlarged proximal end that is incapable of passing through the opening and abuts against the wall of the target vessel upon inserting the loaded graft; and buckling the anastomosis device so that a distal end portion thereof increases in diameter and compresses the everted end of the graft vessel against an internal wall surface of the target vessel. The graft may have only one free end at the time of performance of the anastomosis, or may have two free ends.

Devices for use in making an anastomosis between tubular fluid conduits in the body of a patient are described. An exemplary device includes a unitary structure having a main body disposed annularly about a longitudinal axis and having first and second end portions, and a plurality of members extending radially outwardly from the first end portion. The said second end portion adapted to buckle in a radially outward, direction upon axial compression of the device. The device is adapted to be loaded with one of the two conduits to be joined by the anastomosis, wherein the conduit is loaded by passing a free end thereof through an internal space defined by the main body in a direction from the first end portion to the second end portion, and everting the free end over the second end portion, so that the internal wall of the loaded conduit is free from contact with the device.

The device may further include graft tines extending from the second end portion, which are adapted to pierce the everted free end of the conduit.

The device may further include a plurality of spaced locking tines integral with the second end portion and slidably connecting with the first end portion, which are used to fix a relative positioning between the first and second end portions after compression of the device.

A device holder for securing an anastomosis device for loading a graft thereon is provided. The device holder includes a first portion dimensioned to receive a base portion of the anastomosis device, and a second portion adapted to interact with the first portion to apply a clamping force for retaining the anastomosis device between the first and second portions, so that the device holder securely holds the anastomosis device without applying any hoop stress to the anastomosis device.

In one example, the device holder includes a holder arm dimensioned to receive a radially extending end portion of the anastomosis device, and a clamp arm pivotally connected to the holder arm. The clamp arm includes a compression surface adapted to apply a compressive force to the radially extending end portion held by the holder arm upon locking the clamp arm against the holder arm.

When in a locked state, the clamp arm compresses the radially extending end portion against the holder arm. When in an unlocked state, the clamp arm is adapted to articulate away from the holder arm, thereby allowing the anastomosis device to be removed from the holder arm.

In another example, the first portion of the device holder includes at least one recess for receiving at least a part of the base portion of the anastomosis device, and the second portion includes a removable clamping element adapted to slide over the first portion to capture the anastomosis device, and to be removed from the first portion to release the anastomosis device.

With this device holder, an anastomosis device can be captured without application of any compressive force to the anastomosis device.

The removable clamping element of the device may further include at least one recess for receiving at least a part of said base portion of the anastomosis device.

Still further, a graft securing element may be provided to secure a position of a graft during loading of the graft on the device as it is held by the device holder.

A device guard may be provided to protect an anastomosis device as it is held by the device holder. The device guard is removable for performance of loading a graft on the anastomosis device, as well as for loading the device on a deployment instrument.

A graft loading tool for facilitating the loading of a graft on an anastomosis device to be used in the performance of an anastomosis of the graft to a vessel is provided. The graft loading tool includes a long, thin member formed of a high tensile strength material having proximal and distal end portions; a hook formed at a distal end of the distal end portion; and a sheath surrounding a portion of the long, thin member and being axially slidable with respect thereto. The hook is adapted to pierce a wall of the graft, and the long thin member is dimensioned to be threaded through the slot of the deployment instrument and axially through an interior of a captured device, wherein, upon threading the proximal end portion of the loading device through the anastomosis device, the graft can then be pulled into the slot and through an internal space defined by the anastomosis device.

A graft loader for facilitating the loading of a graft on an anastomosis device having already been captured on a deployment tool is disclosed, wherein the graft loader includes a main body having first and second portions configured to split apart. The graft loader is configured to be mounted over a distal end of the deployment device over the anastomosis device, and each portion includes at least one slot for receiving and holding a long thin member having been threaded through the tube and loader. The hook end of each long thin member is pierced through a wall of the graft to be loaded prior to threading the long thin members through the deployment tool and graft loader. After threading the long thin members through the deployment tool and graft loader, the long thin members can be pulled distally to draw the graft into the longitudinal slot of the deployment tool and through the loader.

Upon drawing the graft into the slot and through the interior of the tube and loader, the loader can be split apart, so that the first and second portions can be manipulated to evert a distal end of the graft which the hooks have pierced, and to mount the everted distal end of the graft on graft retainers extending from an exterior of the anastomosis device.

The first and second portions of the loader may each be provided with a handle extending therefrom for facilitating splitting of the main body.

A pre-load tool for preparing a graft to be mounted on an anastomosis device is provided to include a longitudinally extending main body portion having first and second ends, with the first end being tapered and dimensioned to be at least partially received in an end of the graft. A first set of guides spaced about a first end portion of the main body are provided for receiving long thin member portions of graft loading tools and maintaining them in a spaced configuration. A second set of guides may be spaced about a second end portion of the main body and axially aligned with the first set of guides, for receiving the long thin member portions and maintaining the long thin member portions substantially parallel to one another.

The tapered first end of the pre-load tool may be provided with circumferentially spaced recesses which are axially aligned with the first set of guides.

At least one graft loading tool may be threaded through the first and second sets of guides. A graft is partially inserted over the tapered end of the preloading tool, with the wall of the end of the graft extending between the tapered end and the hook or hooks of the preloading tool or tools. The hook or hooks are then pressed against the recesses of the tapered end, which act as anvils against which the hooks are pierced through the wall of the graft.

Another example of a loading tool is provided in which the loading tool is adapted to be mated with a deployment instrument, such as by sliding over the distal end portion of the deployment instrument, for example. A plurality of elongated hooks are slidably mounted with respect to a main body of the loading tool, and are adapted to slide through an internal opening of an anastomosis device that has been captured by the deployment instrument. The hooks are configured to move between an open, unbiased position when slid proximally of the anastomosis device, to receive a free end of a vessel to be loaded through the anastomosis device, and a gripping position, where the hooks grip the vessel and may be used to draw the vessel though the anastomosis device.

An assembly is provided wherein an anastomosis device is captured by a deployment instrument and a loading tool is removably mounted over the anastomosis device and the distal end portion of the deployment instrument.

Further provided are additional tools for loading and/or everting a vessel with respect to an anastomosis device. One example of an eversion tool includes a proximal end portion adapted to guide the eversion tool into a distal end of the vessel to be everted, and an expandable member positioned between the proximal end portion and a main body portion of the tool. The expandable member is capable of assuming a first outside diameter, in its relatively unbiased or non-expanded state, which is of a size that permits it to be slid into the open end of the vessel. Upon compressing the expandable member between the proximal end portion and the main body portion, the expandable member assumes a second outside diameter greater than the first outside diameter, which is sufficient to expand the vessel, facilitating the ease with which the vessel end may be flipped over to evert it.

A combination tool is provided which includes the eversion tool described in the previous paragraph, as well as a mechanism to load the free end of the graft over the expandable member. Additionally, the combination tool may include a member for driving the expanded vessel off the expanded expandable member, thereby everting the vessel.

Another example of an eversion tool includes a plurality of elongated prong members extending proximally from a main body portion, which are moveable between a contracted configuration in which proximal ends of the prong members closely surround a main shaft of the tool, and an expanded configuration in which the proximal ends radially expand away from the main shaft to expand the end of the vessel.

The main shaft may be slidably mounted with respect to the main body portion of the tool and may be biased to a distal-most sliding position with respect to the main body portion. Further, a proximal portion of the main shaft may be slidable with respect to a distal portion of the main shaft, such as in a telescoping manner, for example. The proximal portion of the main shaft may be biased to a proximal-most sliding position with respect to the distal shaft portion.

The proximal portion includes an anchor configured to wedge the vessel against an inner surface of the anastomosis device to prevent backsliding of the vessel with respect to the anastomosis device during performance of the eversion.

Still further, a scraper member may be slidably mounted over the main body portion of the tool and is actuatable to slide over the prong members to ensure that the vessel end has fully released from the prong members upon performing the everting step of the eversion process.

A removable cutting tool adapted to be removably mounted to an anastomosis device deployment instrument is provided for use in making an opening in a target vessel during the performance of an anastomosis. The cutting blade of the cutting tool is retractable, so as to be moved out of the target area after making the opening, to allow the deployment instrument to deliver the anastomosis device and graft vessel to the site of the opening.

A foot member may be provided to gauge the extent of the opening formed by the cutting member. Further, the foot member may function to keep the deployment device sited over the opening.

A graft sizing tool may be employed to determine the size of an anastomosis device to be used in performing the anastomosis. The graft sizing tool includes at least one first gauge adapted to measure an outside diameter of the graft, and at least one second gauge to measure the wall thickness of the graft. Further, means for indicating the size of anastomosis device to be used, based on the measured outside diameter and wall thickness of the graft, may be provided.

The graft sizing tool may be provided with a first series of gauges having varying gap sizes for measuring the outside diameter of the graft, and a second series of gauges mounted at varying distances from a main body of the tool for measuring a wall thickness of the graft.

Alternatively, the graft sizing tool may be provided with a graduated slot for measuring the outside diameter of the graft, and a plurality of semicircular grooves along the edge of the main body of the tool for measuring the wall thickness of the graft.

The main body of the tool may be of unitary design, or may include a pair of concentric disks which are relatively rotatable to one another.

An indicator may be provided for matching a measured wall thickness and outside diameter with an appropriately sized anastomosis device on which to mount the graft. The indicator may include color coding, which is color matched to appropriately sized anastomosis devices, and optionally to appropriately sized tools for installing the anastomosis device.

These and other features of the invention will become apparent to those persons skilled in the art upon reading the details of the devices, tools and methods as more fully described below.

BRIEF DESCRIPTION OF THE DRAWINGS

FIG. 10A is a perspective view of a graft vessel having been passed through the annular space defined by an anastomosis device having shortened tines according to the present invention.

FIG. 15A is a sectional schematic view of a graft and anastomosis device having been inserted into a target vessel.

DETAILED DESCRIPTION OF THE INVENTION

Figure 1A:
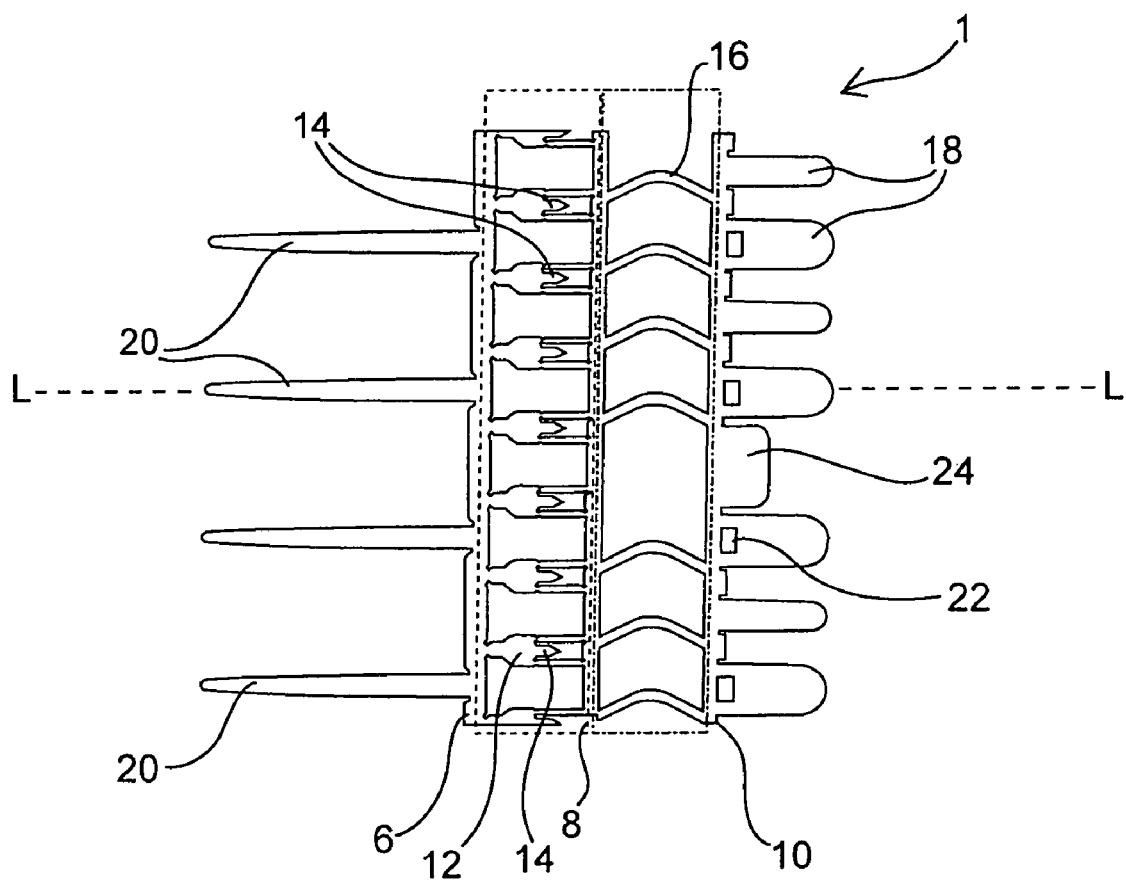
FIG. 1A shows a flat pattern of an anastomosis device for use according to the present invention.

Before the present devices, tools and methods are described, it is to be understood that this invention is not limited to a particular device, method step, or tool described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a tine" includes a plurality of such tines and reference to "the strut" includes reference to one or more struts and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "tine" is used herein to denote an elongated structure forming a portion of an anastomosis device as described. A "tine" generally has a free end which can have either a pointed or non-pointed tip.

A "strut" is defined herein to refer to a structurally supporting connecting element which joins at least two other components of an anastomosis device, such as two rings, for example.

A "ring" as used herein, refers to a body-shaping member of the anastomosis device which forms a general configuration over which a graft is mounted.

The present invention provides devices, tools and methods for joining two tubular conduits, such as vessels, organs or other tubular formations, particularly for forming anastomoses in cardiovascular applications, such as those required during the performance of a cardiopulmonary bypass. The present invention avoids the need by prior anastomosis techniques wherein the aorta is clamped to interrupt blood flow to the area of the aortic wall to which a vein or other graft is to be anastomosed. Such clamping may result in liberation of plaques and tissue fragments which can lead to organ dysfunction, such as strokes, renal failure, or intestinal ischemia. The anastomosis techniques according to the present invention do not require additional space surrounding the site of the anastomosis and inside the patient to connect the anastomotic device to the target vessel. According to the invention, a sutureless connection can be provided between a graft and a target vessel, while minimizing thrombosis or restenosis associated with the anastomosis. The devices allow the anastomosis to be performed very rapidly, with high reproducibility and reliability, without clamping, and with or without the use of cardiopulmonary bypass.

Device

FIG. 1A shows, for ease of description, a flat pattern of an anastomosis device 1 according to the present invention. Practically speaking, device 1 is generally formed integrally, as an annular structure, such as by laser cutting from tubular stock, for example, although it would be possible to cut or stamp a planar structure from a sheet of material and then weld or otherwise fix the device in its annular form. FIG. 1A therefore shows the device 1 as if it were cut along a line parallel to its longitudinal axis L and then flattened into a planar form. The device 1 may be made from stainless steel, such as medical grade 316L stainless steel, for example, or from other plastically deformable materials having appropriate performance characteristics, such as tantalum, tungsten or platinum, for example.

The device 1 can be formed in various sizes to suit the dimensions of a graft or vessel to be joined to another site. For purposes of establishing a proximal anastomosis during performance of a coronary bypass procedure, devices 1 having outside diameters 2 varying within the range of about 3.0 mm to about 7.0 mm, a material thickness of about 0.007"±0.003", and having an initial length 4 of about 0.2" to about 0.7", generally about 0.25", so that they are adapted to accommodate anastomosis of a graft to aortas having wall thicknesses within the range of about 1 mm to about 5 mm.

Figure 2:
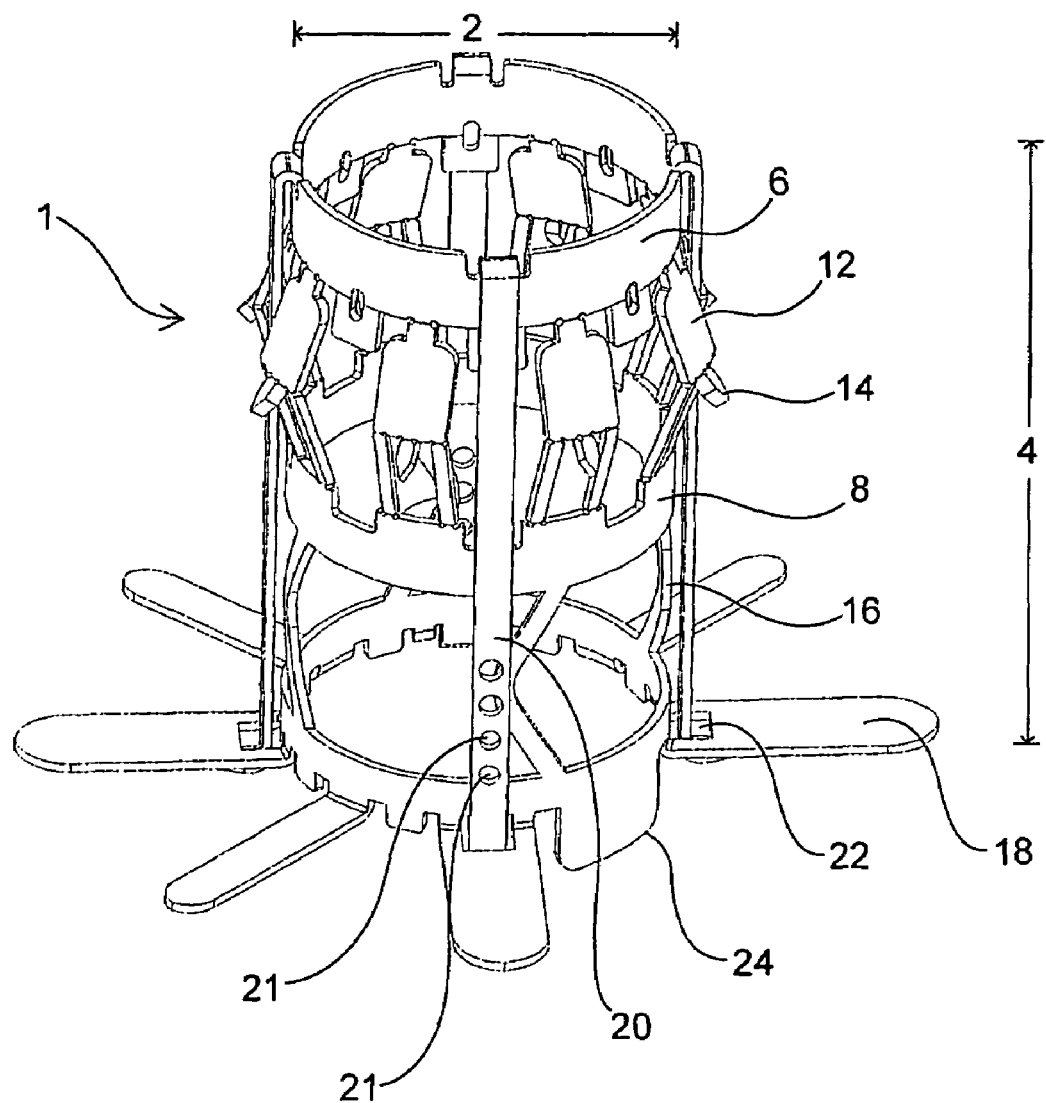
FIG. 2 is a three-dimensional, perspective view of the device shown in FIG. 1B.

Device 1 includes three rings 6, 8 and 10 which form a framework of a cylindrical structure as can be seen in FIG. 2. Buckling struts 12 join rings 6 and 8 and are generally equally spaced around the circumferences of the rings 6 and 8 to form a buckling portion of the device 1. Buckling struts 12 are bent outwardly from an outer surface of an imaginary cylinder defined by rings 6, 8 and 10, to make the buckling portion more susceptible to collapse than the remainder of device 1 upon exertion of compressive forces along the longitudinal axis of device 1. Buckling struts 12 are further cut out to form graft tines 14, which further weaken the buckling struts to make them more susceptible to buckling. Graft tines 14 are bent to positions substantially perpendicular to the longitudinal axis of device 1 during forming, to position them for anchoring the end of a graft, which function is discussed in greater detail below. Alternatives to graft tines include spikes, glue, a rubber pad that is stegging, or other features designed to hold the graft in an everted configuration during performance of an anastomosis. Another alternative is to completely forego tines or any other structure for holding the graft in the everted configuration, and instead, to simply evert the graft end over the structure of the device 1.

Support struts 16 join rings 8 and 10 and are generally equally spaced around the circumferences of the rings 8 and 10 to form a supporting portion of the device 1, which buckles only secondarily to the buckling portion. Support struts 16 are angled to enhance their buckling, but, in contrast to buckling struts 12, the bending angle of the support struts 16 is such that support struts 16 maintain conformity with the imaginary cylindrical surface defined by rings 8 and 10. Comparatively, when the buckling section collapses, buckling struts bend outwardly so as to effectively increase the outside diameter of that portion of the device 12, while, in contrast, struts 16 tend to bend or buckle in a direction substantially perpendicular to the direction that struts 12 bend in, so that the struts 16, even after bending, substantially conform to the imaginary cylindrical surface and do not substantially increase the outside diameter of the support portion of the device 1.

External tines 18 extend from ring 10 and are bent substantially perpendicularly to the longitudinal axis L of device 1 during forming. External tines 18 form the contact surface by which device 1 applies pressure to the external surface of a vessel (e.g., external wall of the aorta) to which a graft held by device 1 is being joined. Locking tines 20 extend from ring 6 at substantially evenly spaced locations about the circumference of ring 6. Locking tines 20 have a sufficient length to span the remaining length of device 1 when they are folded over by one hundred and eighty degrees during forming. The external tines 18 which are aligned with locking tines 20 contain locking receptacles 22 through which the respective locking tines 20 pass upon folding them back one hundred and eighty degrees during forming. The locking tines 20 are bent over to the external side of the general cylindrical shape of device 1, and threaded through the locking receptacles 22 on the external tines which extend radially away from the general cylindrical shape of the device 1, as shown in FIG. 2. By passing locking tines 20 through receptacles 22, locking tines 20 effectively link rings 6 and 10 to provide an important locking feature upon deployment of the device, as will be discussed below. The external tines 18 that contain the locking receptacles 22 may be formed wider than the external tines 18 that do not contain locking receptacles, to compensate for the loss of surface area due to formation of the locking receptacle, as well as to provide a greater surface area against which the respective locking tines 20 are forced.

Figure 1B:
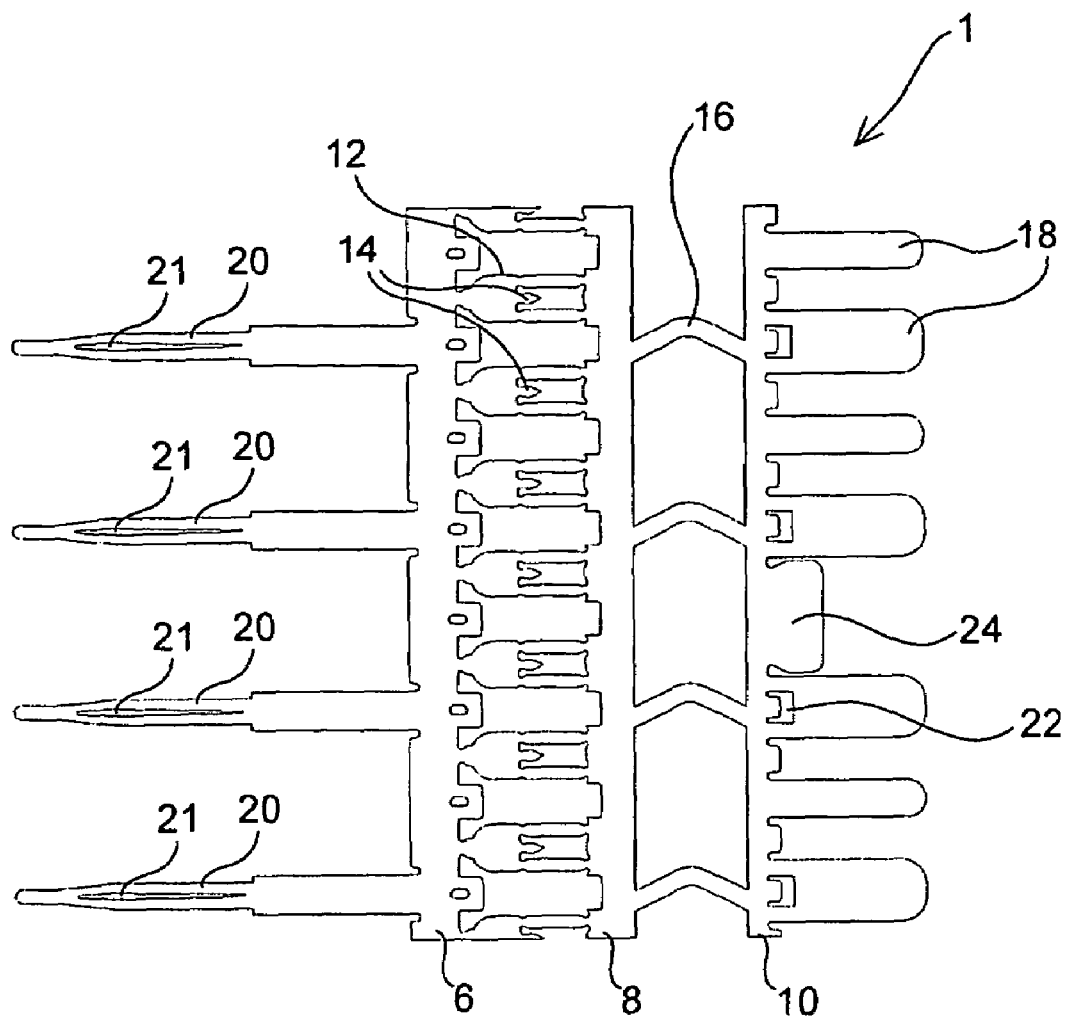
FIG. 1B shows a flat pattern of another anastomosis device for use according to the present invention.

FIG. 1B shows another example of a flat pattern of an anastomosis device 1 according to the present invention, before any forming of the device has been performed. As is the case with the device 1 in FIG. 1A, device 1 (FIG. 1B) is generally formed integrally, as an annular structure (e.g., see FIG. 2), such as by laser cutting from tubular stock, for example, although it would be possible to cut or stamp a planar structure from a sheet of material and then weld or otherwise fix the device in its annular form. The device 1 in FIG. 1B is substantially similar to that of the device of FIG. 1A, and therefore all of the description of the features will not be repeated here, but a focus on the main differences between the devices will be described. It will be readily apparent that a fewer number of support struts 16 are provided in the device of FIG. 1B. By providing a fewer number of support struts 16 it is believed that a tendency of the struts 16 to buckle outwardly or inwardly is greatly reduced. In any of the designs described herein, a deployment tool (described below) tends to prevent buckling inwardly, but with the currently described design, the locking tines 20 are much more effective in preventing outward buckling of the support struts 16.

Another significant difference in the device of FIG. 1B is that the graft tines 14 formed in buckling struts 12 are formed to have a shorter length than those in the device of FIG. 1A. For example, graft tines 14 in the embodiment of FIG. 1B are generally formed to have a length less than about 0.25 mm so that it will be impossible to pierce the entire wall of the graft and extend out the everted side of the graft wall. The shorter graft tines 14 cannot extend all the way through the wall of the graft when it is mounted thereon, and, accordingly, the graft tines 14 do not extend from the everted wall of the graft when mounted. When the device 1 and graft 3 are deployed to form the anastomosis, the metal tines are not exposed in the completed anastomosis, as will be shown and described as the description proceeds. The graft tines 14 of the device in FIG. 1A, on the other hand, are of a length which can and often do extend through the wall of the graft.

Locking tines 20 include weakened sections or cutouts 21 which assist in the preferential bending of the tines in the locations of the weakened sections during the locking phase of deployment of the device. This helps ensure that the locking tines bend into the configuration for which they have been designed, thereby providing the intended secure locking function. Weakened section 21 can be formed by elongated slots, as shown in FIG. 1B, or a series of holes, as shown in FIG. 2, or other shapes and configurations of cutouts designed to weaken the intended sections of the tines where it is desired to have the bending of the tines begin during the locking phase.

FIG. 2 shows device 1 in its three dimensional configuration, which may be formed by shaping and welding a flat configuration as described above, but is preferably formed by directly cutting it from tubular stock, such as by laser cutting, for example.

Figure 3:
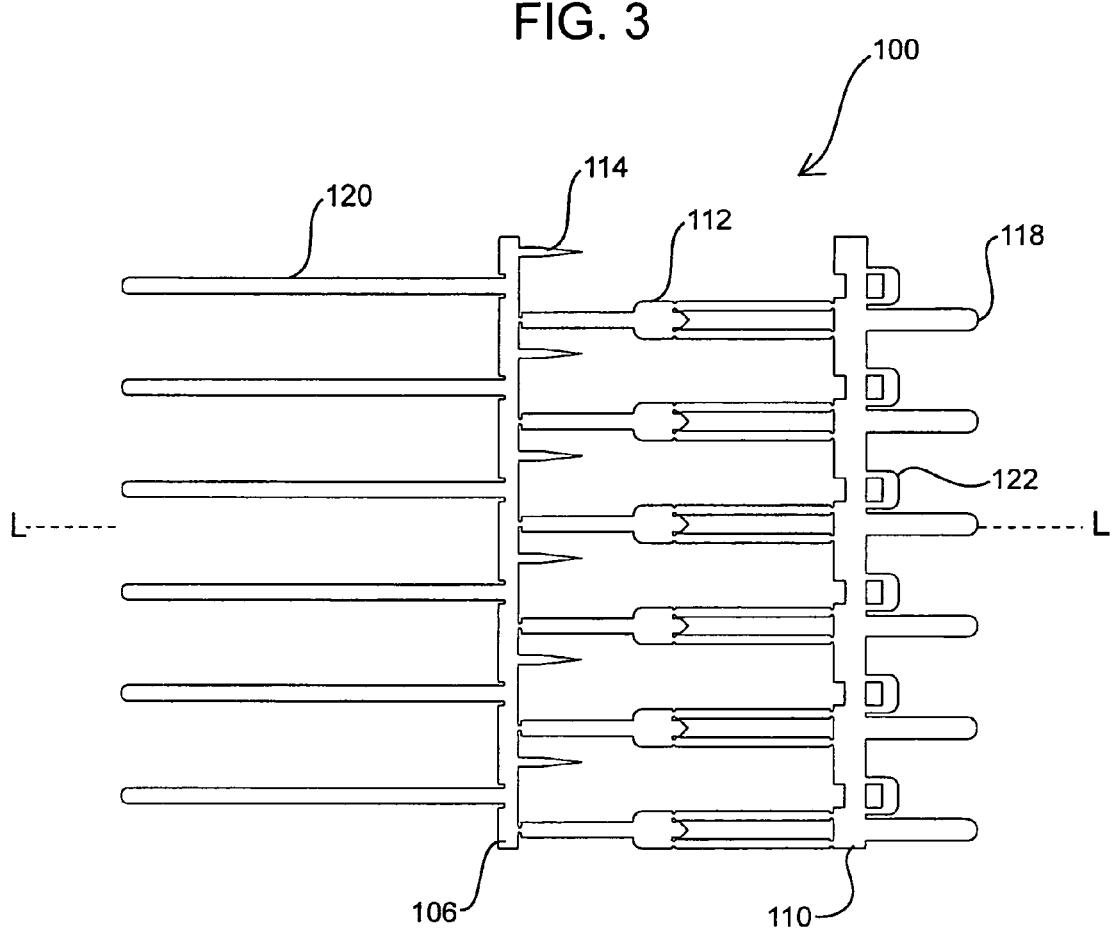
FIG. 3 shows a flat pattern of another example of an anastomosis device for use according to the present invention.

FIG. 3 shows a flat pattern of another example of an anastomosis device 100 according to the present invention. Like device 1, device 100 is generally formed integrally, as an annular structure, for example, by laser cutting from tubular stock, although it would be possible to cut or stamp a planar structure from a sheet of material and then weld or otherwise fix the device in its annular form, or otherwise cut the pattern from tubular stock. Device 100 may be made from the same materials as described with regard to device 1.

In this arrangement, only two rings 106, 110 are provided to form the basic cylindrical structure of device 100. Buckling struts 112 join rings 106 and 110 and are generally equally spaced around the circumferences of the rings 106 and 110 to form a buckling portion of the device 100. Buckling struts 112 are bent outwardly from an outer surface of an imaginary cylinder defined by rings 106 and 110, to make the buckling portion more susceptible to collapse upon exertion of compressive forces along the longitudinal axis of device 100 and to direct the buckling motion of struts 112 in an outward direction so as to effectively increase the outside diameter of the buckling portion upon buckling. Graft tines 114 extend from ring 106, and are bent to positions substantially perpendicular to the longitudinal axis of device 100 during forming, to position them for anchoring the end of a graft, as discussed further below.

External tines 118 extend from ring 110 and are bent substantially perpendicularly to the longitudinal axis L of device 100 during forming. Locking tines 120 extend from ring 106 at substantially evenly spaced locations about the circumference of ring 106. Locking tines 120 have a sufficient length to span the remaining length of device 100 when they are folded over by one hundred and eighty degrees during forming. Locking receptacles 122 are formed adjacent external tines 118 and extend from ring 110 in alignment with locking tines 120, and are bent substantially perpendicularly to the longitudinal axis L of device 100 to allow locking tines 120 to pass therethrough during formation of the device. The locking tines 120 are bent over to the external side of the general cylindrical shape of device 100, and threaded through the locking receptacles 122. By passing locking tines 120 through receptacles 122, locking tines 120 effectively link rings 106 and 110 to provide an important locking feature upon deployment of the device, as will be discussed below. External tines 118, along with the locking tines, when they are bent over during the locking procedure, form contact surfaces by which device 100 applies pressure to the external surface of a vessel (e.g., external wall of the aorta) to which a graft, held by device 100, is being joined. Although not shown, an alignment tab 124, such as shown in the device 1 may be included on device 100, either adjacent to, or in place of one of external tines 118, to control proper alignment of device 100 when loaded on a deployment instrument.

Deployment Instrument

Figure 4:
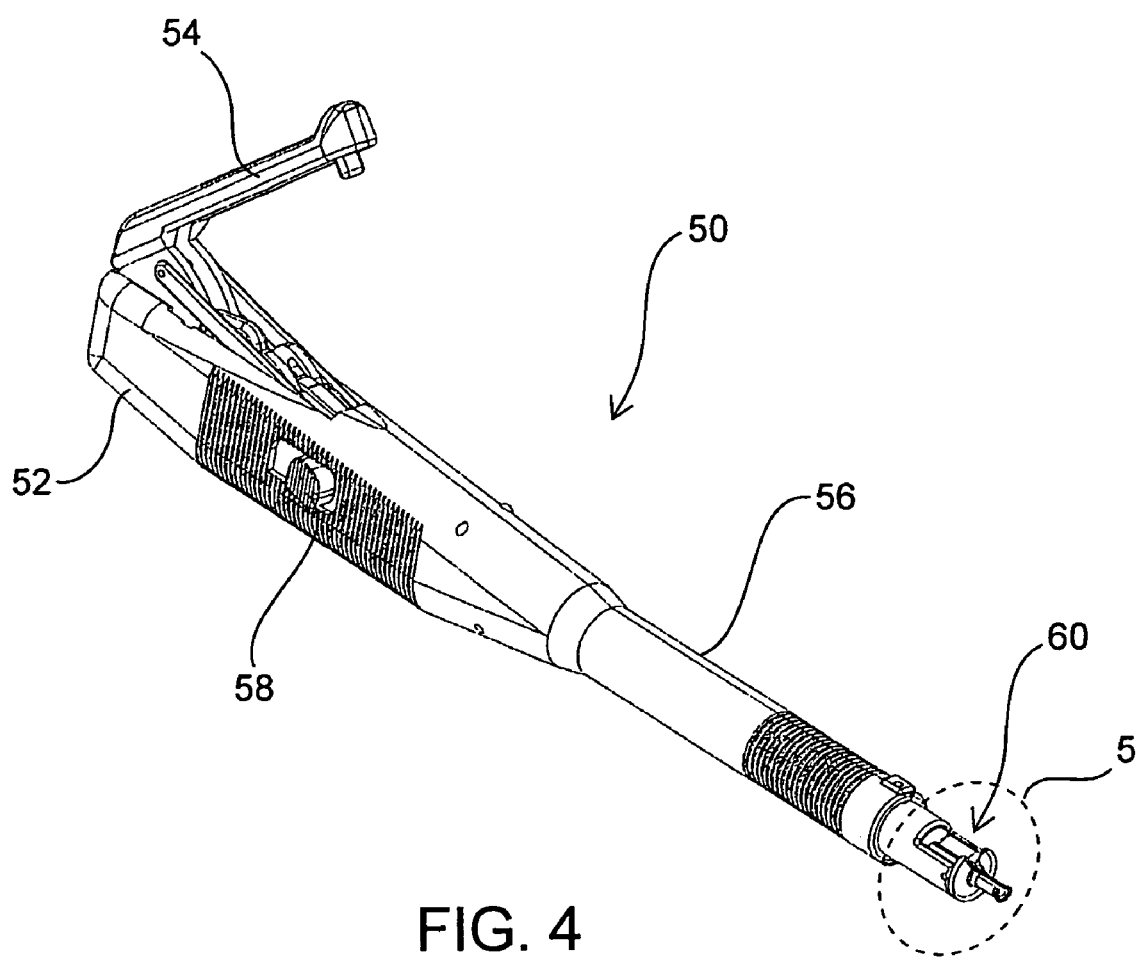
FIG. 4 is a perspective view of a deployment instrument used in deploying anastomosis devices according to the present invention.

FIG. 4 is a perspective view of a deployment instrument 50, which is configured to receive and deliver an anastomosis device in performance of an end-to-side anastomosis. Generally speaking, instrument 50 includes a main body or handle portion 52, which is configured to be hand held by the operator. A distal tip portion 60 of instrument 50 is configured for receiving, holding and deploying an anastomosis device 1,100 according to the present invention. A driving lever or trigger 54 is actuated by squeezing to move it towards handle 52 to perform a deployment of an anastomosis device. A long, slender extension portion 56 separates the distal tip portion 60 from the handle 52 by a sufficient distance to adapt the device to be employed in vary small spaces and even endoscopically in some situations. The handle 52, trigger 54 and extension 56 may all be formed of a structurally rigid polymer, such as ABS plastic or other materials which are sufficiently rigid and biocompatible.

Figure 5:
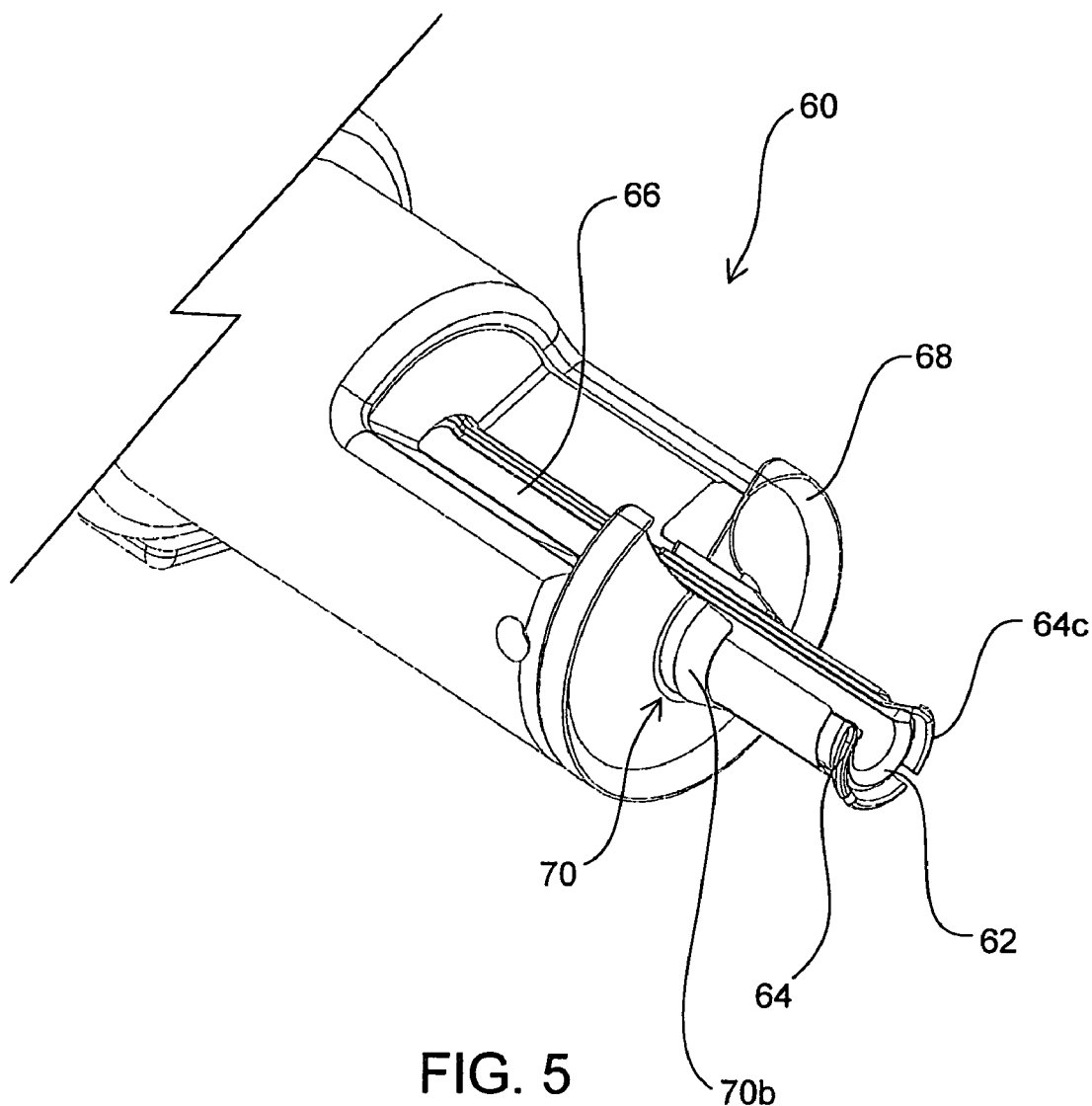
FIG. 5 is an enlarged view of the distal tip portion of the instrument shown in FIG. 4.

FIG. 5 is an enlarged view of the distal tip portion 60 of instrument 50, which is enlarged from the section delineated by phantom circle 5 in FIG. 4. Distal tip portion 60 includes an assembly of substantially cylindrically shaped tubes, which are concentrically arranged for receiving, holding and deploying an anastomosis device. Of course, those of ordinary skill in the art would recognize that the assembly of tubes could be formed with other conforming cross-sectional shapes, for example, elliptical, oval or other cross-sectional shape tubes could be substituted. The outside diameter of the arrangement is slightly less than the inside diameter of a device 1,100 for which it is designed to receive and deploy. For example, a clearance of about 0.002" may be provided between the inside diameter of the clip 1, 100 and the outside diameter of the arrangement. Such a design allows the device 1,100 to be freely slid over the tube portions when in the loading configuration, while at the same time not allowing so much clearance as to allow the device to become misaligned. Because of this fairly close tolerance requirement, instruments 50 having varying distal portion outside diameters are manufactured to match the inside diameters of the various device sizes that may be needed. As discussed above, the device sizes may vary in the range of about 3.0 mm to about 7.0 mm inside diameter, which necessitates the provision of a series of delivery instruments 50 to accommodate the size variations.

Figure 6:
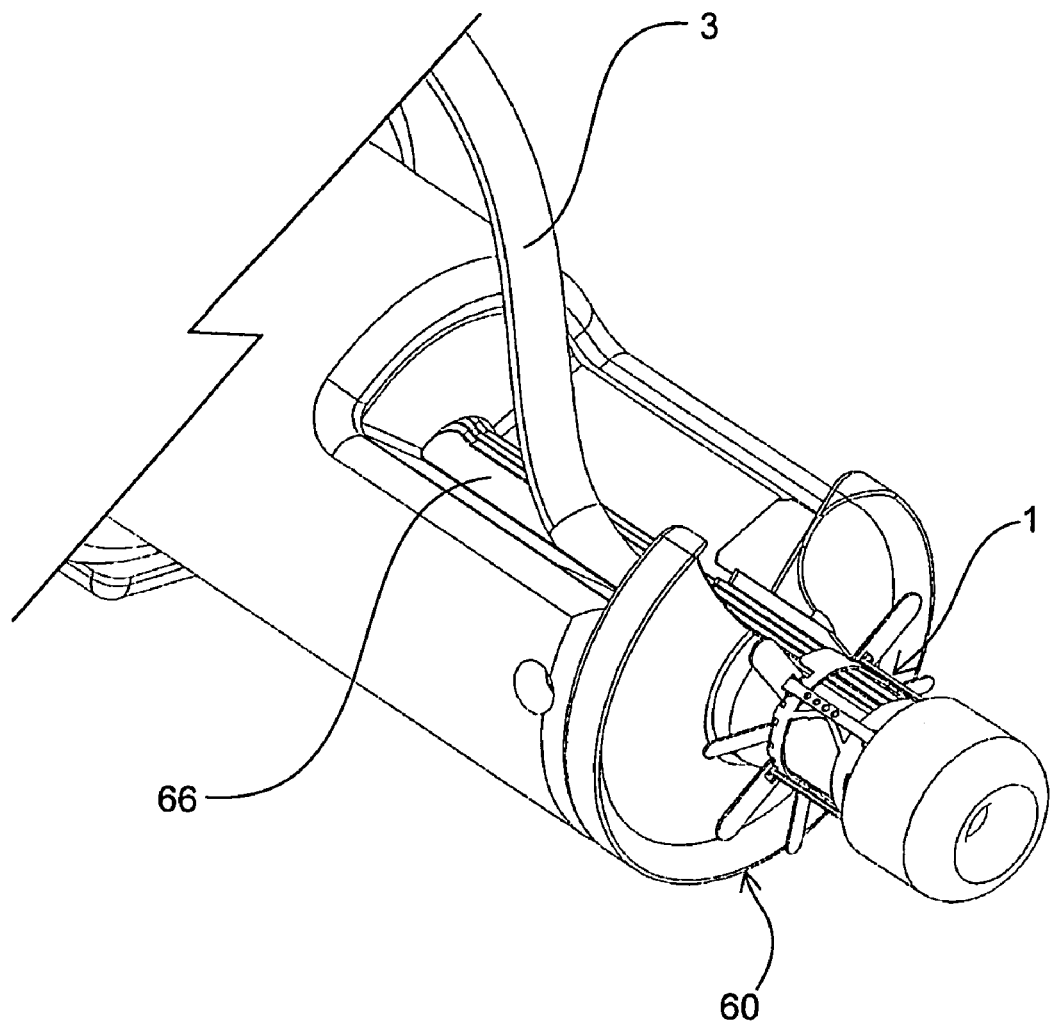
FIG. 6 shows a graft having been loaded on a device and captured by a deployment instrument according to the present invention.

Each of the concentric tubes is provided with a longitudinal slot so as to define a channel 66 in the top of the arrangement that allows a graft (attached to a device 1, 100) to extend externally of instrument 50, and to render the cross-sectional views of the tubes to appear somewhat "C-shaped". Advantageously, this feature allows a graft to be side fed into instrument 50 and also does not require that both ends of the graft be free in order to perform an anastomosis according to the invention. For example, FIG. 6 shows a graft 3 fixed to a device 1 and the device having been captured on distal portion 60 of instrument 50 for performing a proximal anastomosis of graft 3 with an aortic wall. In this case, an internal mammary artery was used as the graft and so the opposite end of the graft (not shown) is still connected to the vasculature of the patient. Further, this feature would also allow the distal anastomosis of a graft initially having two free ends (such as a saphenous vein graft as one, non-limiting example) prior to the proximal anastomosis of the graft.

Currently known procedures typically require the proximal anastomosis to be performed before the distal anastomosis is performed. This is disadvantageous for at least two reasons. One reason is that surgeons are currently trained to perform the distal anastomosis prior to performing the proximal anastomosis. A second reason is that, depending upon the location of the coronary artery which is being bypassed, it is very frequently necessary to move the heart out of its natural position, such as by elevating it out of the chest cavity to provide access to the site where the anastomosis is to be performed. If the proximal anastomosis must be performed first, this makes it very difficult, if not impossible to accurately measure the length of graft that will be needed to properly perform the distal anastomosis. This is so, because in the displaced position, the heart is not fully perfused, and therefore any measurements made at this time are almost certain to be inaccurate, as the actual distance between proximal and distal anastomosis sites will change when the heart is returned to its natural position and becomes fully perfused, thereby enlarging somewhat. The current invention allows the distal anastomosis to be performed first, after which the heart can be properly positioned and an accurate assessment of the graft length needed can be made before performing the proximal anastomosis.

Therefore, it is often advantageous to perform the distal anastomosis prior to the proximal anastomosis in a cardiac bypass procedure as it is much easier to gauge the correct length to which the graft needs to be cut when the distal anastomosis is performed first since the heart will be normally loaded with blood and the surgeon can get a better approximation of where the locus of the proximal anastomosis will reside after completion of the procedure, which allows a more direct measurement of the length of the graft needed. As noted, the heart very often needs to be displaced to perform the distal anastomosis. By performing the distal anastomosis first, the heart can then be repositioned to its natural location and orientation, thereby making it much easier for the surgeon to visualize and directly measure or approximate the length of graft needed to reach the proximal anastomosis site. Since most surgeons traditionally perform the distal anastomosis first, even when using suturing methods, they will be more inclined to accept a procedure where distal anastomosis can be performed first.

Figure 7A:
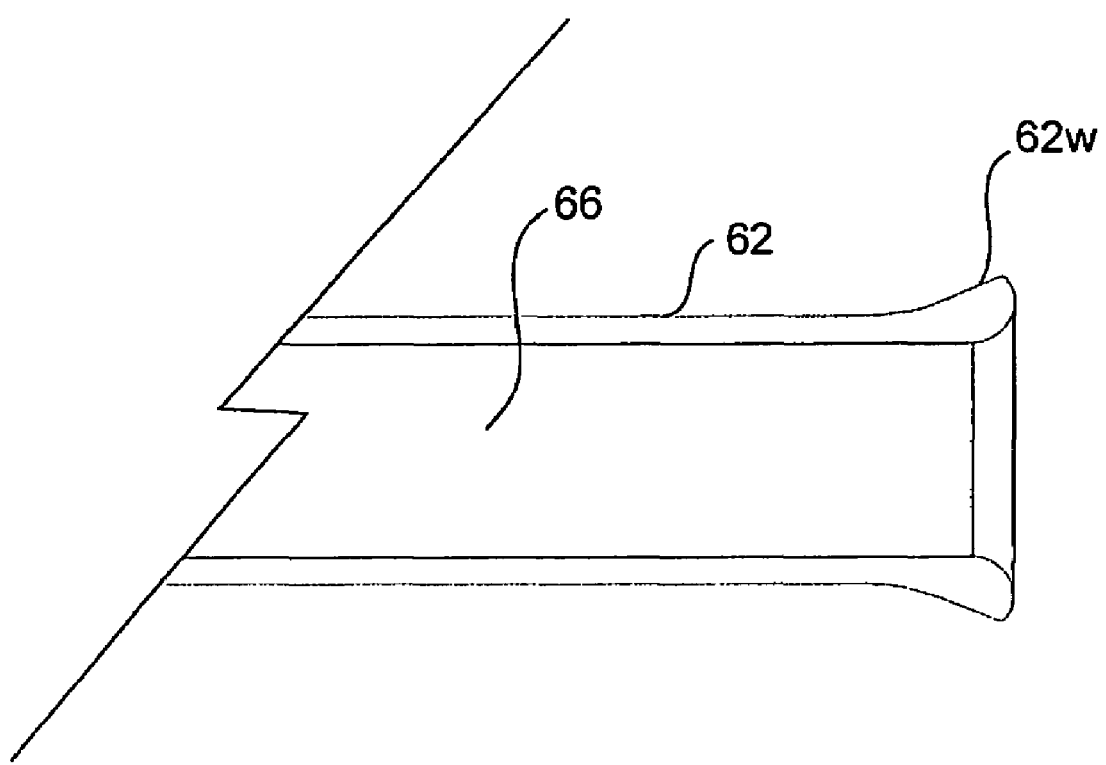
FIG. 7A is a partial top view showing the gradually increasing diameter of the distal end portion of the wedge tube of the deployment instrument.
Figure 7B:
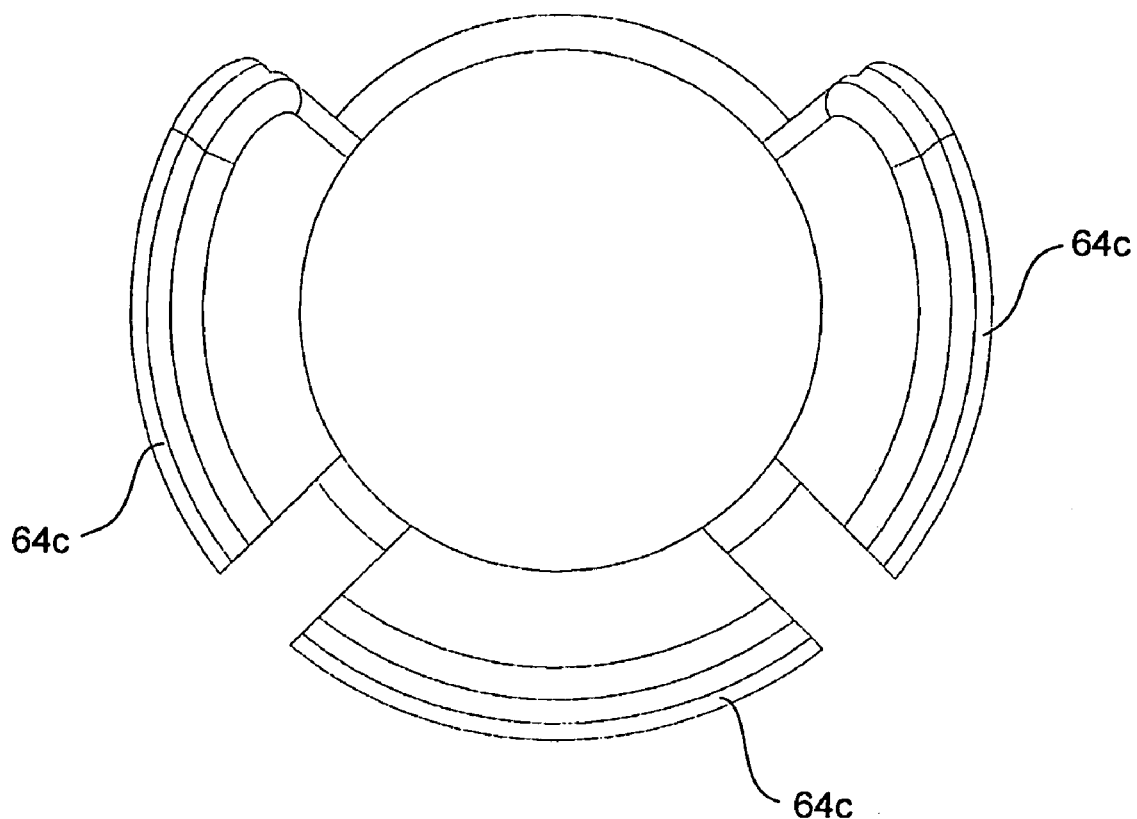
FIG. 7B is an end view of the expandable catch cam members at the distal end portion of the catch cam tube.

The concentric tube arrangement includes a wedge tube 62 concentrically surrounded by a catch cam tube 64, with these tubes arranged for relative sliding movement with respect to one another along their longitudinal axes. A release tube 65 is concentrically arranged over catch cam tube 64, and is relatively fixed to wedge tube 62 so that it slides relative to catch cam tube 64 when wedge tube 62 is slid relative to catch cam tube 64. The wedge tube 62, catch cam tube 64, and release tube 65 operate in conjunction with other features of the instrument 50 to perform the functions of capturing an anastomosis device 1,100; buckling the device; locking of the device; and finally releasing the device from the distal portion 60 of instrument 50. An anastomosis device is securely mounted or loaded onto the distal portion 60 of the instrument 50 by way of the capture function. The wedge tube 62 includes a flared or wedged end portion 62w that has a generally increasing outside diameter as shown in FIG. 7A. Catch cam tube 64 has an inside diameter that is freely slidable over the outside diameter of the non-flared portion of wedge tube 62, and is split or slotted at its distal end to form a plurality of expandable fingers or catches 64c (e.g., three are shown in the end view of FIG. 7B, although 1, 2 or 4 or more could be formed).

Figure 7C:
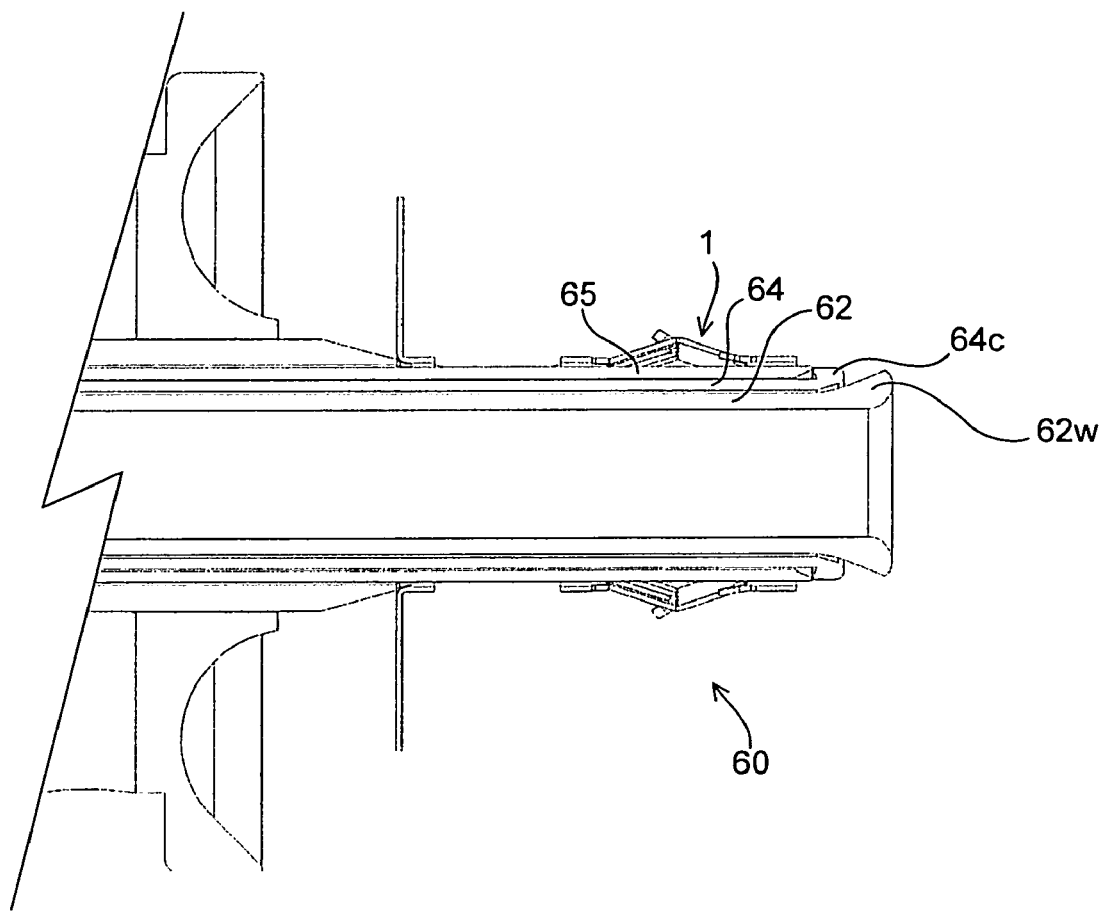
FIG. 7C shows the interaction between the distal end portion of the wedge tube the catch cam members of the catch cam tube during a capture procedure for fixing an anastomosis device on the deployment tool.
Figure 7D:
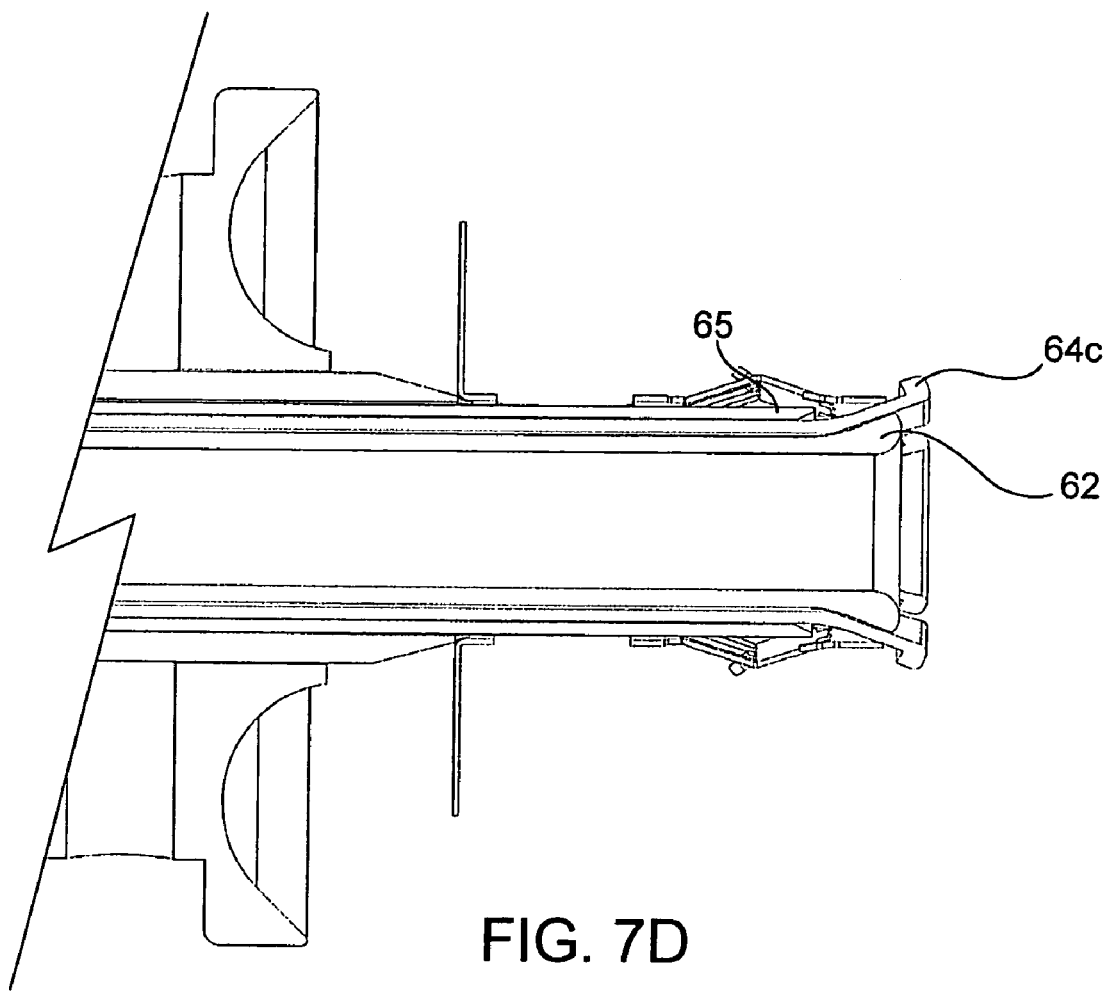
FIG. 7D shows an anastomosis device 1 having been captured on a deployment tool according to the present invention.

FIGS. 7C-7D show the interaction between wedge tube 62, catch cam tube 64 and release tube 65 during a capture procedure for fixing a device 1,100 on the distal portion 60 of the deployment instrument 50. It is contemplated that the capture, compression and release functions described herein could be accomplished by a device as described, but which lacks a release tube 65 as described. However, it is has been found that the instrument 50 operates more smoothly and reliably with the release tube 65 for reasons described below. Initially, a device 1,100 is slid over the concentric tubes 62,64 when the instrument is in the neutral or loading position as shown in FIG. 7C, such that the wedged end 62w of wedge tube 62 extends beyond the catch cam tube 64 and does not make contact with catch cams 64c. The release tube 65 surrounds the catch cam tube 64 in this configuration and ensures that the catch cam members 64c are positioned in their fully retracted configurations. The deployment device 50 is placed into the neutral position by advancing a pin or button actuator 58 (see FIG. 5) located on the side of handle 52. Advancement of the button or pin 58 pushes a central shaft that is connected to wedge tube 62, which advances wedge tube 62 so that the wedge portion 62w extends beyond catch cams 64c and therefore does not make contact with them, allowing the catch cams 64 to retract to a resting configuration in which the outside diameter of the end of the catch cam tube 64 (formed by catch cams 64c) is smaller than the inside diameter of a device 1,100 to be loaded thereon. Thus, the catch cam tube is in a relaxed or retracted configuration and even the catch cams have a smaller outside diameter than the inside diameter of the device 1,100 to be captured. For this reason, device 1,100 is freely slidable over the tubes 62,64,65.

Device 1,100 may include an alignment tab or tine 24 extending from ring 1,100 which is bent over, radially inward of the device into an orientation substantially perpendicular to the longitudinal axis of the device L during forming. Device 1,100 is aligned with instrument 50 by sliding alignment tab 24 in channel 66. This alignment ensures that each of the locking tines 20,120 will be properly aligned so as to be contacted by device lock 68 during the locking operation described below. The device 1, 100 is slid onto the distal portion until it makes contact with stop member 70. Stop member 70 is fixed with regard to handle 52 of device 50. Stop member 70 may include a beveled portion 70b, which provides a ramping surface against which device 1,100 comes to rest. In this way, stop member not only correctly positions device 1,100 in a longitudinal position along the distal portion 60, but also performs a centering function to keep device 1,100 properly centered on the distal portion 60 of deployment device 50.

Once device 1,100 is properly positioned and abutted against stop member 70, pin or button 58 is released, and wedge tube 62 is spring loaded so as to be drawn back with respect to catch cam tube 64, such that wedge portion 62w slides against and contacts catch cams 64c, radially expanding them to assume a larger outside diameter, as shown in FIG. 7D. At the same time, release tube 65, which is linked to wedge tube 62, retracts so that it no longer prevents the expansion of the catch cams 64c. Catch cams 64c, when in the expanded or deformed position, form a larger outside diameter than the inside diameter of device 1,100 and therefore capture device 1,100 on the distal tip portion 60 since device 1,100 is prevented from sliding off distal tip portion by the hooked configurations of catch cams 64c. Device 1 is securely held by the abutment of ring 10 against stop member 70, and by contact of ring 6 by catch cams 64c.

FIGS. 8A-8D are views of the internal components of deployment device 50 which link trigger 54 with various components at the distal end portion 60 of device 50 for performing the capture, buckling, locking and release functions during performance of an anastomosis.

Figure 8A:
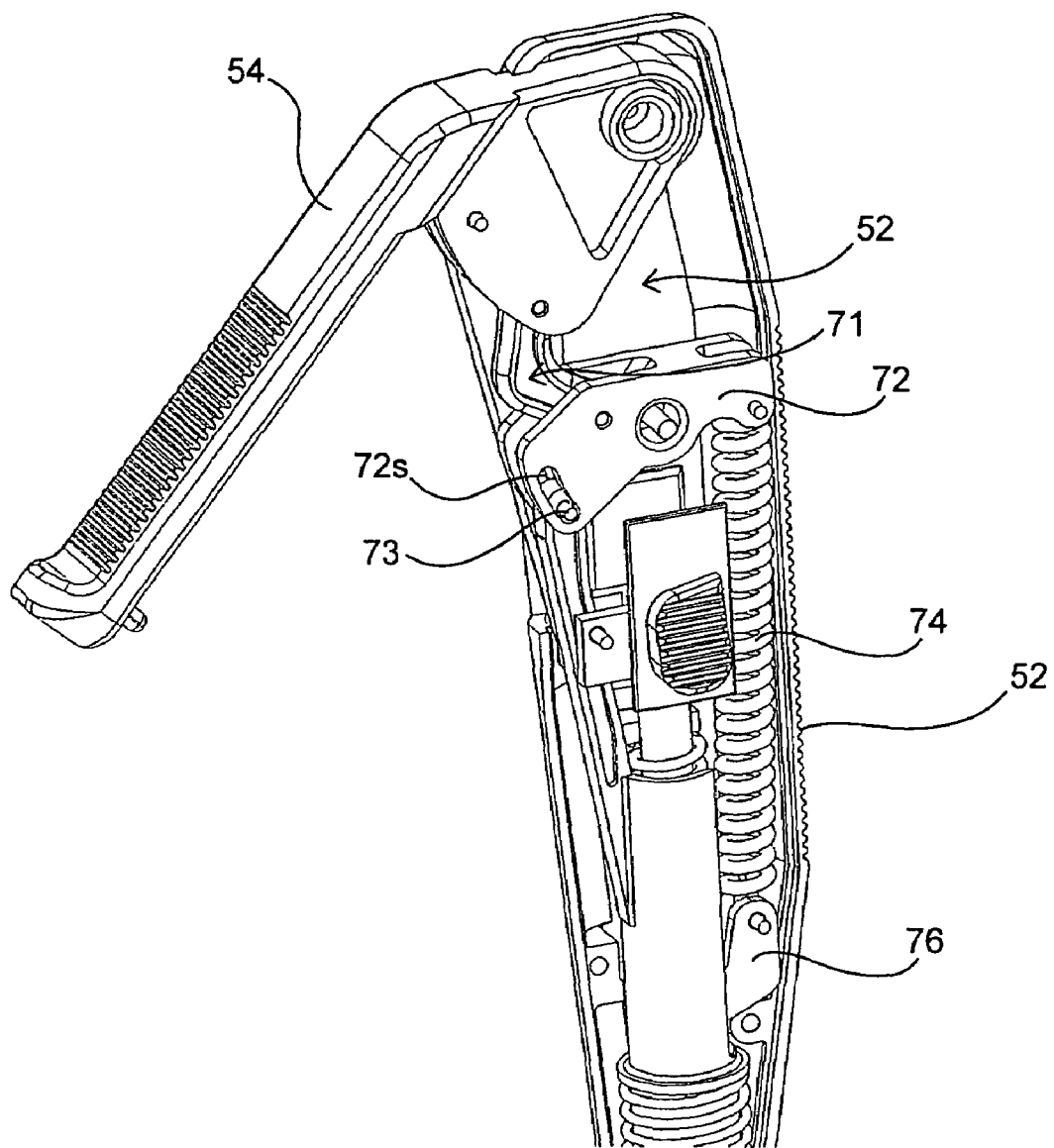
FIG. 8A shows a partial view of a proximal end portion of a deployment tool according to the present invention.
Figure 8B:
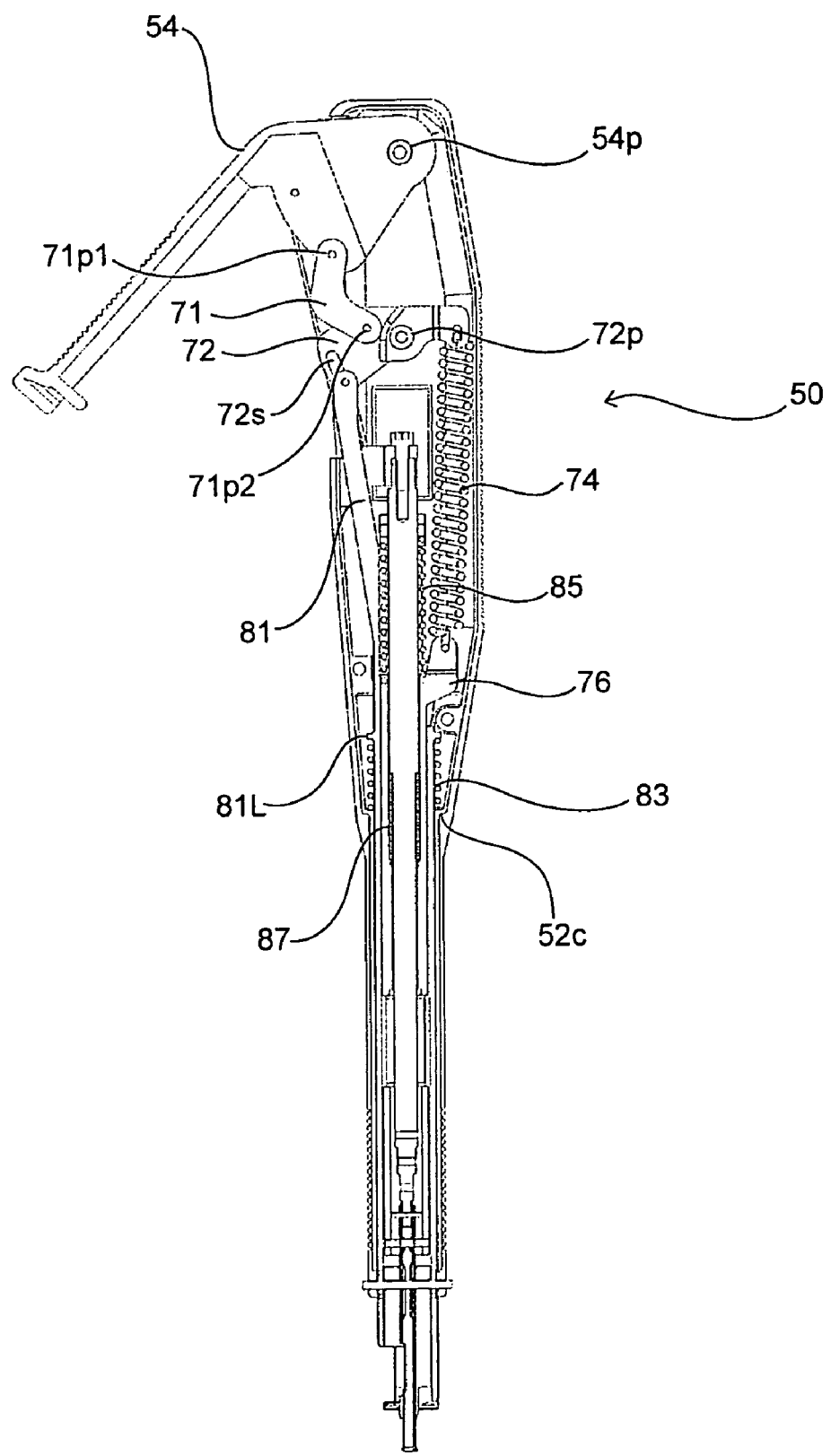
FIG. 8B shows an exposed view of working components in the mechanism for operating a deployment tool according to the present invention.
Figure 8C:
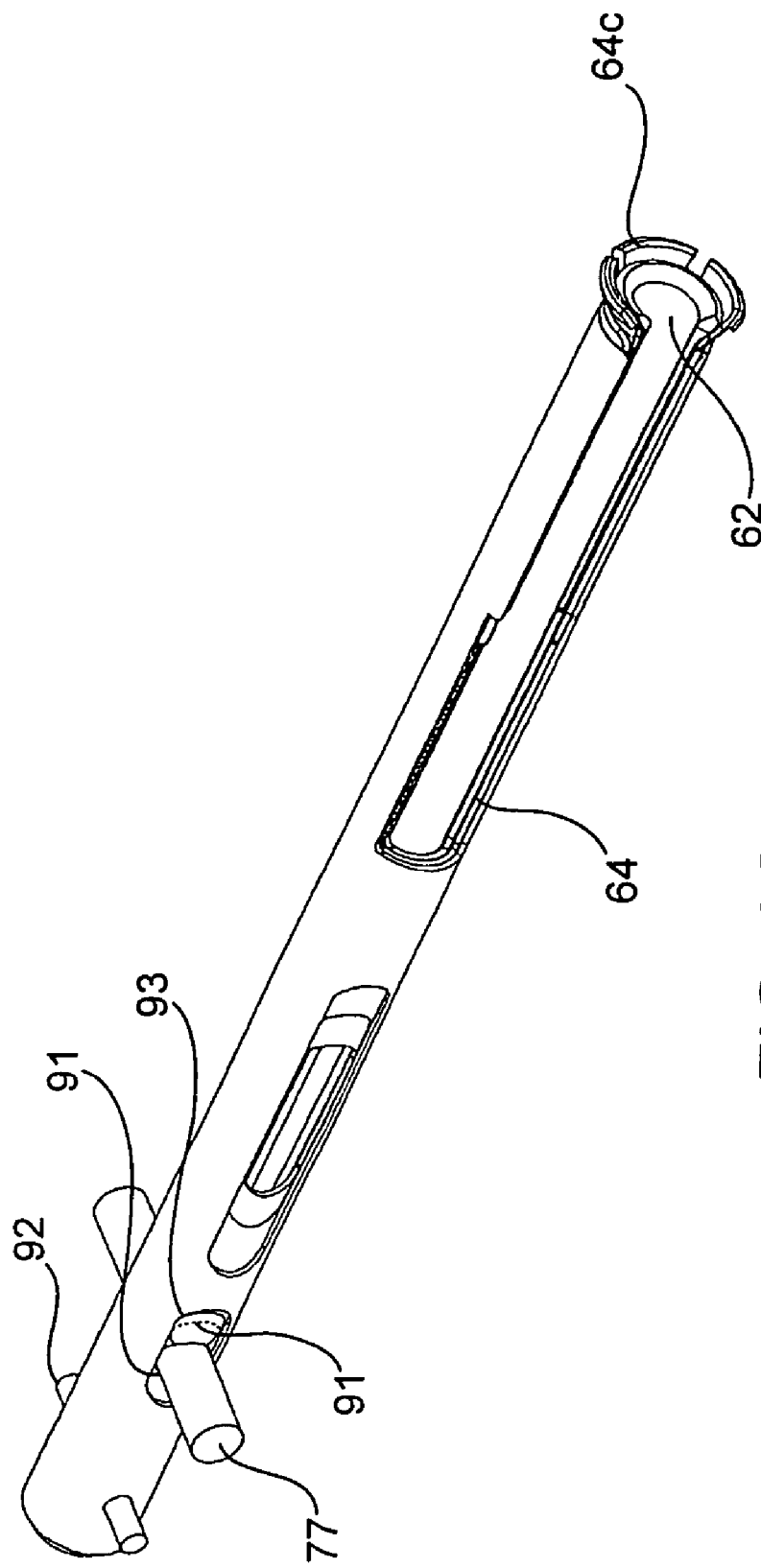
FIG. 8C shows a partial assembly of a deployment tool according to the present invention.
Figure 8D:
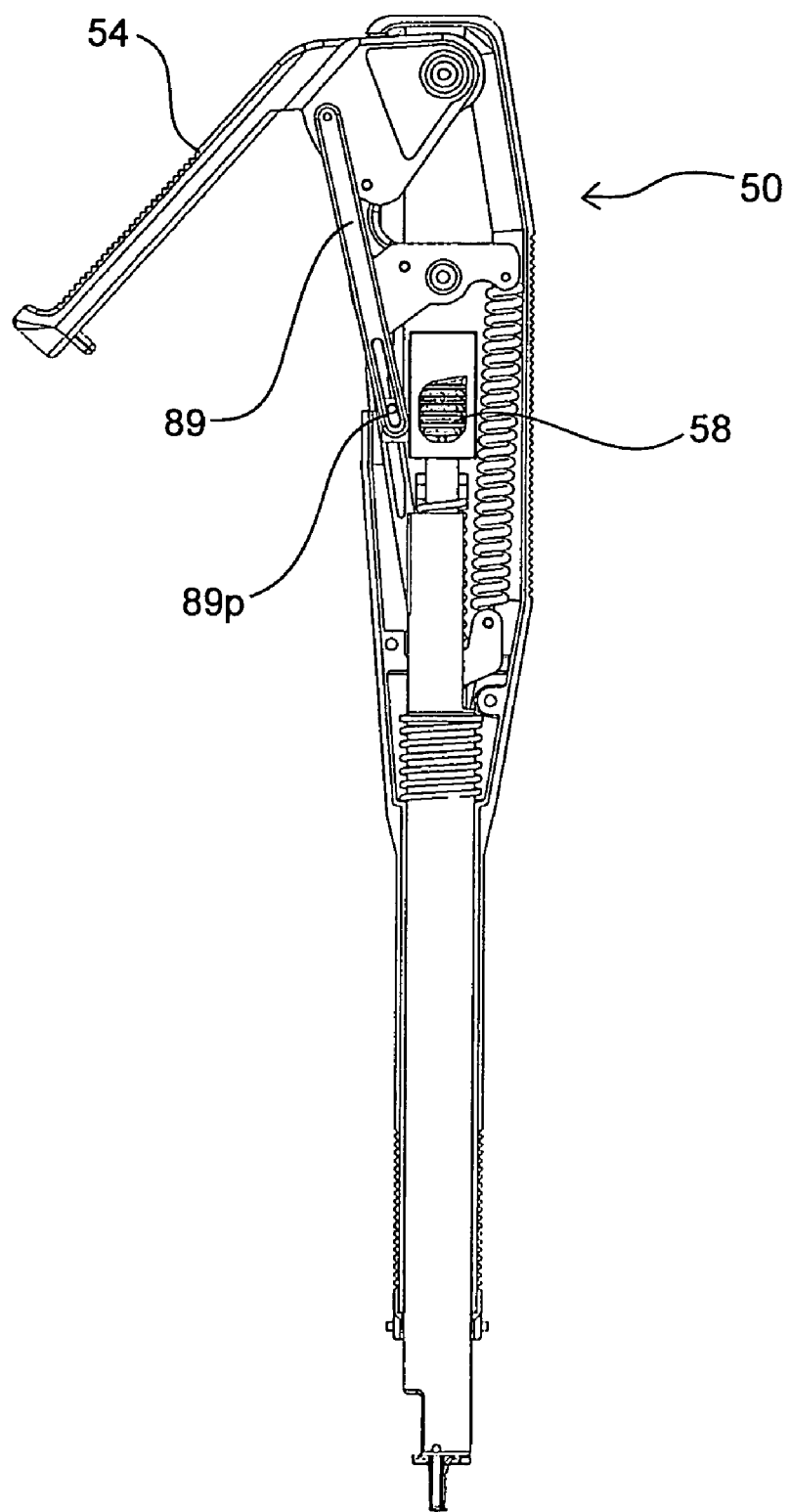
FIG. 8D shows another exposed view of working components in the mechanism for operating a deployment tool according to the present invention.

Referring to the proximal end portion view of FIG. 8A, a four bar linkage arrangement is provided in the form of trigger 54, trigger link 71, rocker 72 and the handle 52 of device 50. As the trigger 54 is pulled or pressed toward handle 52, it drives trigger link 71, which in turn drives rocker 72 in rotation toward the distal end of device 50, causing a retraction of catch cam tube 64 through extension spring 74 which is connected to compression slider 76 that connects through the catch cam with pin 77 (see FIGS. 8B and 8C), in a direction toward the proximal end of device 50. At the same time, stop member 70 remains fixed relative to device 1,100, resulting in a compression force being applied to device 1,100 as catch cam tube 62 retracts. Wedge tube 62 is spring loaded with respect to catch cam tube 64 by way of a compression spring extending between pin 92 (which interlinks wedge tube 62 and release tube 65) and compression slider 76 (which is connected to catch cam tube 64 in the manner described above), so that, in their resting positions, wedge tube 62 is biased in extension relative to catch cam tube 64 which allows the catch cams 64c to relax or retract. A slot 91 is provided in the wedge tube 62, as shown (in phantom) in the isolated assembly of FIG. 8C. A longer slot 93 is formed in the release tube 65. Pin 77 goes through slot 91 and is retained by a through hole in catch cam tube 64 which forms a press or friction fit with pin 77 as it is positioned through slot 91 and the hole. In the view shown in FIG. 8C, the wedge tube 62 has been retracted so as to expand catch cams 64c and pin 77 is positioned against the proximal end of slot 91. This occurs during the retraction by compression slider 76, which overcomes the compression spring, thereby deforming it under a compressive load, and allowing wedge tube 62 to move proximally with respect to catch cam tube 64 until pin 77 abuts the proximal end of slot 91. By this arrangement, further retraction for compression of a device 1,100 results in the catch cam tube 64 and wedge tube 62 sliding proximally in unison, to ensure that the catch cams 64c remain in the expanded configuration, thereby ensuring that the capture of device 1, 100 is maintained during compression.

Pin 77 can slide in the slot 91 on reverse motion to allow the catch cam catches 64c to retract as the wedge 62w extends distally of them, then the pin 77 contacts the distal (opposite) end of the slot 91 so that the catch cam tube 64 and wedge tube 62 again move together in any further distal sliding. That is, when the tension on spring 75 is relieved so that it no longer draws against compression slider 76, as catch cam tube returns to the reset position, the compression spring between pin 92 and compression slider 76 extends to release its compression, thereby sliding wedge tube 62 distally with respect to catch cam tube 64 until pin 77 contacts the distal end of slot 91. This biasing by the compression spring maintains the catch cams 64c in their retracted configuration in the reset position of device 50. During the compression motion, as the catch cam tube 64 and the wedge tube 62 are proximally slid in unison, the catch cams 64c and stop 70, as a result, compress device 1,100 so that initially, the buckling section of the device buckles. Thus, in the case of device 1, the buckling section between rings 6 and 8 collapses or buckles first with struts 12 moving radially outwardly during buckling, as described above, to form a mushroom-shaped configuration.

As the trigger 54 continues further in its travel toward the body 52, the struts 16 of the strut section begin to collapse as the catch cam tube 64 and wedge tube 62 further advance toward stop 70. The collapse of the strut section is accomplished to draw a graft and vessel together during an anastomosis procedure with a sufficient force to form a successful seal between the two, while not compressing the anastomosis with too great a force to potentially cause damage to the living tissue. As such, the collapse of the strut 16 draws the rings 8 and 10 closer together, which effectively also draws the buckled struts 12 closer to ring 10, thereby compressing the tissues which are held there between during an anastomosis procedure.

Extension spring 74 interconnects rocker 72 with compression slider 76, which retracts the catch cam tube as described above. Extension spring 74 acts as a force limiter during the compression/buckling stage. Extension spring 74 has a preset load at which it begins to expand. For example, extension spring may be designed so that the coils do not begin to expand or separate until a load of about 20 pounds has been reached. The effect achieved by this is that the catch cam tube will continue to be retracted, and therefore continue to compress/buckle device 1,100 until such time as a 20 pound load is exerted upon the extension spring 74, or until rocker 72 goes over center and reverses direction (via the four-bar linkage. When an imaginary straight line connecting the two pivot points 71p1 and 72p2 becomes parallel with an imaginary straight line interconnecting trigger pivot 54p and rocker pivot 72p, the four-bar linkage is considered to be at "center". Further driving by the trigger 54 causes the linkage to go over or beyond center, which drives rocker 72 into a reverse rotation. The preset load on the extension spring may be reached or achieved when the buckled struts 12 (which carry an everted graft end) and external tines 18 compress the tissues there between sufficiently to form a leak tight seal.

Once the predetermined force or load is reached, extension spring 74 begins to extend, so that no further driving/retraction of the catch cam tube 64 can occur and device 1,100 is therefore compressed no further. For example, accounting for about 8-9 pounds required to buckle a device 1,100, and the force needed to counteract a reset spring 85, which abuts against the handle 52 and the compression slider 76 to exert a return or resetting biasing force to reset the catch cam when no force is being applied to it by spring 74 of the deployment device, an extension spring 74 having a preset load of about 20 pounds translates to a compression force of about 3-4 pounds which is actually applied to the tissues compressed by device 1,100 when spring 74 begins to extend. Of course the present invention is not limited to a final compression force of about three to about four pounds, as slightly less force may be applied (e.g., about one to three pounds) or slightly greater force, so long as it is not so great as to cause tissue damage.

With the force-limiting feature, device 1, 100 is not collapsed to a predefined length. Rather, it is collapsed until a predefined buckling force is achieved. Because of this, device 1,100 can reliably seal an anastomosis of a graft to vessels of varying wall thickness, wherein the compressive force for connecting a graft to a thin-walled target vessel (e.g., aorta) is substantially the same as the compressive force established when connecting a graft to a thick-walled vessel (e.g., an aorta having a relatively thicker wall than the previous one). That is, instead of forcing the device 1,100 into a particular thickness, it is adjustable to various wall thicknesses, and is controlled to be collapsed only to a thickness that will achieve a predetermined amount of compressive force on the site of the anastomosis. Practically speaking, this means that the thickness of the gap in which device 1,100 compresses the graft and vessel will vary with the thickness of the vessel wall and graft wall, but will achieve substantially the same compressive force regardless of the thickness of the tissues being joined.

As the trigger 54 continues its motion toward the handle/body 52, after the buckling of device 1,100 has been accomplished, pin 73 reaches the end of slot 72s in rocker 72. Continued advancement of rocker 72 then drives lock driver 81 which is integral portion of (or may be connected to) device lock tube 81 (upon which the device lock 68 is fixed) at its distal end. As the device lock tube 81 is driven in a direction toward the distal end of deployment device 50, this motion drives device lock 68 toward device 1,100, while catch cam tube 64 and wedge tube 62 remain fixed with respect to device 1,100. Additionally, a lock spring 83 which abuts a ledge or shoulder 81L formed on device lock tube 81 at one end, and another ledge, abutment or shoulder 52L formed in handle 52, is compressed by the advancement of device lock tube 81 relative to handle 52. Stop member 70 is fixed with regard to handle 52, and therefore maintains its fixed position as device lock tube 81 and device lock 68 advance. The device lock 68 includes curved guide surfaces 68g which guide the ends of locking tines to be bent radially outward, with further advancement of device lock 68 bending the locking tines 20,120 over locking receptacles 22,122 and against external tines 18 or the wall of the graft (in the case of a design such as device 100). By bending the locking tines 20,120 over against locking receptacles 22,122, the locking tines secure the positions of rings 6 and 10 from being spread apart. This permanently sets the positions of the rings and the force applied thereby, preventing the device 1, 100 from expanding or unbuckling.

As the trigger 54 completes its travel toward handle 52, the reverse rotation of rocker releases the force between rocker 72 and device lock tube 81, which allows the biasing force contained in lock spring 83 to reset the tool. The locking driver (device lock) 68 is retracted back to its neutral starting position, thereby breaking contact with the locking tines 20,120. At the same time, the reverse rotation of the rocker 72 takes the load off spring 74 so that the biasing force of spring 85 drives the compression slider 76 and catch cam tube distally to their neutral positions. The wedge tube 62 is driven distally along with the catch cam tube 64. The motion of the trigger 52 going forward (i.e., toward the body of the tool) also drives wedge link 89, so that an end of the slot 89s in wedge link 89 abuts pin 89p connected to button 58, and then drives button 58 distally to further drive the wedge tube 62 in the distal direction so that the wedge portion 62w breaks contact with catch cams 64c, which, as a result, return to their relaxed or retracted positions, to define an outside diameter that is smaller than the inside diameter of the device 1, 100. This is the release position of the deployment tool, and allows the distal end portion 60 to be slid out from inside device 1,100, leaving device 1,100 undisturbed at the site of the anastomosis.

Although the catch cams 64c retract to a conformation that may be slid out from inside the device 1,100, it was discovered that there was still some potential for one or more of the catch cams 64c to catch on a ring or strut of the device 1,100 as the deployment tool 50 was being withdrawn. For example, if the device 1,100 was allowed to drop down on the distal end portion 60, this would leave a large gap between the deployment device end portion 60 and the bottom of the device 1,100, while the top portion of device 1,100 would contact the catch cam tube 64 and then be trapped by the catch cam 64c during an attempt to remove the deployment tool. To ensure that the deployment tool 50, and particularly a catch cam 64c does not catch on the device 1,100 during removal of the tool 50, a release tube 65 is provided, as shown in FIGS. 7C and 7D.

Release tube 65 concentrically surrounds catch cam tube 64 for sliding movement relative thereto, and also has a slot to match those of the catch cam tube 64 and wedge tube 62. Release tube 65 is linked to wedge tube 62, such as by a pinned interlink 92, so that it moves together with wedge tube 62 at all times. Thus, during the loading/capture of a device 1, 100, release tube 65 is retracted away from the catch cams 64c as wedge 62w is retracted into the catch cams 64c to expand them (as shown in FIG. 7D). This removes the release tube from the vicinity of the catch cams 64c allowing the catch cams 64c to more effectively capture the device 1,100.

During the release procedure, as the wedge tube 62 is pushed out from the catch cam tube 64, release tube 65 slides with wedge tube 62, so as to approximate the catch cams 64c of catch cam tube 64, as shown in FIG. 7C. Although FIG. 7C shows loading a device 1,100 onto the tool 50, the release tube 65, catch cams 64c and wedge 62 are positioned the same as when a release of the device 1,100 is being performed. Release tube 65 also may function to slightly compress the fingers of the catch cams 64c by a force opposite to that that is applied by the wedge tube when the fingers are expanded. Release tube 65 is dimensioned such that the external surface of the tube extends slightly higher than the extent of catch cams 64c. Therefore, when deployment tool 50 is removed from device 1, 100, even if the device 1,100 does drop down, it slides along the surface of release tube 65 and clears the catch cams 64c providing for a smooth removal of the deployment device.

Loading the Graft

A device 1,100 may be preloaded on a deployment tool, in the capture position described above, or may be provided separately. When provided separately, a graft may be loaded on the device 1,100 prior to capturing the device 1,100 with a deployment tool 50, or the device may be captured first by the deployment tool and the graft may then be loaded according to at least one of the following procedures for loading a pre-captured device. The graft need only have one free end, since the deployment device 50 is non-cannulating and can be side loaded by way of slot 66, as described above. Of course, grafts having two free ends may be loaded just as easily. Thus the graft may comprise an autologous artery or saphenous vein, or may be an allograft, or xenograft or of synthetic origin.

Figure 9A:
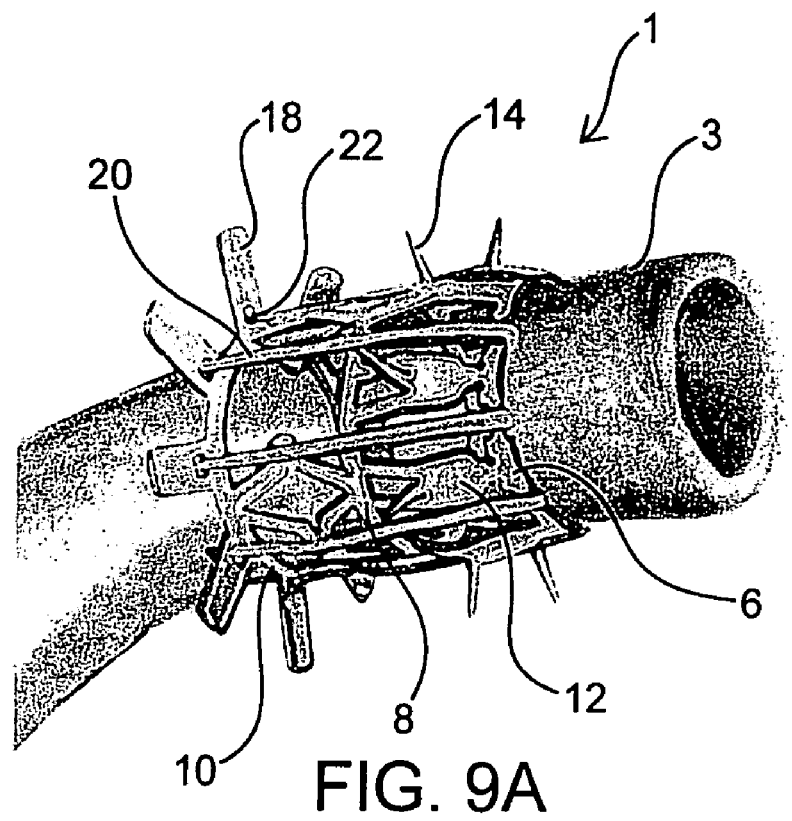
FIG. 9A is a perspective view of a graft vessel having been passed through the annular space defined by an anastomosis device according to the present invention.
Figure 9B:
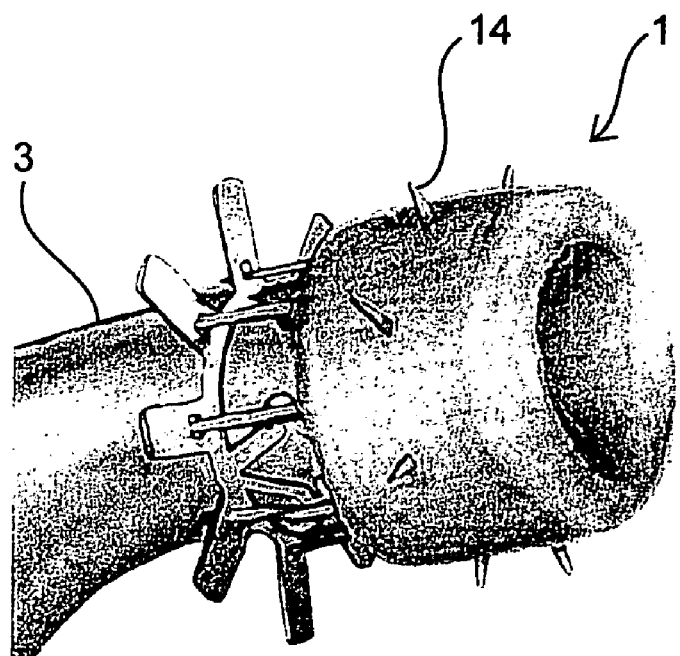
FIG. 9B is a perspective view of the graft vessel shown in FIG. 9A after further having been everted and pierced by graft tines.
Figure 10B:
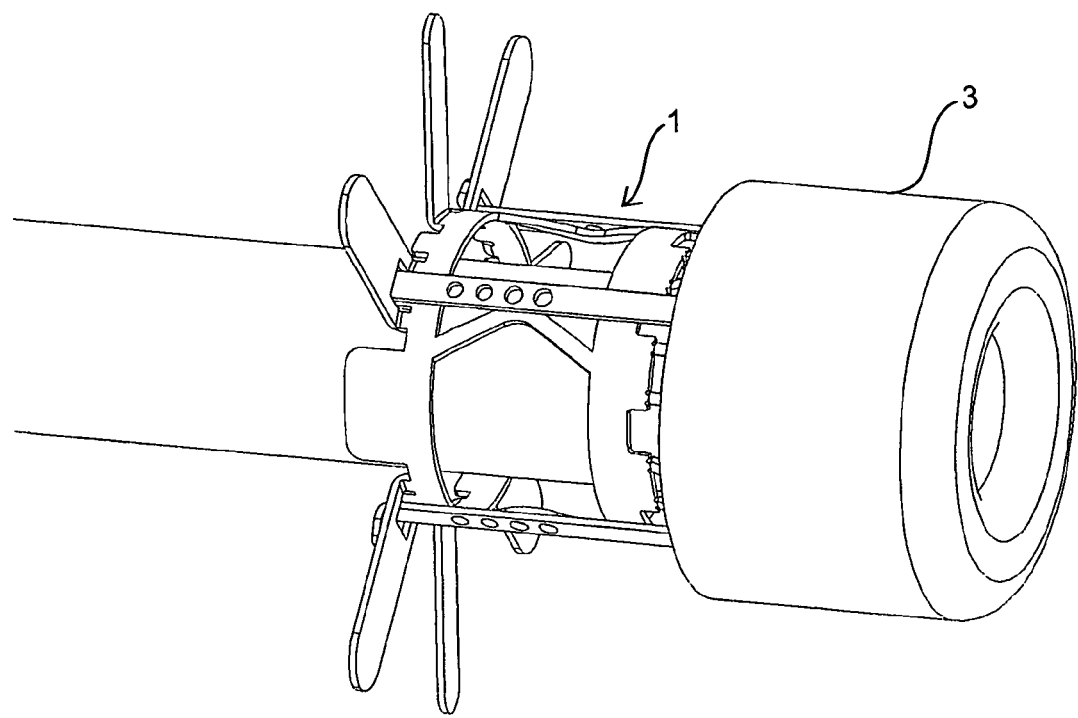
FIG. 10B is a perspective view of the graft vessel shown in FIG. 10A after further having been everted over the device.

When the device is provided separately, a device of appropriate inside diameter will initially be chosen to form a close fit over the graft, with an approximate tolerance of about 0.5 mm, for example. Next the graft is manually threaded through the device so that a portion of a free end of the graft extends from the device. FIGS. 9A and 10A show a graft 3 having been initially inserted through a device 1 as described. The length of the graft end that extends beyond device 1 is more than sufficient to overlap graft tines 14 when the graft end is everted in the next step of the loading procedure. The free end of the graft 3 is next manipulated so as to evert it back over the device as shown in FIGS. 9B and 10B. The manipulation of the free end of the graft 3 may be performed manually, or with one or more pairs of small forceps or the like. After everting the end of graft 3, the everted portion is pressed onto graft tines 14 with sufficient force to pierce the graft 3 with the graft tines 14. With regard to the device shown in FIG. 9B, the graft tines are of sufficient length to extend all the way through the wall of the graft 3 and extend out of the everted wall, as shown. In contrast, the device used in FIG. 10B has shorter graft tines that do not extend through the wall of the graft, so there is no metal exposure from the everted wall.

Figure 11:
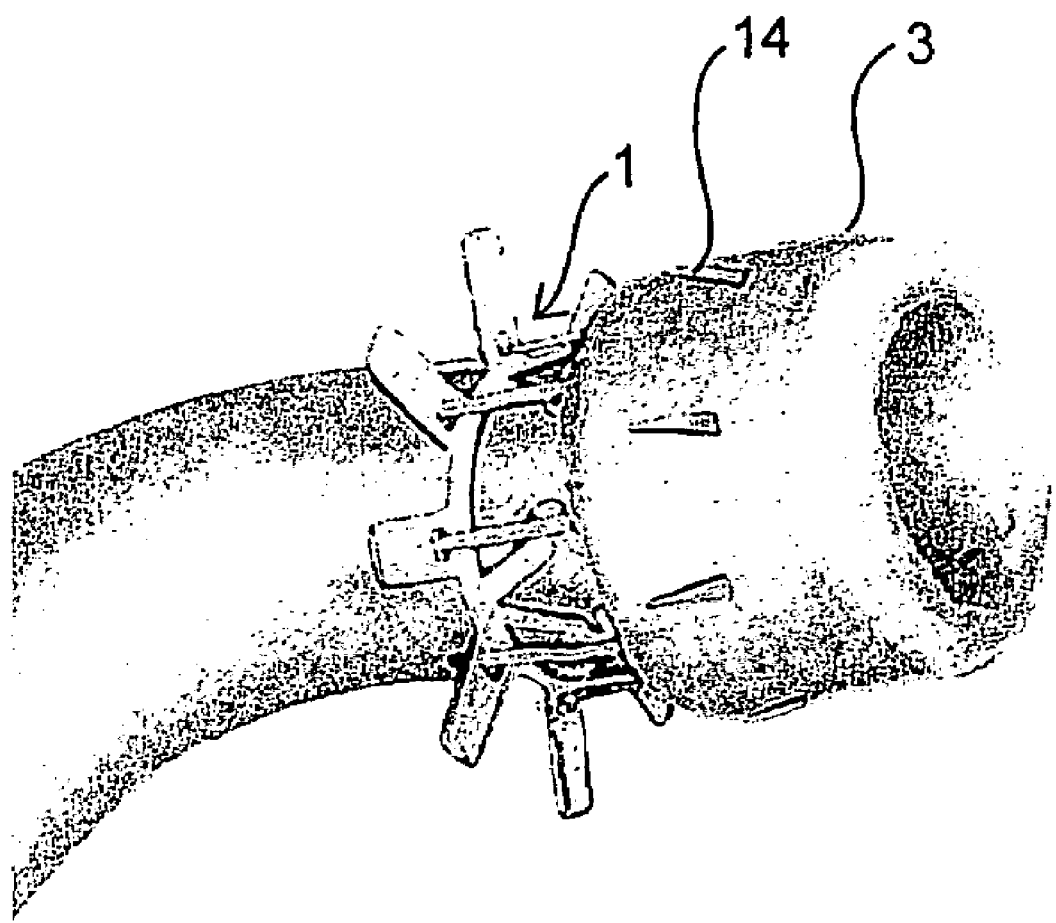
FIG. 11 is a view of the graft and anastomosis device of FIG. 9B, after bending over the graft tines to further secure the graft to the device.

Going back to the example shown in FIG. 9B, graft tines 14 are next bent over in a direction away from the free end of the graft 3, as shown in FIG. 11, to secure the everted end of the graft 3. Graft tines 14 may be manually bent over, by hand or with the use of forceps or other hand held tool. Alternatively, FIGS. 12A and 12B show a side and end view of a tool 80 that can be used to bend over all of the graft tines 14 simultaneously. Tool 80 is designed to concentrically fit over the everted graft end, and may be provided in a kit of tools 80 having a range of inside diameters 82 which are matched to various combinations of the inside diameter of a device 1,100, together with the wall thickness of a graft 3. In this way, the correct spacing can be provided so that a single action can be performed, by sliding the appropriately sized tool 80 over the everted end of the graft 3 and simultaneously driving all of the graft tines 14 to the bent over positions shown in FIG. 12C. Upon removal of tool 80, the mounted graft appears as shown in FIG. 11.

After the graft 3 has been mounted on a device 1,100 as described above, the device 1,100 is next captured in the deployment tool 50. The graft 3 is side loaded in slot 66 and the wedge tube 62 and catch cam tube 64 together are slid between the inside diameter of the device 1,100 and the outside diameter of the graft, whereupon the device 1,100 is captured as described above, thereby capturing the device and graft assembly on the deployment tool 50 in a manner as shown in FIG. 6. At this time, the graft and device assembly are ready to be joined with a vessel in an anastomosis.

Figure 17:
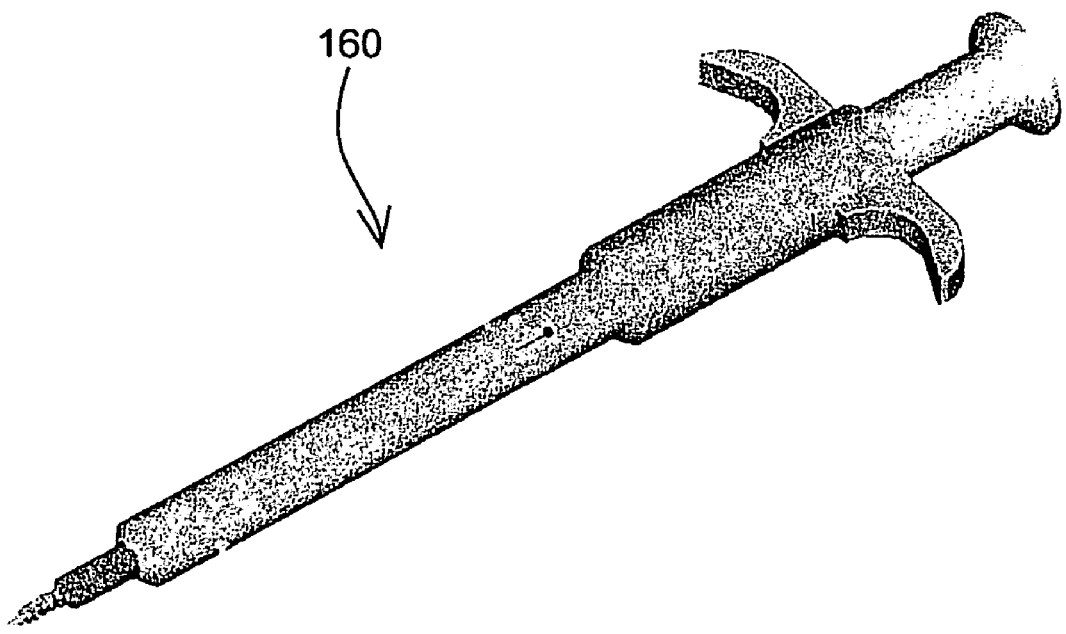
FIG. 17 is a perspective view of an aortotomy punch usable for forming an opening in a target tubular member, for forming an anastomosis at the site of the opening.

Once the graft 3 has been loaded and everted on a device 1,100 and device 1,100 has been captured by deployment tool 50, an aortotomy punch 160 as shown in FIG. 17 or other cutting or punching instrument is used to punch a hole in the wall of the aorta at the site that the anastomosis is to be performed.

Figure 12:
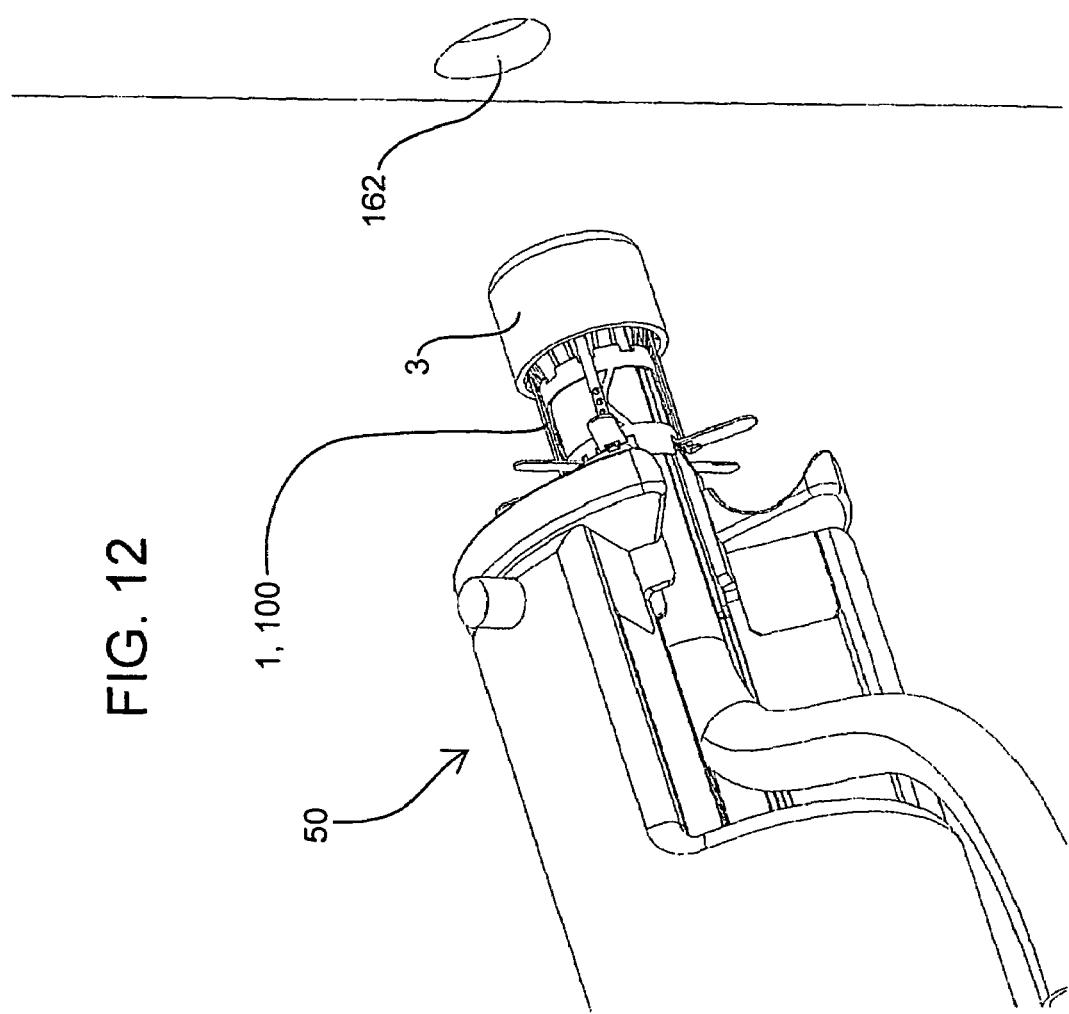
FIG. 12 is a partial perspective view showing the opening in the target vessel into which the graft and anastomosis device are to be inserted.
Figure 13:
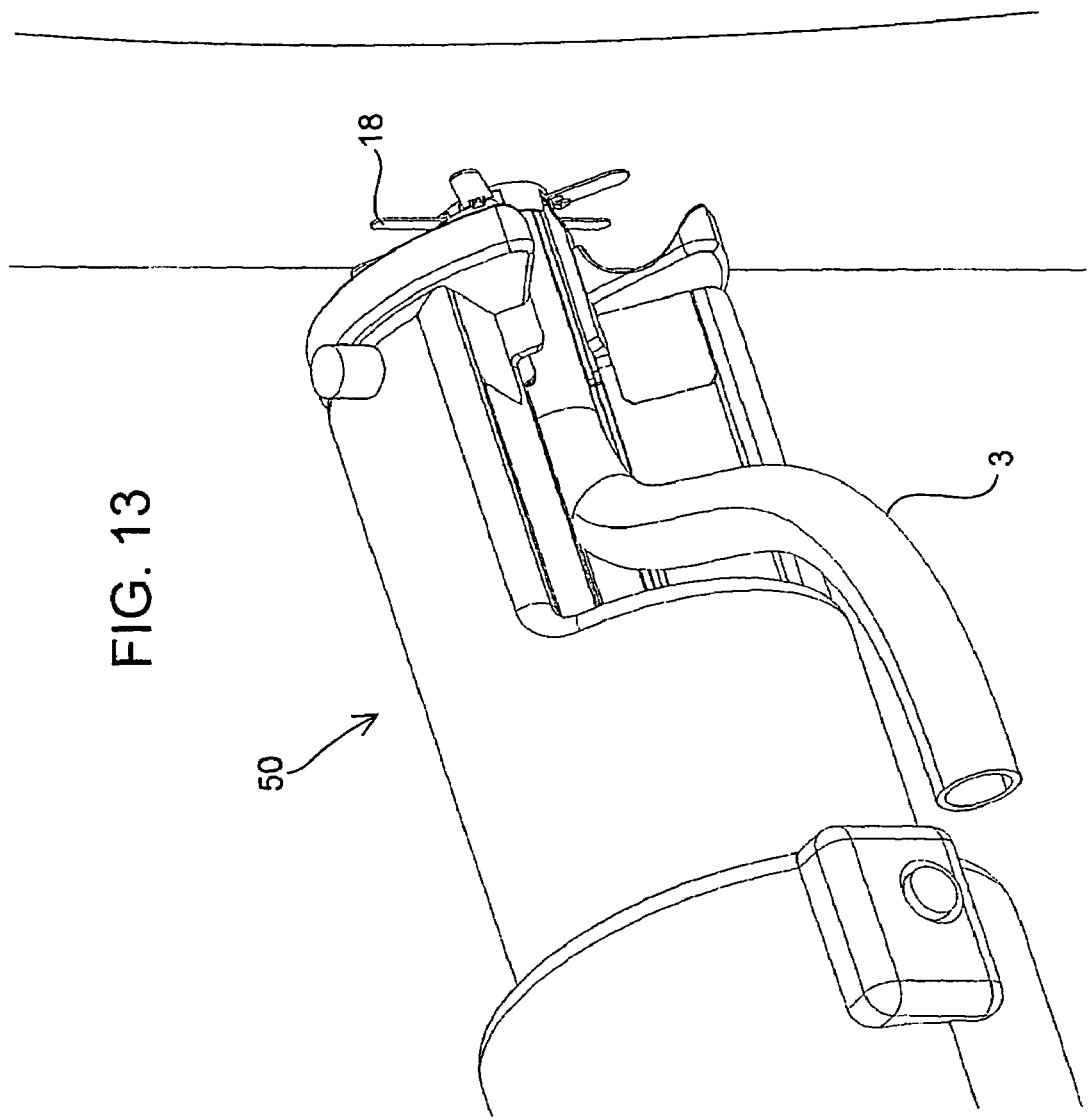
FIG. 13 is a schematic partial view showing insertion of a graft and anastomosis device into an opening in a target vessel using a deployment device according to the present invention.
Figure 14:
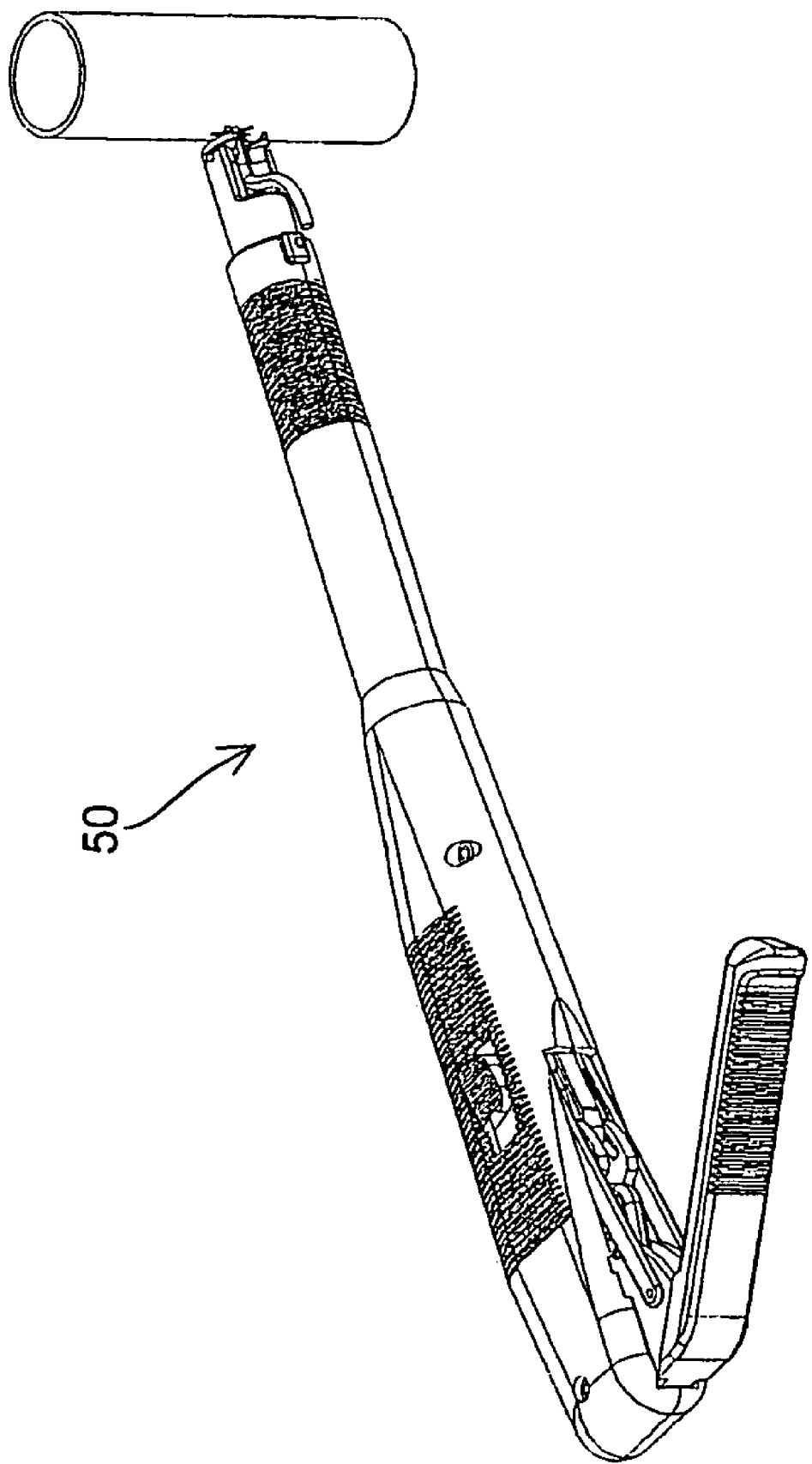
FIG. 14 is a schematic view showing insertion of a graft and anastomosis device into an opening in a target vessel using a deployment device according to the present invention.

Aortotomy punch 160 provides an initial blade stab with a retracting rotary punch that creates a circular aortotomy 162 having a specific diameter that is matched to the outside diameter of the graft 3 everted over the device 1,100, see FIG. 12. For a beating heart procedure, the aortotomy is temporarily sealed, such as by application of finger pressure by the surgeon, to prevent blood loss while the graft assembly is approximated to the aortotomy 162. The finger pressure is then released and the graft/device are inserted into the aortotomy, as shown in FIGS. 13 and 14, preferably using a rolling or rotating motion which allows a rapid insertion to stop the majority of blood flow from the aortotomy 162. The graft/device are inserted until the external tines 18 abut the external wall of the aorta, at which time the deployment of the device begins.

With a single continuous squeeze or depression of the trigger 54 toward the handle 52 of the deployment tool 50, the device 1,100 is compressed, compression fitted and locked to join the graft 3 to the aortic wall, and the deployment tool 50 then releases its capture of the device 1,100 so that the surgeon can remove the deployment tool from inside the device 1,100 with the graft 3 at the same time being slid out of the channel 66, thereby completing the anastomosis.

Figure 15B:
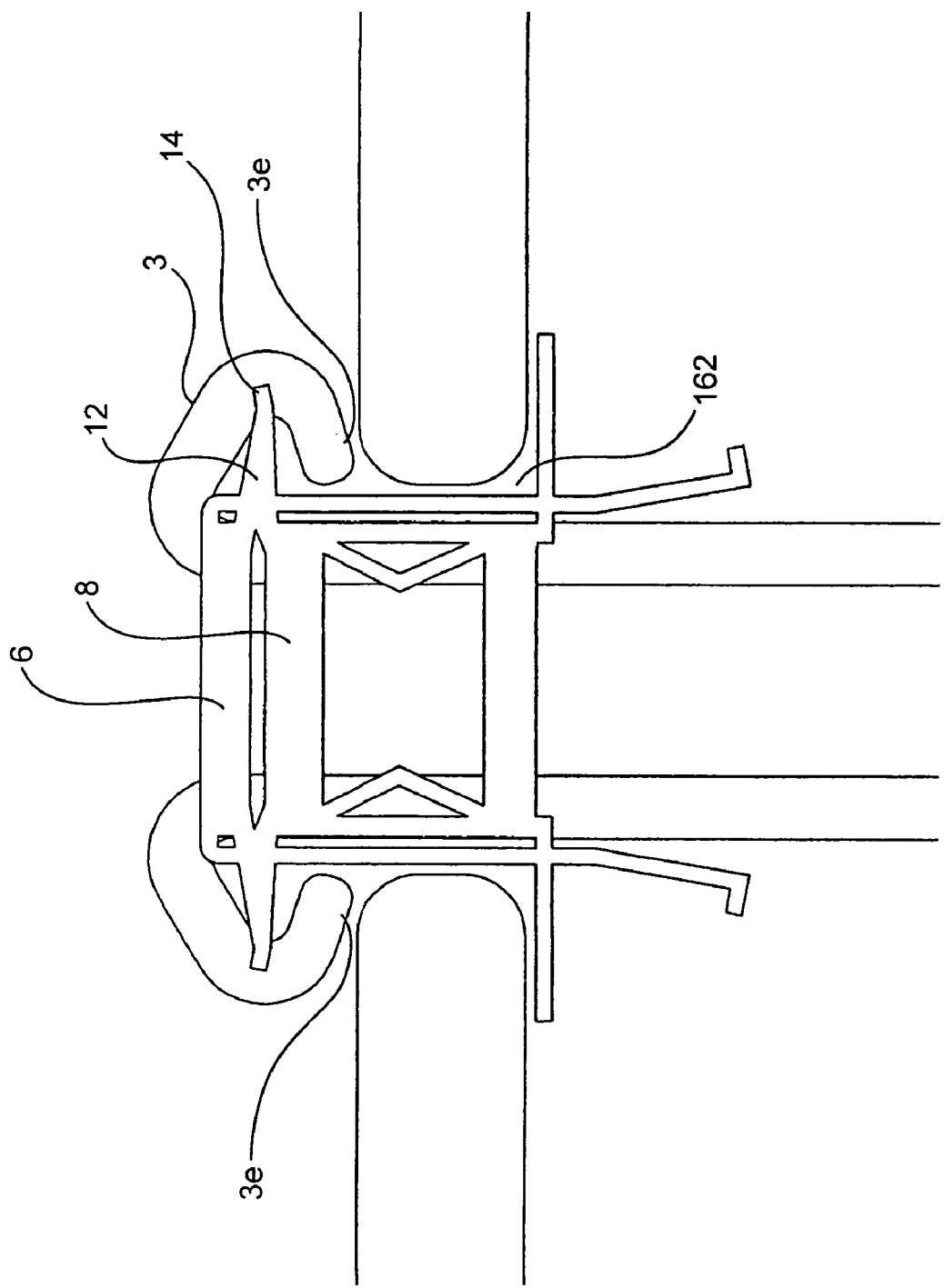
FIG. 15B is a sectional schematic view of the graft and anastomosis device of FIG. 15A after buckling the distal end portion of the anastomosis device.

FIGS. 15A-15D schematically show the various stages of buckling, compressing and locking that are performed in rapid succession during a single pull of the trigger 54. For purposes of clarity, the deployment device has not been shown in FIGS. 15A-15D. In FIG. 15A, the graft 3 and device 1 are shown just after insertion into the aortotomy 162 and prior to squeezing the trigger 54. Initially upon pulling the trigger 54, the retraction of catch cam tube 64 first causes the buckling section between rings 6 and 8 to collapse or buckle, as shown in FIG. 15B. Due to the partially bent configuration of the struts 12, a controlled direction of buckling is assured which causes a mushroom-shaped configuration to result as shown. The buckled configuration of the buckled struts 12 forms an internal retraining structure, which is drawn to provide a compression force of the graft tissue against the internal aortic wall. The shape and direction of buckling of struts 12 are advantageous in that they further evert the proximal end of the graft at 3e so that the intima of the graft 3 approximates the intima of the aorta in preparation for forming an intima to intima anastomosis. The further eversion 3e of the graft also assures that there will be no metal contacting either the intima of the aorta or the intima of the graft at the site of the anastomosis, thereby assuring a more reliable seal and more reliable healing.

Figure 15C:
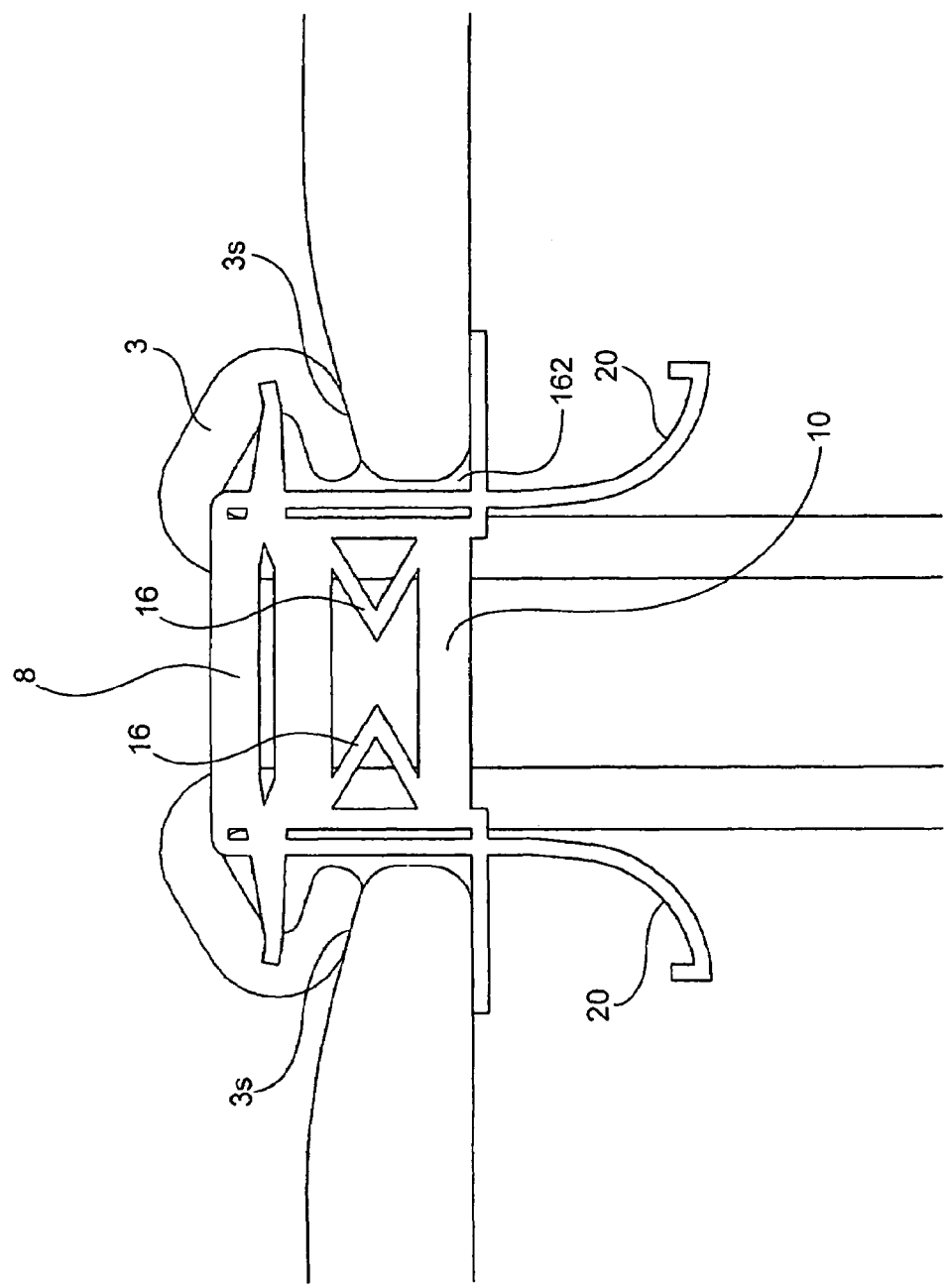
FIG. 15C is a sectional schematic view of the graft and anastomosis device shown in FIG. 15B after having partially collapsed the proximal end section and after beginning to lock the locking tines.

As the trigger 54 continues further in its travel toward the body 52, the struts 16 of the strut section begin to collapse, as shown in FIG. 15C, as the catch cam tube 64 and wedge tube 62 further advance toward stop 70. The collapse of the strut section draws the graft 3 and aorta together with a sufficient force to form a successful seal 3s between the two, while not compressing the anastomosis with too great a force to potentially cause damage to the living tissue. As such, the collapse of the struts 16 draws the rings 8 and 10 closer together, which effectively also draws the buckled struts 12 closer to ring 10, thereby compressing the everted face 3e of the graft and the wall of the aorta. As noted earlier, the extension spring 74 of the deployment device acts as a force limiter, so that the struts 16 are collapsed only so far as to establish a predetermined compression force between the graft 3 and the aorta. In this way, the struts 16 define a compression zone, the length of which is adjustable to provide a predetermined compression force to varying thicknesses of target vessel.

Figure 15D:
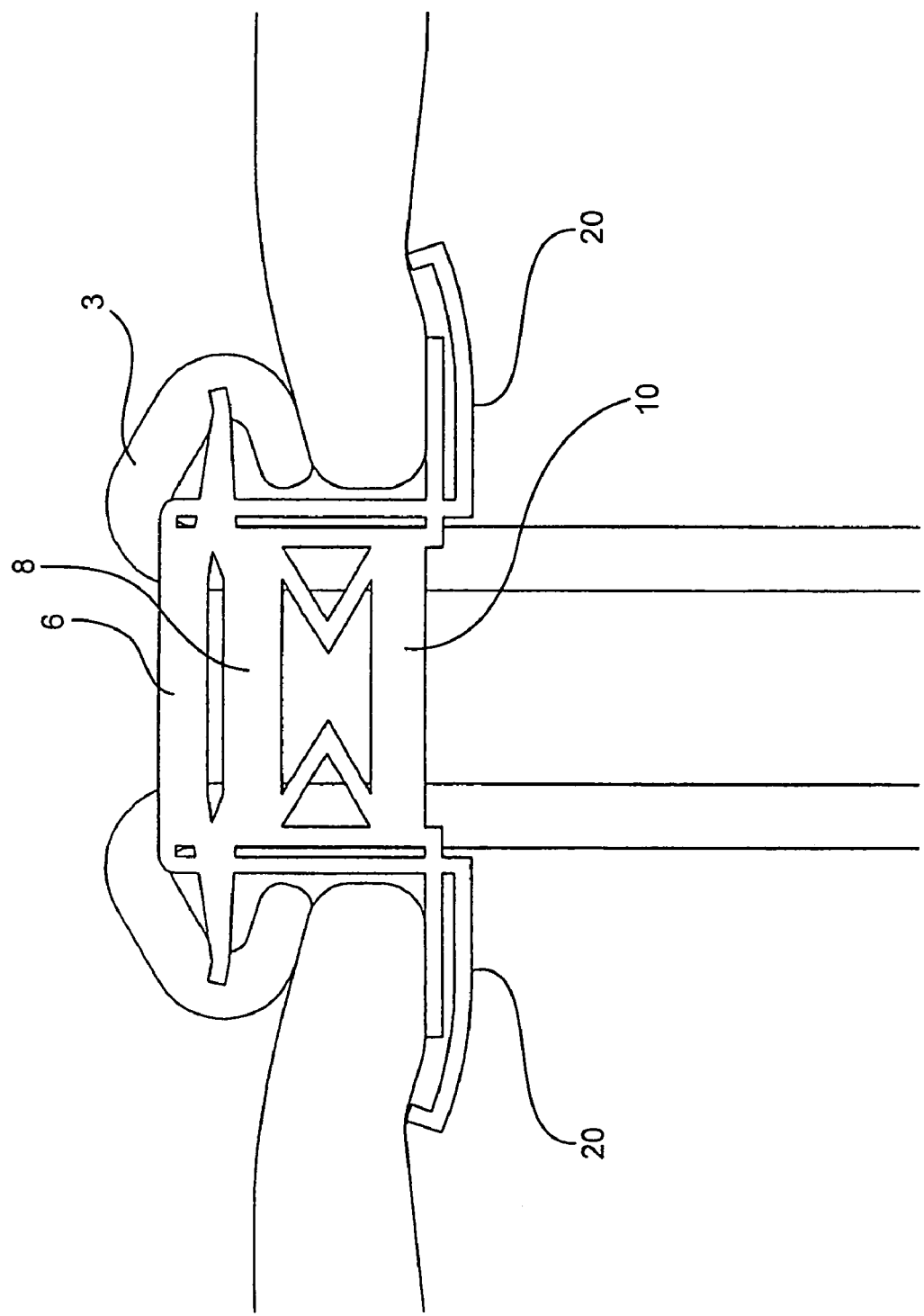
FIG. 15D is a sectional schematic view of the graft and anastomosis device shown in FIG. 15C after having locked the locking tines.

As the trigger 54 continues its motion toward the handle/body 52, and the lock driver 81 is driven in a direction toward the distal end of deployment device 50, the device lock 68 bends over the locking tines 20, as shown in FIG. 15D, thereby firmly locking the relative positions of the rings and 6, 8 and 10, to set the compression force maintaining the anastomosis. The locking tines may be provided with sharp points, barbs, or other configuration at their distal ends to facilitate piercing or other mechanical engagement of the outer wall of the aorta. As the trigger 54 completes its travel toward handle 52, the device lock 68 is retracted back to its neutral starting position, thereby breaking contact with the locking tines 20, and the wedge tube 62 is driven distally so that the wedge portion 62w breaks contact with catch cams 64c, which return to the relaxed position, to define an outside diameter that is smaller than the inside diameter of the device 1. This is the release position of the deployment tool 50, and it allows the distal end portion 60 to be slid out from inside device 1, and the graft 3 is slid out of the groove 66, leaving device 1 and graft 3 undisturbed at the site of the anastomosis.

Figure 16:
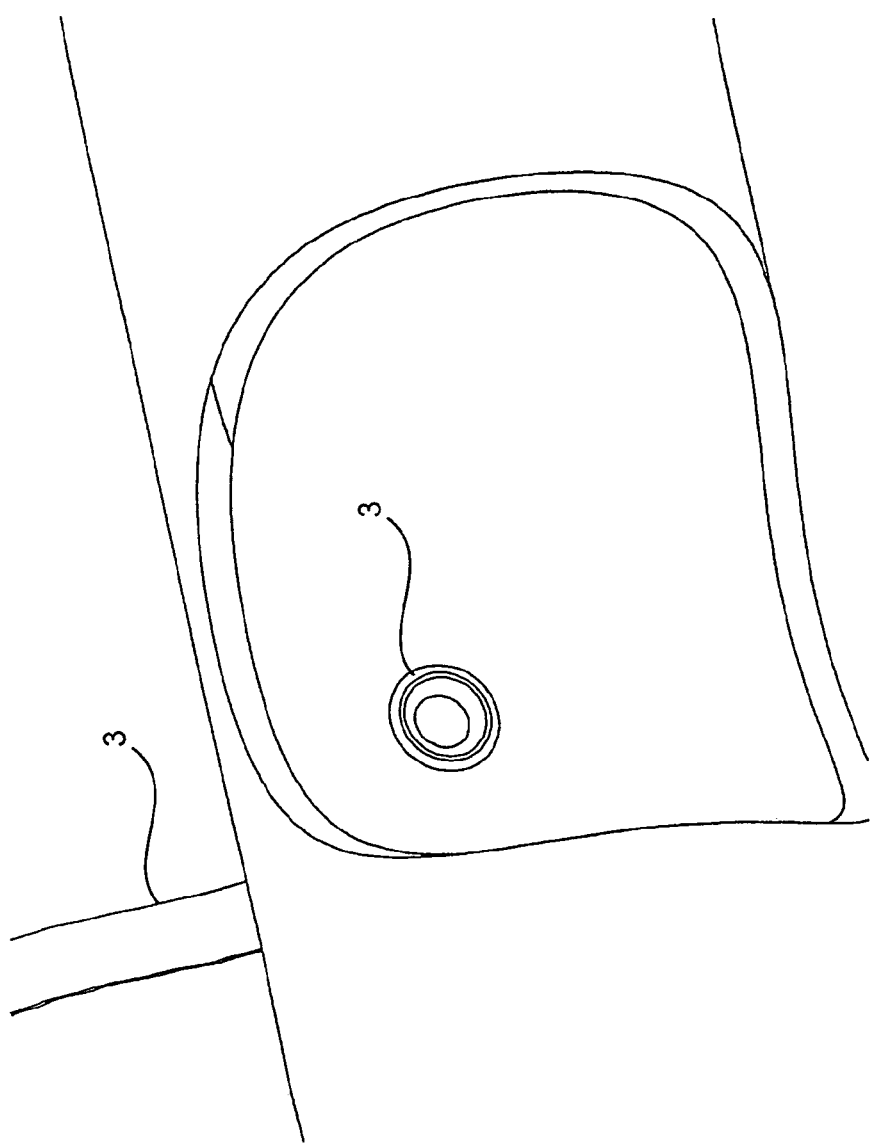
FIG. 16 is a top view of a completed anastomosis viewed on the inside wall of a target vessel.

Device 100 is deployed in the same manner as described above with regard to device 1. However, with only one set of struts 112, the struts expand outwardly by a greater distance and expand beyond the extent of the everted end of the graft 3. Additionally, since the graft tines are located on the ring 106, the graft 3 is not everted to as great an extent as what occurs when buckling the device 1. The result is still an intima to intima anastomosis, but the intima to intima contact is periodically interrupted by the radially extending collapsed struts 112 which extend therebetween. For this reason the device 1 is preferred. FIG. 16 is a top view of a completed anastomosis viewed on the inside wall of a target vessel, where device 1 of FIG. 1B was used to perform the anastomosis. Only the everted graft may be seen and only the everted graft tissue contacts the wall of the target vessel where the seal between the two is formed. With no exposed metal or any portion of device 1 extending from the jointure of the graft and the target vessel, the resultant anastomosis greatly improves the opportunity for healing and growth between the two joined tissue components, and reduces the risk of leakage, clotting, or other deposits which might tend to form on exposed metal.

The device clamp is a two-piece structure that may be molded of ABS plastic or other sufficiently rigid material. A holder arm is pivotally hinged with a clamp arm. A slot is provided in the holder arm and is dimensioned to receive the external tines 18,188 of device 1,100. A ledge or overhang is provided on the inside of the end portion of the holder arm to form a snap fit with a step formed in the end portion of the clamp arm.

After sliding the external tines 18,118 into the slot, the device 1,100 is positioned for clamping. The clamp arm is pivoted toward the holder arm, and with a slight force, the step is snapped into place between the ledge and the main undersurface of the holder arm. The top surface of the end portion of clamp arm applies a compression force against the external tines 18,118 to securely hold the device 1,100 with respect to the device clamp. The device clamp only applies force to the external tines 18,118 and therefore does not apply any hoop stress to the device 1,100 so there is no risk of deformation of the main tubular body portion of the device 1,100 by the device clamp. In this way, the user can grasp the device clamp and manipulate the device 1,100 during loading of the graft 3 without as much concern about deforming the device 1,100, which can easily be done when hand held without the device clamp. The graft 3 can then be mounted in the same way as described above. After a graft 3 has been loaded on the device 1,100, the user presses the release to separate the step from the ledge, thereby releasing the compressive force on the device 1,100. Clamp arm can be swung away from the holder arm, after which the device 1,100 is removed from the device clamp. The release includes a pair of upright arms having ramped surfaces which form a compression or friction lock with the surfaces of the holder arm that they slide against. The release is not limited to this design, as other designs such as a detent mechanism or other snap or friction fit design could be substituted to perform the same function.

An alternative device clamp is a multi-piece structure that may be molded of ABS plastic or other sufficiently rigid material. A holder arm or handle is provided for manipulation of the clamp during capturing of a device, for manipulation/stabilization of the device during loading of a graft 3 and for manipulation in loading a device onto deployment tool 50. The clamping/capturing portion of device clamp may be elevated and extended from the handle, such as by means of an angled support, which is advantageous in that it distances the hand of the user holding handle from deployment instrument 50 as device 1,100 is being mounted on the deployment instrument 50, for example. Of course, the device clamp could be constructed to only elevate the clamping portion above the handle or to simply extend directly from the handle, as would be apparent to those of ordinary skill in the art.

A first support portion extends from the angled support. The first support portion includes slots or recesses configured and dimensioned to receive external tines 18,188 of device 1,100. A removable clamping element is provided to slide over first support portion and engage therewith to capture a device 1,100. The removable clamping element includes slots or recesses which are also configured and dimensioned to receive external tines 18,188 of device 1,100. The clamping portion of the element includes upper arms and lower arms spaced to approximate or slightly compress against the support portion as the arms are slid over the support portion during engagement of the removable clamping element with the main body portion of the clamping device. Stops are provided on each of the lower arms to define recesses in which the first support portion is captured upon engagement of the removable clamping element. Stops also function as a ledge or overhang to form a snap fit with proximal end portions of the first support surface.

Recesses are provided in the top arms which, together with the top surface of first support portion, form slots into which a proximal locking member slides. When engaged in the slots, proximal locking member further secures device 1,100 by preventing the possibility of external tines 18, 188 from escaping from recesses 189. A pivoted release lever is provided for withdrawing the proximal locking member away from the clamping portion for removal of the removable clamping element and release of the device 1, 100.

In order to capture a device (such as device 1 in the device clamp, external tines 18 are positioned in the recesses and removable clamping element is approximated and aligned with first support portion. As the arms are slid over opposite sides of the first support portion, the external tines 18 on the opposite sides of device 1 (opposite those tines 18 residing in the recesses become positioned in other recesses and the removable clamping element locks into engagement with the first support portion via the snap fit between the stops and the proximal end portions. The lever can then be released to allow proximal locking member to slide into position. The recesses are dimensioned to have a depth sufficient to prevent any compressive or clamping forces directly on the external tines upon engagement of the removable clamping element and proximal locking member. Thus, even though the removable clamping element is clamped or secured to the first support portion, no compression or stresses are applied to the external tines as a result of this clamping action. Likewise, the proximal locking element applies no clamping force or stresses to the external tines. In this way, device 1 is securely held in position by the clamping device and prevented from any substantial translation or rotation with respect to the clamping device, without exerting any stresses on the device 1 which could potentially distort or deform it.

The removable clamping element may be further provided with a graft securing element which secures the position of the graft 3 relative to device 1,100 during loading of the graft 3 onto the device 1,100. The graft securing element is provided as a leaf spring element formed of the same material as the removable clamping element and having a relatively weak spring constant, e.g., about 0.1 to about 0.5 lbs./in. Once device 1, 100 has been installed in the clamping device, as described above, a graft 3 may be threaded through the device 1,100 and everted and mounted thereon, as described in more detail above, for example. As the graft 3 is inserted, it is lightly clamped or frictionally held by the graft securing element which supplies a clamping force to graft 3 from opposite sides of the graft. The force is minimal enough to allow the graft to be pulled (slid) though the securing element without damaging the graft, but large enough to prevent the graft 3 from sliding with respect to the securing element absent any additional pulling force on the graft 3.

After a graft 3 has been loaded on the device 1,100, the user presses the lever to slide the proximal locking portion away from the removable clamping element and removes element from engagement with support element, after which the main body portion (and support element) can be removed from the device 1,100, thereby completely releasing the device 1,100.

A protective element, such as a device guard may be provided to further prevent potential damage/deformation to a device 1,100 which is captured by the clamping device. The device guard is configured and dimensioned to be installed over the clamping portion of the clamping device when a device has been installed, as well. The device guard surrounds the device/clamping portion with protective walls which may include a top wall, side walls, and optionally, another side wall at the distal end of the device guard. Side walls include lower rail configurations which are configured to slide along recesses in the main body portion, and may optionally also form a snap fit upon sliding the device guard completely into its protective position. The device guard may be formed of the same materials as the other components of clamping device.

One method of loading a graft 3 on a device 1,100 that has been pre-installed on a deployment device, or if the user should choose to capture the device 1,100 on the deployment device 50 prior to loading the graft 3, is to use one or more graft threading tools. Each graft threading tool includes a long, thin member made of a high tensile strength material such as stainless steel, for example, or other high tensile strength, biocompatible material that can be formed into a wire or fiber. The thin member is formed into a hook at the distal end and further includes a flexible sheath, that may be formed of polyvinyl chloride or other flexible biocompatible polymer. The sheath is configured to slide with respect to the thin member.

One or more graft threading tools may be threaded through the device 1,100 so that distal end hook or hooks extend out to the side of deployment device 50. The hook or hooks are next used to pierce through the graft vessel 3 near a free end thereof. The hooks may pierce the graft vessel wall from either an outside in or inside out direction. The sheath is next slid up into abutment with the end of graft 3 and to overlap the end of the hook for each respective threading tool. By covering the end(s) of hook(s), this eliminates the risk of a hook catching on the device 1,100 as the hook(s) and graft 3 are pulled through the interior of the device 1,100 in the following step. When using a set of four tools and hooking the vessel with four hooks, respectively at substantially evenly circumferentially spaced locations on the graft, the sheaths may not be necessary, particularly when the hooks are pierced through the vessel wall from an outside in direction. Even when using only one hook, there is less need for a sheath when the hook is pierced through the vessel wall in an outside in direction.

The proximal end(s) of the graft threading tool(s) are pulled to slide the graft through the device 1,100. By pulling on the one or more tools the hooks can assist in the eversion of the graft 3 end. The hook or hooks are first pulled outwardly to stretch out the end dimension of the graft, and then downwardly over the device 1,100.

The everted graft end is then impaled by the graft tines in the same manner described above, and the graft tines are bent over, either manually, or by using a tool (e.g., forceps, or other tool) when using a device having tines that extend all the way through the wall of the graft 3. When using a device having shorter graft tines, it is not necessary to bend these graft tines over, since they do not protrude through the everted wall of the graft 3. If no graft tines are used, the end of graft 3 is simply everted over device 1,100. Hook(s) may be removed from the end of the graft 3, or the user may simply choose to cut off a small end length of the graft 3 to which the hook(s) is/are attached, using a scalpel or the like.

Another method of loading a graft 3 on a device 1,100 that has been pre-installed on a deployment device 50 involves the use of a loader. The loader may be mounted over the distal end portion 60 of deployment tool 50, for alignment with the device 1,100 already captured by the deployment tool 50. Advantageously, the deployment tool 50 may be prepackaged with a device 1,100 already in the captured position (i.e., mounted on the distal end portion 60) and with the loader mounted so that the loader performs the additional function of protecting device 1,100 from being damaged during shipment and storage, up until the time of loading a graft 3 on the device 1,100. The loader may be made of molded ABS plastic or other tough polymeric material or metal that is biocompatible and rigid enough to protect device 1, 100 and to perform the loading and eversion procedures discussed hereafter.

The loader may be formed to slide over the distal end portion 60 and form a close sliding fit with the external tube 56 of deployment tool 50, or may be formed to snap fit with the external tube 56. A tongue-and-groove or other interlocking feature (not shown) may be formed in interfacing portions of the loader and deployment tool 50 to enhance the retention forces of the loader on tool 50, such as for purposes of shipping, etc. The loader is designed to break away from the device 1,100 in pieces. The loader is molded in two pieces. The pieces include mating connectors, such as pins and holes, with the holes of one piece arranged to receive the pins of the other piece. The pins may be angled upwardly, or may be flexible to allow the pieces to be rotated away from one another during the loading and eversion procedures. Each of the loader pieces includes a pull tab which may be grasped by the user to apply leverage to the loader to split the pieces apart during the loading and eversion procedure.

A pre-load tool may be used to facilitate piercing of a graft vessel by one or more hooks of one or more graft threading tools. Although the present description refers to preloading the hooks in a graft prior to loading with a loader, it is noted that pre-load tool may be used in the same manner for pre-loading the hook(s) prior to a loading procedure that does not employ the loader, as was described previously. The pre-load tool may be made of ABS plastic, stainless steel, or other rigid polymer or metal that is biocompatible.

The pre-load tool includes proximal and distal eyelets or openings, through which the long, thin filament or wire portions of threading tools are passed respectively, so as to maintain them in parallel alignment during installation of the hooks. The distal end of pre-load tool includes a conical guide designed to receive the open end of the graft to be pierced by the hook(s). The conical guide includes a set of recesses or cut-outs, one aligned with each set of eyelets. The recesses may each be formed with a flattened surface which serves as an anvil against which force may be applied through the graft 3 and hook to accomplish piercing of the graft with the hook.

After installing one or more graft threading tools into the pre-load device, a graft 3 is slid over conical guide and under the hook(s). Force is applied to the hook(s), either manually or with a secondary tool such as forceps or the like, to drive the hook(s) through the wall of the graft 3. After each of the hooks has pierced the graft wall, the pre-load tool is slid away from the graft 3 and threading tool(s) by pulling the tool away from the graft, grasping the proximal end of the tool.

The proximal end(s) of the graft threading tool(s) are next threaded into the channel, through the interior of device 1,100 and out through the opening of the loader. At the same time, graft 3 is guided into the channel, which remains open and uncovered by the loader, since the loader only covers the most distal part of distal end portion 60. Slots are provided in the loader for receiving and securing the proximal end portions of the wires of graft threading tools. The user simply pulls a wire into a slot to secure the wire by a friction fit. A pair of slots is provided in each piece of the loader. After securing the wires, the user grasps the pull tabs and breaks away the loader into its component pieces by applying force to the tabs.

The graft threading devices at this time are still secured by the loader pieces. When four graft threading devices are used as shown in the figures, a pair of the devices are held by one holder piece and the other pair are held by the other holder piece. The user can than manipulate the graft holder pieces to evert the end of the graft by drawing the pieces apart from one another slightly to expand the diameter of the free end of graft 3 and then by guiding the expanded end of the graft down over the device 1,100 by drawing the devices 96 appropriately with the holder pieces.

The everted graft end is then impaled by the graft tines in the same manner described above, and the graft tines are bent over, either manually, or by using a tool. Hook(s) may be removed from the end of the graft 3, or the user may simply choose to cut off a small end length of the graft 3 to which the hook(s) is/are attached, using a scalpel or the like.

In an alternative arrangement, a loading tool is configured to slide over the distal end of deployment tool 50, so that, once device 1, 100 has been loaded/mounted onto deployment tool 50, the loading tool is slid over the distal end 50 (and thus also over device 1,100). The loading tool may form a slight friction fit with deployment tool 50, and may be shipped after sliding it over the distal end to protect device 1,100. Recesses may be formed in the main body of the loading tool which are dimensioned to slide over the distal end of deployment tool 50 and optionally form a friction fit therewith.

A pair of elongated hooks (although three or four or more hooks may be employed) are slidably mounted within a bore or slot through the distal portion of the loading tool, and a handle or trigger is fixed to or integral with hooks to facilitate sliding the hooks longitudinally with respect to the body of loading tool. The handles may be provided for an operator to grasp in order to provide a counter-force to the force exerted by the grasping and sliding handle. The hooks are sprung or oriented so as to assume the open position. Upon sliding the loading tool onto deployment tool 50, so as to assemble it thereon, the hooks are slid along slot or channel 66, and, once having been passed through device 1,100 the hooks expand to their unbiased orientation, such that at least one hook extends out of slot 66.

A free end of graft 3 is next positioned between the hooks. By sliding the handle with respect to the body of the tool, device 1,100 constrains the hooks as they are slid against the confines of the inner circumference of device 1,100, causing the hooks to close down on graft 3, thereby gripping and/or at least partially piercing the adventitia or outer wall of graft 3. Thus, upon sliding, the hooks pull graft 3 into slot 66 and through device 1,100.

As the hooks continue to be pulled through the deployment tool 50, they eventually clear the distal end of device 1,100 and tool 50, at which time the hooks, being no longer confined, return to their open positions, due to the biasing towards such position, as described above. The return of the hooks to the open position releases their grip on graft 3, advantageously positioning the free end of graft 3 to extend beyond device 1,100 by an ideal distance to perform the eversion of graft 3 over device 1,100. The loading tool may then be removed from tool 50 to prepare for the eversion of graft 3 over device 1,100.

An eversion tool may be used to evert a graft over a device 1,100 whether the device is already loaded on a deployment tool or not. The proximal end portion of the eversion tool is tapered to facilitate easy insertion thereof into a distal, open end of the graft 3 to be everted, and to facilitate centering of the proximal end portion of the eversion tool within the open end of graft 3. A doughnut-shaped or other radially symmetrically shaped protrusion may be provided near the proximal end of the eversion tool to facilitate centering of the proximal tip within the graft during insertion. An expandable sleeve is installed over the proximal end portion, distally of the plunger portion at the distal end of the tapered section, to abut proximally against the plunger portion and distally against a proximal end of the main shaft.

The distal end of proximal end portion is configured to slide within a bore or slot formed in main shaft. The slider is configured to slide over the main shaft and is fixed to proximal end portion via a pin, for example, so that as the slider is slid with respect to the main shaft, it pulls or pushes the proximal end portion along with it. By pulling one handle toward the other handle, the slider moves with respect to main shaft. This in turn causes the plunger portion to compress the sleeve against the proximal end. The expandable sleeve may be formed of silicone or other biocompatible, elastomeric material. Upon being compressed as described, the outside diameter of the expandable sleeve increases or expands.

The eversion process described here is equally applicable to a graft 3 and device 1,100 that have already been installed or loaded on a deployment tool 50, as has already been noted. Initially, a tool is inserted into the free end of graft 3 to an extent where proximal end portion of the tool and the sleeve are inside graft 3. Next, the one handle is moved toward the other handle, e.g., the handles are drawn together so as to expand the sleeve as described above. The expansion of the sleeve in turn expands the end of the graft 3. In such an expanded state, the end of graft 3 is much more amenable to eversion, and is easily "rolled" off of the sleeve either by hand or through use of a surgical instrument such as forceps or the like, thereby everting the end of graft 3 over device 1,100 where it is fixed by tines 14. The eversion tool is then removed, with or without releasing the compression on the sleeve, since graft 3 no longer contacts the sleeve. A series of tools are produced having varying sleeve outside diameter sizes to match varying sizes of grafts. Typically, the sleeve sizes are matched to the inside diameters of the series of devices 1, 100 produced.

A combination of a loader and everter tool may be provided which is adapted to both load a graft onto the tool and evert the graft over a device. The combination tool may be used with a deployment tool 50 that has been fitted with a device 1,100, as well as for loading and everting with regard to a device 1,100 that has not yet been installed on a deployment tool 50 to evert the free end of the graft 3 over device 1,100. The expander portion of the combination tool functions essentially the same as that of the eversion tool described above. Additionally, the combination tool is adapted to load the graft over expandable sleeve and to perform the actual eversion step, as will be discussed hereafter.

A loading component is slidably fitted over slider, such that sliding action of the loading component with respect to the slider acts to draw graft 3 over the proximal end portion and expandable sleeve thereof. The loading slider is a component that is configured to slide over the slider and also has hooks mounted thereon. The hooks are circumferentially spaced about the cylindrical tube of the loading slider and run longitudinally with respect thereto, extending substantially beyond the proximal end of the cylinder. In this example, four hooks are spaced 90 degrees apart from each other, although a greater or lesser number of hooks may be effectively employed. The hooks may be biased toward the closed position, but are also forced to assume this position by the reduced inside diameter of the proximal end of the component that they slide against when the component is slid distally, toward the handle of the loading slider. Upon sliding the component proximally, cross pins located within the cylindrical portion of the component force the hooks to the open configuration.

In order to load and evert a graft 3, a free end of graft 3 is first positioned between/in the space circumscribed by the hooks while the hooks are in the open configuration. Next, graft 3 is grasped by the hooks when an operator, using the handles slides the component toward the handle of the loading slider. By holding the slider handle and continuing to slide the loading slider handle in the same direction, the entire loading component slides distally toward the slider handle by way of the loading slider sliding over the slider, thereby pulling graft 3 along with it and loading the end of graft 3 over the proximal end portion and expandable sleeve. The end of graft 3 is then expanded by expanding the expandable sleeve in the manner described above. To evert the graft 3 end, the loading component is slid proximally with respect to the slider. The proximal end of the everter/hook control component is beveled or contoured so as to gently evert the end of graft 3 as it abuts against the end of graft 3 during sliding, since the diameter of the expanded graft is now larger than the inside diameter of the component. After successful eversion of graft 3 over device 1, 100, the component is again slid proximally, so that the hooks open and release their hold on graft 3. The combination tool is then removed in order to allow placement of the graft and completion of the anastomosis.

An alternative everter tool employs a spring loaded main shaft which may be distally extended by pushing a handle proximally with respect to a main body. A return spring biases the main shaft back to an initial position when no force is being exerted on the handle. A plurality of prongs extend proximally from the main body and converge against the main shaft distally of the anchor. Although five prongs are used in this example, it should be understood that a lesser or greater number of prongs may be employed to achieve substantially the same functionality as described herein. A reduced diameter pin or tip may be provided to extend proximally of the anchor to serve to guide the insertion of the anchor into a vessel 3, as described below. The anchor and/or tip further serve to keep the prongs centered during the insertion, to ensure that none of the prongs becomes positioned outside of the graft 3 wall.

The main shaft may be comprised as a telescoping assembly with a proximal portion slidably received, in a telescoping fashion, in a distal portion. The proximal portion is proximally biased by a biasing means, such as a spring which pushes the proximal portion proximally until a pin abuts against the proximal end of a slot.

In order to perform an eversion, the alternative eversion tool is maneuvered to insert the anchor (optionally led by the tip) into an open end of graft 3, for example. The tapered leading surfaces of the anchor are shaped and dimensioned to wedge or press the outer wall of graft 3 against the inner surfaces of device 1,100 to prevent graft 3 from backsliding through device 1,100 during performance of the eversion. After graft 3 has been secured by the anchor against device 1,100, an operator advances the handle of the tool while maintaining the body portion (via handles) in it current position relative to graft 3. This action drives the main shaft proximally relative to the main body portion. Since the anchor can travel no further in the proximal direction, one portion of main shaft begins to retract into another portion, as this other portion continues to move proximally. At the same time, the advancement of the enlarged portion at the proximal end of the distal portion against the prongs acts as a cam driving the prongs to expand radially away from the anchor, and as they expand, they expand the end of graft 3 as well.

Once the end of graft 3 has been expanded sufficiently to be everted over device 1,100, the operator advances the entire eversion tool further proximally, e.g., by advancing the handles together as a unit. This further proximal movement causes the prongs to push or drive the expanded end of graft 3 proximally, which causes it to evert, while the proximal portion retracts further into the distal portion. To prevent any possibility of graft 3 end from hanging up on any of the prongs, the slider is next advanced proximally, while maintaining the remainder of the tool in its current position. The slider is freely longitudinally slidable over the main body, being retrained at proximal and distal limits of the slot provided therein by a pin extending from the main body and riding in the slot. The slider includes scraper arms having radially fixed positions so as to ride over the prongs as the slider is advanced proximally. Thus, any portion of graft 3 which may remain over any of the prongs at this time will be "scraped off" by scraper arms as they are advanced against the prongs. Optionally, the scraper arms may each contain a groove or notch to further ensure that the prongs maintain contact with the scraper arms, as they ride in grooves as the scraper is advanced. Upon completing the eversion, the eversion tool is removed from the everted graft to allow further processing of the anastomosis.

A sizing tool may be provided that is useful for measuring the outside diameter of a graft to be used in an anastomosis, as well as the wall thickness of the graft 3. These measurements are important for forming a leak proof seal in the wall of a target vessel. To prevent leakage and form structurally intact anastomoses, device 1,100, deployment tool 50, a tool for forming a hole or opening in the target vessel, and potentially even the loaders must be matched to the size of the graft 3. The sizing tool provides a convenient way to measure the outside diameter and wall thickness of the graft and also may facilitate matching the graft 3 measured with a set of devices and tools of proper size, as described hereafter.

The sizing tool includes two concentric disks which are arranged to rotate relative to one another. The disks may be molded from ABS plastic or made of other sufficiently rigid and biocompatible plastic or metal. Radiused grooves are formed in the perimeter of outer disk, and have various widths and radii of curvature for measuring a range of outside diameters. For example, the groove widths/diameter may range from about 0.110 inches to about 0.300 inches, although these dimensions may be varied according to the application for which the tool is used. For example, the range may be a range of larger or a range of smaller widths/diameters for use with larger or smaller applications/grafts to be anastomosed. Angled prongs extend from the inner disk. The prongs extend substantially parallel to the faces of the inner and outer disks and have varying heights to define various gap lengths by which a range of graft wall thicknesses may be measured. For example, the gaps may range from about 0.010 inches to about 0.060 inches, although these dimensions may be varied according to the application for which the tool is used. For example, the range may be a range of larger or a range of smaller gaps for use with larger or smaller applications/grafts to be anastomosed.

In use, a graft 3 is slid into one or more of the radiused grooves in an orientation such that the longitudinal axis of the graft 3 is perpendicular to the face of the disk. The groove into which the graft 3 fits without leaving any space between the graft and the sides of the groove, and which does not deform or squeeze in the walls of the graft 3 as it is fitted into the groove, identifies the outside diameter of the graft 3. After finding the properly fitting groove, the outside diameter of the graft can be identified by reading the value for the width of that groove, which is labeled on the outer disk. To measure the wall thickness of the graft, a free end of the graft is slid over one or more of the angled prongs until the prong defining the correct gap distance is discovered. The correct gap distance is the one into which the wall of the graft fits without leaving any additional space in the gap and where the prong does not deform or squeeze into the wall of the graft. After finding the prong defining the correct gap distance, the thickness of the graft wall can be identified by reading the gap distance or thickness, which is labeled on the inner disk.

The sizing tool may further be used to combine the outside diameter measurement of the graft 3 and the graft wall thickness measurement to determine the size of device 1,100 and matching deployment tool 50, as well as other tools and punch to be used in performing the anastomosis. In at least one embodiment, the outer disk has ten possible outside diameter measurements that can be determined, while the inner disk can measure six different wall thicknesses. Various combinations of outside diameter and wall thickness may have overlapping requirements for the size of device and punch to be used in performing the anastomosis. For example, a graft with a relatively smaller outside diameter and a relatively thicker wall thickness may require the same diameter hole in the target vessel as a second graft having a relatively larger outside diameter, but relatively thinner wall thickness. This is because once everted, the outside diameter of the device 1,100 and everted graft will be a combination of the outside diameter of the graft 3 in addition to twice the graft wall thickness. Presently, the inventors have defined four sizes of devices, deployment tools and associated tools for the various combinations of graft outside diameters and wall thicknesses that can be measured by the sizing tool. However, the present invention is certainly not limited to four sizes, as fewer or greater numbers of size variations could be correlated with the combinations of outside diameters and wall thicknesses that are measurable with a sizing tool. Nor is the sizing tool to be limited to the capability for measuring 10 outside diameter sizes and six wall thickness sizes, as more or fewer or each capability could readily be provided on a sizing tool in view of the description of the exemplary tool.

In order to match the measurements obtained by the sizing tool, the inner disk is provided with columns of color-coded indicators with each column extending radially outward from the center of the disk and being aligned with one of the angled prongs, respectively. Each column contains four color-coded indicators in this example, and the indicators in each column are aligned about four concentric circles so as to align with windows in the back side of the disk which are formed along concentric circles. Each groove is radially aligned with one window. For example, the window that is aligned with the smallest groove is also aligned with the innermost concentric circle, so that the innermost color indicator of any column is visible in this window when any particular prong is aligned with the smallest groove. The window that is aligned with the largest groove is also aligned with the outermost concentric circle, so that the outermost color indicator of any column is visible through this window when the corresponding prong is aligned with the largest groove. The windows in the intermediate grooves "step down" from the outermost concentric circle to the innermost concentric circle.

The color indicators are permanently applied to the back surface of the inner disk, such as by silk screening, for example, and each has one of four possible colors which is determined by the gap length of the prong with which it is radially aligned, and the concentric circle with which it is radially aligned. These two factors represent the wall thickness and outside diameter which ultimately determine the size of the device and tools to be used, which are color coded to one of the four colors.

In using the color-coding feature, the prong which was identified as providing a proper measure of the wall thickness of the graft 3 is aligned with the groove which was found to properly measure the outside diameter of the graft 3. Alignment is performed by rotating the inner disk with respect to outer disk or vice versa. Upon aligning the identified groove and prong, the user then flips over the sizing device, which indicates a color in the window that is radially aligned with the chosen prong and groove. This color indicates to the user the size of device 1,100 and associated tools to use in performing the anastomosis of the graft 3 that was measured, as the devices and tools are color-coded to match the measurements provided by the sizing tool.

Another embodiment of a sizing tool that is useful for measuring the outside diameter of a graft to be used in an anastomosis, as well as the wall thickness of the graft 3, includes two concentric disks which are arranged to rotate relative to one another. These disks may be molded from ABS plastic or made of other sufficiently rigid and biocompatible plastic or metal. Radiused grooves are formed in the perimeter of the outer disk, and have various widths and radii of curvature for measuring a range of outside diameters. For example, widths of the radiused grooves may range from about 3.5 mm to about 7.0 mm, although these dimensions may be varied according to the application for which the tool is used. For example, the range may be a range of larger or a range of smaller widths/diameters for use with larger or smaller applications/grafts to be anastomosed.

Indices may be provided (such as by molding them into a plastic disk, engraving into a metal disk, or otherwise printing them on a disk of any construction) to indicate the outside diameter size measured by the groove associated therewith. Angled prongs extend from the inner disk. The prongs extend substantially parallel to the faces of the inner and outer disks and have slots which face the grooves. The slots are aligned with the grooves and are adapted to receive a wall of a free end of a graft to measure the thickness thereof. The widths of the slots may range from about 0.010 inches to about 0.040 inches, for example, although these dimensions may be varied according to the application for which the tool is used. For example, the range may be a range of larger or a range of smaller widths for use with larger or smaller applications/grafts to be anastomosed. Indices may be provided on the inner disk (such as by molding them into a plastic disk, engraving into a metal disk, or otherwise printing them on a disk of any construction) to indicate the gap measured by the prong associated therewith.

In use, a graft 3 is slid into one or more of the radiused grooves in an orientation such that the longitudinal axis of the graft 3 is perpendicular to the face of the outer disk. The groove into which the graft 3 fits without leaving any space between the graft and the sides of the groove, and which does not deform or squeeze in the walls of the graft 3 as it is fitted into the groove, identifies the outside diameter of the graft 3. After finding the properly fitting groove, the outside diameter of the graft can be identified by reading the value for the width of that groove, by reading the associated index number which is labeled on the outer disk. To measure the wall thickness of the graft, a free end of the graft is slid over one or more of the angled prongs until the prong defining the correct gap distance is discovered. The correct gap distance is the one into which the wall of the graft fits without leaving any additional space in the gap and where the prong does not deform or squeeze into the wall of the graft. After finding the prong defining the correct gap distance, the thickness of the graft wall can be identified by reading the gap distance or thickness, which is labeled by the index number on the inner disk.

The sizing tool may further be used to combine the outside diameter measurement of the graft 3 and the graft wall thickness measurement to determine the size of device 1,100 and matching deployment tool 50, as well as other tools and punch to be used in performing the anastomosis. The inner disk includes a handle mounted on the face thereof which is adapted to be manually rotated by a user. The inner disk is rotatably mounted within the outer disk, which is provided with a circular recess in which the inner disk is rotatably received. The outer disk further contains a central opening through which radiused tabs, which extend from the back side of the inner disk, are inserted. The tabs include prongs or ledge features which lock or engage with the back surface of the outer disk after insertion of the tabs through an opening, thereby preventing separation of the inner disk from the outer disk, while allowing rotation of the inner disk with respect to the outer disk. Thus, by holding the outer disk in one hand and rotating the handle with the other, the inner disk may be rotated relative to the outer disk. Detents or other incremental rotational markers may be employed to assist in lining up the prongs with the grooves during the process of rotating. In this example, the outer disk has eight possible outside diameter measurements that can be determined, while the inner disk can measure four different wall thicknesses. Various combinations of outside diameter and wall thickness may have overlapping requirements for the size of device and punch to be used in performing the anastomosis. For example, a graft with a relatively smaller outside diameter and a relatively thicker wall thickness may require the same diameter hole in the target vessel as a second graft having a relatively larger outside diameter, but relatively thinner wall thickness. This is because once everted, the outside diameter of the device 1,100 and everted graft will be a combination of the outside diameter of the graft 3 in addition to twice the graft wall thickness. Presently, the inventors have defined four sizes of devices, deployment tools and associated tools for the various combinations of graft outside diameters and wall thicknesses that can be measured by the sizing tool. However, the present invention is certainly not limited to four sizes, as fewer or greater numbers of size variations could be correlated with the combinations of outside diameters and wall thicknesses that are measurable with a sizing tool. Nor is the sizing tool to be limited to the capability for measuring eight outside diameter sizes and four wall thickness sizes, as more (as described previously, for example) or fewer of each capability could readily be provided on a sizing tool in view of the description of the exemplary tool described above.

In order to match the measurements obtained by the sizing tool, the outer disk is provided with columns of color-coded indicators (not shown) with each column extending radially inward from and aligned with the grooves, respectively A window is provided in alignment with each of the prongs in the inner disk. Each window has a different radial distance from the center of inner disk, so that, when aligned with one of the color columns, varying colors appear based upon the size of the prong gap/radial positioning of the associated window. In this way, an appropriately sized device 1, 100, delivery instrument 50, punch, etc. can be selected based upon a composite measurement of the outside diameter and wall thickness of the graft 3 being measured. The color indicators may be permanently applied to the face of the disk, such as by silk screening, for example.

In using the color-coding feature, the prong which was identified as providing a proper measure of the wall thickness of the graft 3 is aligned with the groove which was found to properly measure the outside diameter of the graft 3. Alignment is performed by rotating the inner disk with respect to the outer disk, in a manner as described above. Upon aligning the identified groove and prong, the user then views the color that is visible through the window that is aligned with the identified groove and prong. This color indicates to the user the size of device 1,100 and associated tools to use in performing the anastomosis of the graft 3 that was measured, as the devices and tools are color-coded to match the measurements provided by the sizing tool.

In another alternative embodiment, a sizing tool that is useful for measuring the outside diameter of a graft to be used in an anastomosis, as well as the wall thickness of the graft 3, is provided in the form of a linear gauge. This sizing tool provides a convenient way to measure the outside diameter and wall thickness of the graft and also may facilitate matching the graft 3 measured with a set of devices and tools of proper size, as described hereafter.

The linear gauge sizing tool includes a unitary main body having a graduated slot defined by side walls or edges. The distance between the edges gradually decreases to establish predefined distances therebetween to establish a linear, sliding scale for measuring the outside diameter of a graft 3. The main body may be molded from ABS plastic or made of other sufficiently rigid and biocompatible plastic or metal. Reinforcing ribs or other rigidifying members may be provided to increase the overall stiffness/rigidity of the linear gauge sizing tool, and, in particular, may also be provided at the back side of the edges. Indicia may be provided along the sliding scale defined by the slot, to indicate the outside diameters measured at various locations along the scale. Numerical indicators may be included. For example, the numbers may indicate outside diameter measurements, in millimeters.

Semicircular grooves are provided along an edge of the main body and are arranged for measuring the wall thickness of a graft 3. A free end of graft 3 is inserted into the slot to determine generally the wall thickness of the graft 3. Grooves function as "go-no go" gauges, wherein, if the end of the graft is able to slide into the slot, then it is determined that the wall thickness of the graft is approximately of the size measured by that particular gauge. The inner border of the larger groove prevents a graft 3 that would fit into the smaller gauge from being insertable into the larger sized gauge. In one example, the gauge includes only two wall thickness gauges, for simplicity of operation. However, more grooves of varying sizes and widths could be added to further break down the categorization between different wall thicknesses measured. In addition for measurement of the wall thicknesses and outside diameters of the grafts to be used, the gauge provides zones delineated by indicia, so that measurements which fall within one of the zones will indicate a color-coded set of device 1,100, deployment instrument 50, punch, etc. to use for the particular graft being measured. The zoned areas between the indicators may be colored for immediate visual identification of a color-coded group of devices and instruments to be used.

Performing the Anastomosis

The present invention is applicable for performing a variety of anastomosis procedures, including coronary artery bypass grafting. One or more anastomoses are performed on a target vessel within a patient, by connecting one or both ends of a graft to the target vessel. The following description pertains to a specific, non-limiting application of the present invention in performing an end-to-side anastomosis of a proximal end of a graft to the wall of the aorta.

The description begins with the surgical site having already been prepared for performance of the anastomosis. The anastomosis can be performed with the heart stopped and the patient on cardiopulmonary bypass or during a beating heart bypass procedure. Examples of grafts appropriate for use in performing an anastomosis include an internal mammary artery having only one free end (the end on which the anastomosis is to be performed), a saphenous vein graft having two free ends (in which case it is possible to perform the distal anastomosis first, if desired, as noted above) or some other suitable graft, the graft is preferably first measured to determine the length of graft needed, as well as the outside diameter and wall thickness of the graft at the free end to be joined with the aorta. The wall thickness and outside diameter may be measured with a sizing device as described above, or may be measured manually or with other tools.

After selection and preparation of the graft to be used, the determination of the outside diameter and wall thickness of the proximal end of the graft 3, the proper corresponding size of device 1,100 is selected, together with a deployment tool 50 that is matched to the size of the selected device 1,100. When using a sizing device with a color-coding feature, the user simply chooses the color-coded package that matches the color of the indicator that is determined by the measurements of the wall thickness and outside diameter of the graft 3. The color coded package contains a matching size device 1,100, matching size deployment tool 50, matching size punch 160 and optionally a matching loader, pre-load tool and/or one or more graft threading tools.

Next, the proximal end of the graft 3 is loaded and everted onto the device 1, by passing the proximal end 3 through the interior of the device 1,100 by one of the methods described above, depending upon whether the device 1,100 has already been captured on the deployment tool 50 and on the types of loading tools being used everted over the proximal end of the device 1,100, as shown in FIGS. 9A-9B and 10A-10B. In the case of FIGS. 9A-9B, where elongated graft tines 14 are employed, such as with the device 1 of FIG. 1A, or with device 100 of FIG. 3, the tines 14 pierce and extend through the wall of the graft 3 as shown in FIG. 9B. In this situation, the tines are preferably further bent over, after the eversion, as shown in FIG. 11, to facilitate insertion of the graft 3 and device 1,100 through the opening in the target vessel for performance of the anastomosis. In the case of a device 1,100 which uses the shortened tines (such as the device 1 shown in FIG. 1B, for example) or which uses no tines at all, tines do not extend through the wall of the vessel 3 upon performance of the eversion, as shown in FIG. 10B. The shortened tines 14 pierce into the wall, but do not extend through and out of the wall. When no tines are used, the appearance is the same as shown in FIG. 10B. FIG. 6 shows the graft 3 having been loaded on a device 1,100 and onto a deployment tool 50. As described above, by advancing button 58 distally, the wedge 62w of wedge 62 extends beyond catch cams 64c, thereby allowing device 1,100 (along with graft 3) to be mounted on the tool 50. The concentric tubes 62,64,65 of the distal end of tool 50 are inserted between the graft 3 and device 1,100. The portion of the graft which extends in the direction of the trigger 54 can be positioned within channel 66, as shown in FIG. 6. Once the graft 3 has been loaded and everted on a device 1,100 and device 1,100 has been captured by deployment tool 50 in any order as described above, an aortotomy punch 160 is used to punch a hole in the wall of the aorta at the site that the anastomosis is to be performed.

Aortotomy punch 160 provides an initial blade stab with a retracting rotary punch that creates a circular aortotomy 162 having a specific diameter that is matched to the outside diameter of the graft 3 everted over the device 1,100, see FIG. 12. For a beating heart procedure, the aortotomy is temporarily sealed, such as by application of finger pressure by the surgeon, to prevent blood loss while the graft assembly is approximated to the aortotomy 162. The finger pressure is then released and the graft/device are inserted into the aortotomy, as shown in FIGS. 13 and 14, preferably using a rolling or rotating motion which allows a rapid insertion to stop the majority of blood flow from the aortotomy 162. The graft/device are inserted until the external tines 18 abut the external wall of the aorta, at which time the deployment of the device begins.

With a single continuous squeeze or depression of the trigger 54 toward the handle 52 of the deployment tool 50, the device 1,100 is compressed, compression fitted and locked to join the graft 3 to the aortic wall, and the deployment tool 50 then releases its capture of the device 1,100 so that the surgeon can remove the deployment tool from inside the device 1,100 with the graft 3 at the same time being slid out of the channel 66, thereby completing the anastomosis.

Alternatively to the use of aortotomy punch 160 in the above-described method, a slit may be cut into the target vessel using the blade of an integrated cutting device. Although the cutting device may be formed integrally with a delivery device 50, it is preferred to make the cutting device removable from delivery device 50 to facilitate loading the device 1,100 as well as everting the graft vessel 3, such as according to processes described above, prior to attaching the cutting device to device 50. The cutting device may be adapted to clip on to the body of device 50, and may be provided with a pair of clip arms which are somewhat deflectable to allow the body of device 50 to be positioned therebetween. A spring force is applied by the arms against the body of device 50 as they are deflected during installing the cutting device on device 50, the spring force being generated upon deflection of the arms as the body of device 50 deflects them. The spring force, together with frictional forces between the arms and the body of device 50 maintains the cutting device in an integrated position. Of course, other alternative connecting means could be provided for mounting a removable cutting device to a device 50 as would be readily apparent to those of ordinary skill in the art, such as by attaching by screws, or other removable attachment means.

The blade of the cutting device may be a sharp-tipped, razor blade-like implement or other sharp cutting instrument designed to form a slit in the target vessel, of a length which has been determined to be sufficient to insert the device 1,100 and everted graft vessel 3 through to accomplish the anastomosis. The cutting device is provided with an extending foot which is adapted to be placed in contact with the target vessel when the blade has pierced the target vessel sufficiently to form the desired slit, acting as a stop to indicate when the slit has been completed. The arms that are extensions of the foot act as a site to properly position and target the blade to form the slit at the desired target location, and also function to target further steps in the anastomosis process.

By maintaining pressure against the distal end of the arm extending from the blade, such as by applying finger pressure thereto (alternatively, a tension spring (not shown) may be connected to a linkage to bias the blade to the extended position) the blade is maintained in the extended position. In such position, the operator of the integrated device then advances the integrated device to apply the blade to a location on the target vessel where it is desired to perform the anastomosis. The blade is inserted into the target vessel and the integrated device is advanced toward the target vessel until a sufficient slit length is achieved, typically when the foot contacts the target vessel.

By maintaining contact between the foot and the target vessel, this ensures that device 50 maintains device 1,100 and the everted end of graft vessel 3 in alignment with the slit in the target vessel. The operator then releases the pressure and advances device 50 further toward the target vessel to install device 1,100 and everted graft end 3 into the slit. The blade is mounted to the cutting device via a linkage (e.g., such as a four bar linkage) which causes the blade to retract both proximally and radially away from the slit/anastomosis site as device 50 and the main body portion of the cutting device which is clipped to device 50, are advanced toward the target vessel. This leaves a clear path for the insertion of device 1,100 and everted graft vessel 3 by delivery device 50 which is held in alignment with the slit, as guided by the foot. Once device 1,100 and everted graft end 3 are inserted into the slit, the remainder of the anastomosis proceeds in the same manner as described above with regard to the process that employed the aortotomy punch 160. The cutting device simplifies the earlier described approach, by doing away with the need for aortotomy punch 160 and thus providing a "one shot" technique.

FIGS. 15A-15D schematically show the various stages of buckling, compressing and locking that are performed in rapid succession during a single pull of the trigger 54. For purposes of clarity, the deployment device has not been shown in FIGS. 15A-15D. In FIG. 15A, the graft 3 and device 1 are shown just after insertion into the aortotomy 162 and prior to squeezing the trigger 54. Initially upon pulling the trigger 54, the retraction of catch cam tube 64 first causes the buckling section between rings 6 and 8 to collapse or buckle, as shown in FIG. 15B. Due to the partially bent configuration of the struts 12, a controlled direction of buckling is assured which causes a mushroom-shaped configuration to result as shown. The buckled configuration of the buckled struts 12 forms an internal retaining structure, which is drawn to provide a compression force of the graft tissue against the internal aortic wall. The shape and direction of buckling of struts 12 are advantageous in that they further evert the proximal end of the graft at 3e so that the intima of the graft 3 approximates the intima of the aorta in preparation for forming an intima to intima anastomosis. The further eversion 3e of the graft also assures that there will be no metal contacting either the intima of the aorta or the intima of the graft at the site of the anastomosis, thereby assuring a more reliable seal and more reliable healing.

As the trigger 54 continues further in its travel toward the body 52, the struts 16 of the strut section begin to collapse, as shown in FIG. 15C, as the catch cam tube 64 and wedge tube 62 further advance toward stop 70. The collapse of the strut section draws the graft 3 and aorta together with a sufficient force to form a successful seal 3s between the two, while not compressing the anastomosis with too great a force to potentially cause damage to the living tissue. As such, the collapse of the struts 16 draws the rings 8 and 10 closer together, which effectively also draws the buckled struts 12 closer to ring 10, thereby compressing the everted face 3e of the graft and the wall of the aorta. As noted earlier, the extension spring 74 of the deployment device acts as a force limiter, so that the struts 16 are collapsed only so far as to establish a predetermined compression force between the graft 3 and the aorta. In this way, the struts 16 define a compression zone, the length of which is adjustable to provide a predetermined compression force to varying thicknesses of target vessel.

As the trigger 54 continues its motion toward the handle/body 52, and the lock driver 81 is driven in a direction toward the distal end of deployment device 50, the device lock 68 bends over the locking tines 20, as shown in FIG. 15D, thereby firmly locking the relative positions of the rings and 6, 8 and 10, to set the compression force maintaining the anastomosis. The locking tines may be provided with sharp points, barbs, or other configuration at their distal ends to facilitate piercing or other mechanical engagement of the outer wall of the aorta. As the trigger 54 completes its travel toward handle 52, the device lock 68 is retracted back to its neutral starting position, thereby breaking contact with the locking tines 20, and the wedge tube 62 is driven distally so that the wedge portion 62w breaks contact with catch cams 64c, which return to the relaxed position, to define an outside diameter that is smaller than the inside diameter of the device 1. This is the release position of the deployment tool 50, and it allows the distal end portion 60 to be slid out from inside device 1, and the graft 3 is slid out of the groove 66, leaving device 1 and graft 3 undisturbed at the site of the anastomosis.

Device 100 is deployed in the same manner as described above with regard to device 1. However, with only one set of struts 112, the struts expand outwardly by a greater distance and expand beyond the extent of the everted end of the graft 3. Additionally, since the graft tines are located on the ring 106, the graft 3 is not everted to as great an extent as what occurs when buckling the device 1. The result is still an intima to intima anastomosis, but the intima to intima contact is periodically interrupted by the radially extending collapsed struts 112 which extend therebetween. With no exposed metal or any portion of device 1 extending from the jointure of the graft and the target vessel, the resultant anastomosis greatly improves the opportunity for healing and growth between the two joined tissue components, and reduces the risk of leakage, clotting, or other deposits which might tend to form on exposed metal.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A method of performing an anastomosis to join a graft to a target vessel, said method comprising the steps of:
   measuring an outside diameter and wall thickness of the graft vessel;
   selecting an appropriately sized anastomosis device, based on the outside diameter and wall thickness measurements;
   loading the graft vessel on the anastomosis device so that the graft vessel passes through a longitudinally extending annular space defined by a main body of the anastomosis device, extends beyond a distal end of the anastomosis device and is everted back over an external surface of the distal end of the anastomosis device;
   selecting a punch appropriately size matched to the outside diameter and wall thickness measurements and punching an opening through a wall of the target vessel;
   inserting the loaded graft into the opening, wherein the anastomosis device has an enlarged proximal end that is incapable of passing through the opening and abuts against the wall of the target vessel upon inserting the loaded graft;
   buckling the anastomosis device so that a distal end portion thereof increases in diameter and compresses the everted end of the graft vessel against an internal wall surface of the target vessel.

2. The method of claim 1, wherein the graft vessel has a second free end.

3. The method of claim 1, wherein a second end of the graft vessel is in fluid communication with another vessel or organ.

4. A method of performing an anastomosis to join a first conduit to a second conduit, said method comprising the steps of:
   inserting a free end of the first conduit through an annular space defined by an anastomosis device so that the free end extends beyond a second end of the device, and wherein at least one first end member of the device extends further radially outward than a radial extent of the main body of the device defining the annular space;
   everting the extending free end of the graft over the second end of the device, wherein the inner wall of the graft remains free from contact with the device;
   forming an opening through a wall of the second conduit, wherein the opening is dimensioned to allow the everted end and main body, but not the at least one first end member to pass therethrough;
   inserting the device and a portion of the first conduit into the opening until the at least one first end member abuts the external wall of the second conduit; and
   compressing the device to buckle the second end portion, wherein the second end portion, upon buckling is no longer capable of passing back through the opening.

5. The method of claim 4, wherein said compressing is performed only up until a pre-defined compression force has been reached.

6. The method of claim 4, further comprising locking the relative positions of first and second end portions of the device after completion of said compressing.

7. The method of claim 4, wherein said compressing the device to buckle the second end portion further everts the first conduit and draws the everted inner wall of the first conduit against an inner wall of the second conduit.

8. The method of claim 4, wherein said first and second conduits are joined by contact between inner wall surfaces of said first and second conduits, free of any contact with the device.

9. A method of performing an anastomosis to join a first conduit to a second conduit, said method comprising:
   providing a tool for deployment of and having mounted thereon an anastomosis device, a free end of the first conduit having been inserted through an annular space defined by the anastomosis device and everted over the anastomosis device;
   forming an opening through a wall of the second conduit;
   inserting the device and an everted portion of the first conduit into the opening;
   compressing the device to buckle a distal end portion of the device, wherein upon buckling the distal end portion, the device is no longer capable of being retracted through the opening; and
   further compressing the device to buckle a portion proximal of the distal end portion, wherein the portion proximal of the distal end portion in a buckle state does not substantially increase in outside diameter relative to a pre-buckled state of the portion proximal of the distal end portion.

10. The method of claim 9, wherein said compressing is performed only up until a pre-defined compression force has been reached.

11. The method of claim 9, further comprising locking the device in the buckled configuration.

12. The method of claim 9, wherein said compressing the device to buckle the device further everts the first conduit and draws the everted inner wall of the first conduit against an inner wall of the second conduit.

13. The method of claim 9, wherein said first and second conduits are joined by contact between inner wall surfaces of said first and second conduits, free of any contact with the device.

14. The method of claim 1, further comprising buckling a portion of the anastomosis device proximal of the distal end portion, so that the portion of the anastomosis device proximal of the distal end portion does not substantially increase in diameter.

15. The method of claim 14, wherein said buckling a portion of the anastomosis device proximal of the distal end portion is performed subsequent to said buckling the anastomosis device so that a distal end portion thereof increases in diameter.

16. The method of claim 4, further comprising buckling a portion of the device between the second end portion and the first end member in a manner wherein the portion between the second end portion and the first end member does not substantially increase in diameter.

17. The method of claim 4, further comprising buckling a portion of the device between the second end portion and the first end member, wherein the portion between the second end portion and the first end member is buckled in directions perpendicular to directions of buckling of the second end portion that occur during said compressing the device to buckle the second end portion.

18. The method of claim 17, wherein said buckling a portion of the device between the second end portion and the first end member is performed subsequent to buckling of the second end portion.

19. The method of claim 17, wherein said compressing the device to buckle a portion proximal of the distal end portion is preformed subsequent to said compressing the device to buckle a distal end portion of the device.

* * * * *

UNITED STATES PATENT AND TRADEMARK OFFICE
CERTIFICATE OF CORRECTION

PATENT NO. : 7,585,306 B2
APPLICATION NO. : 10/867430
DATED : September 8, 2009
INVENTOR(S) : Abbott et al.

It is certified that error appears in the above-identified patent and that said Letters Patent is hereby corrected as shown below:

Column 3, line 35, please delete "said second end portion adapted to buckle in a radially outward, direction" and insert --second end portion adapted to buckle in a radially outward direction--;
Column 14, line 36, please delete "it is has been" and insert --it has been--;
Column 21, line 36, please delete "18,188" and insert --18,118--;
Column 22, line 18, please delete "18,188" and insert --18,118--;
Column 22, line 23, please delete "18,188" and insert --18,118--;
Column 22, line 38, please delete "18,188" and insert --18,118--;
Column 23, line 21, please delete "removes element" and insert --removes the element--;
Column 23, line 22, please delete "with support element" and insert --with the support element--;
Column 25, line 30, please delete "user can than" and insert --user can then--.

Signed and Sealed this
Eighth Day of February, 2011

David J. Kappos
*Director of the United States Patent and Trademark Office*